United States Patent
Schenk

(10) Patent No.: US 7,208,265 B1
(45) Date of Patent: Apr. 24, 2007

(54) METHOD OF CRYOPRESERVING SELECTED SPERM CELLS

(75) Inventor: John L. Schenk, Fort Collins, CO (US)

(73) Assignee: XY, Inc., Fort Collins, CO (US)

( * ) Notice: Subject to any disclaimer, the term of this patent is extended or adjusted under 35 U.S.C. 154(b) by 0 days.

(21) Appl. No.: 09/478,299

(22) Filed: Jan. 5, 2000

Related U.S. Application Data

(60) Provisional application No. 60/167,423, filed on Nov. 24, 1999.

(51) Int. Cl.
*A01N 1/00* (2006.01)
(52) U.S. Cl. ...................................................... 435/1.1
(58) Field of Classification Search ................. 435/2
See application file for complete search history.

(56) References Cited

U.S. PATENT DOCUMENTS

| | | |
|---|---|---|
| 3,299,354 A | 1/1967 | Hogg |
| 3,499,435 A | 3/1970 | Rockwell et al. |
| 3,547,526 A | 12/1970 | Devereux |
| 3,644,128 A | 2/1972 | Lipner |
| 3,661,460 A | 5/1972 | Elking et al. |
| 3,687,806 A | 8/1972 | Van den Bovenkamp |
| 3,710,933 A | 1/1973 | Fulwyler et al. |
| 3,761,941 A | 9/1973 | Robertson |
| 3,810,010 A | 5/1974 | Thom |
| 3,826,364 A | 7/1974 | Bonner et al. |
| 3,829,216 A | 8/1974 | Persidsky |
| 3,833,796 A | 9/1974 | Fetner et al. |
| 3,877,430 A | 4/1975 | Wieder |
| 3,893,766 A | 7/1975 | Hogg |
| 3,894,529 A | 7/1975 | Shrimpton |
| 3,909,744 A | 9/1975 | Wisner et al. |
| 3,947,093 A | 3/1976 | Goshima et al. |
| 3,960,449 A | 6/1976 | Carleton et al. |
| 3,963,606 A | 6/1976 | Hogg |
| 3,973,003 A | 8/1976 | Colas |
| 3,973,196 A | 8/1976 | Hogg |
| 4,007,087 A | 2/1977 | Ericsson |
| 4,009,260 A | 2/1977 | Ericsson |
| 4,014,611 A | 3/1977 | Simpson et al. |
| 4,067,965 A | 1/1978 | Bhattacharya |
| 4,070,617 A | 1/1978 | Kachel et al. |
| 4,083,957 A | 4/1978 | Lang |
| 4,085,205 A | 4/1978 | Hancock |
| 4,092,229 A | 5/1978 | Bhattacharya |
| 4,155,831 A | 5/1979 | Bhattacharya |
| 4,162,282 A | 7/1979 | Fulwyler et al. |
| 4,178,936 A | 12/1979 | Newcomb |
| 4,179,218 A | 12/1979 | Erdmann et al. |
| 4,191,749 A | 3/1980 | Bryant |
| 4,200,802 A | 4/1980 | Salzman et al. |
| 4,225,405 A | 9/1980 | Lawson |
| 4,230,558 A | 10/1980 | Fulwyler |
| 4,255,021 A | 3/1981 | Brunsden |
| 4,267,268 A | 5/1981 | Nelson, Jr. ............ 435/2 |
| 4,274,408 A | 6/1981 | Nimrod |
| 4,274,740 A | 6/1981 | Eidenschink et al. |
| 4,276,139 A | 6/1981 | Lawson |
| 4,302,166 A | 11/1981 | Fulwyler et al. |
| 4,317,520 A | 3/1982 | Lombardo et al. |
| 4,318,480 A | 3/1982 | Lombardo et al. |
| 4,318,481 A | 3/1982 | Lombardo et al. |
| 4,318,482 A | 3/1982 | Barry et al. |
| 4,325,483 A | 4/1982 | Lombardo et al. |
| 4,327,177 A | 4/1982 | Shrimpton |
| 4,339,434 A | 7/1982 | Ericsson |
| 4,341,471 A | 7/1982 | Hogg et al. |
| 4,350,410 A | 9/1982 | Minott |
| 4,352,558 A | 10/1982 | Eisert |
| 4,361,400 A | 11/1982 | Gray et al. |
| 4,362,246 A | 12/1982 | Adair |

(Continued)

FOREIGN PATENT DOCUMENTS

BR 9704313 6/1999

(Continued)

OTHER PUBLICATIONS

Amann, Rupert P.; "Cryopreservation of Sperm," *Encyclopedia of Reproduction*, 1:733-783 (1999).
Arriola, J. and Foote, R. H.; "Glycerolation and Thawing Effects on Bull Spermatozoa Frozen in Detergent-Treated Egg Yolk and Whole Egg Extenders," *J Dairy Sci*, 70:1664-1670 (1987).
Behrman, S. J. and Ackerman, D. R.; "Freeze Preservation of Human Sperm," *Am. J. Obstet. and Gynec.*, 103:5:654-664 (1969).
Foote, R. H., "Buffers and Extenders: What Do They Do? Why Are They Important?" *Proc of the 10th NAAB Tech. Conf. on Artificial Insemination and Reproduction*, 62-70 (1984).

(Continued)

*Primary Examiner*—Michael Meller
(74) *Attorney, Agent, or Firm*—Santangelo Law Offices P.C.

(57) ABSTRACT

The present invention provides a method of cryopreserving sperm that have been selected for a specific characteristic. In a preferred embodiment, the method is employed to freeze sex-selected sperm. Although the cryopreservation method of the invention can be used to freeze sperm selected by any number of selection methods, selection using flow cytometry is preferred. The present invention also provides a frozen sperm sample that has been selected for a particular characteristic, such as sex-type. In preferred embodiments, the frozen sperm sample includes mammalian sperm, such as, for example, human, bovine, equine, porcine, ovine, elk, or bison sperm. The frozen selected sperm sample can be used in a variety of applications. In particular, the sample can be thawed and used for fertilization. Accordingly, the invention also includes a method of using the frozen selected sperm sample for artificial insemination or in vitro fertilization.

28 Claims, No Drawings

U.S. PATENT DOCUMENTS

| | | |
|---|---|---|
| 4,395,397 A | 7/1983 | Shapiro |
| 4,395,676 A | 7/1983 | Hollinger et al. |
| 4,400,764 A | 8/1983 | Kenyon |
| 4,422,761 A | 12/1983 | Frommer |
| 4,448,767 A | 5/1984 | Bryant |
| 4,474,875 A | 10/1984 | Shrimpton ................... 435/2 |
| 4,487,320 A | 12/1984 | Auer |
| 4,498,766 A | 2/1985 | Unterleitner |
| 4,501,366 A | 2/1985 | Thompson |
| 4,511,661 A | 4/1985 | Goldberg |
| 4,515,274 A | 5/1985 | Hollinger et al. |
| 4,523,809 A | 6/1985 | Taboada et al. |
| 4,538,733 A | 9/1985 | Hoffman |
| 4,559,309 A | 12/1985 | Evenson |
| 4,598,408 A | 7/1986 | O'Keefe |
| 4,600,302 A | 7/1986 | Sage, Jr. |
| 4,605,558 A | 8/1986 | Shrimpton |
| 4,631,483 A | 12/1986 | Proni et al. |
| 4,637,691 A | 1/1987 | Uehara et al. |
| RE32,350 E | 2/1987 | Bhattacharya |
| 4,654,025 A | 3/1987 | Cassou et al. |
| 4,660,971 A | 4/1987 | Sage et al. |
| 4,673,288 A | 6/1987 | Thomas et al. |
| 4,680,258 A | 7/1987 | Hammerling et al. |
| 4,683,195 A | 7/1987 | Mullis et al. |
| 4,683,202 A | 7/1987 | Mullis |
| 4,691,829 A | 9/1987 | Auer |
| 4,698,142 A | 10/1987 | Muroi et al. |
| 4,702,598 A | 10/1987 | Böhmer |
| 4,714,680 A | 12/1987 | Civin |
| 4,744,090 A | 5/1988 | Freiberg |
| 4,749,458 A | 6/1988 | Muroi et al. |
| 4,756,427 A | 7/1988 | Gohde et al. |
| 4,758,729 A | 7/1988 | Monnin |
| 4,764,013 A | 8/1988 | Johnston |
| 4,780,451 A | 10/1988 | Donaldson |
| 4,790,653 A | 12/1988 | North, Jr. |
| 4,794,086 A | 12/1988 | Kasper et al. |
| 4,818,103 A | 4/1989 | Thomas et al. |
| 4,831,385 A | 5/1989 | Archer et al. |
| 4,836,038 A | 6/1989 | Baldwyn |
| 4,845,025 A | 7/1989 | Lary et al. |
| 4,846,785 A | 7/1989 | Cassou et al. |
| 4,877,965 A | 10/1989 | Dandliker et al. |
| 4,942,305 A | 7/1990 | Sommer |
| 4,959,354 A | 9/1990 | Barbetti |
| 4,965,204 A | 10/1990 | Civin |
| 4,979,093 A | 12/1990 | Laine et al. |
| 4,980,277 A | 12/1990 | Junnila ...................... 435/2 |
| 4,981,580 A | 1/1991 | Auer |
| 4,983,038 A | 1/1991 | Ohki et al. |
| 4,987,539 A | 1/1991 | Moore et al. |
| 4,988,619 A | 1/1991 | Pinkel |
| 4,999,283 A | 3/1991 | Zavos et al. |
| 5,005,981 A | 4/1991 | Schulte et al. |
| 5,007,732 A | 4/1991 | Ohki et al. |
| 5,021,244 A * | 6/1991 | Spaulding ................... 424/561 |
| 5,030,002 A | 7/1991 | North, Jr. |
| 5,034,613 A | 7/1991 | Denk et al. |
| 5,055,393 A | 10/1991 | Kwoh et al. |
| 5,079,959 A | 1/1992 | Miyake et al. |
| 5,084,004 A | 1/1992 | Ranoux |
| 5,088,816 A | 2/1992 | Tomioka et al. |
| 5,098,657 A | 3/1992 | Blackford et al. |
| 5,101,978 A | 4/1992 | Marcus |
| 5,127,729 A | 7/1992 | Oetliker et al. |
| 5,132,548 A | 7/1992 | Borden et al. |
| 5,135,759 A | 8/1992 | Johnson ...................... 424/561 |
| 5,144,224 A | 9/1992 | Larsen |
| 5,150,313 A | 9/1992 | Van den Engh et al. |
| 5,159,397 A | 10/1992 | Kosaka et al. |
| 5,159,403 A | 10/1992 | Kosaka |
| 5,162,306 A | 11/1992 | Donaldson |
| 5,167,926 A | 12/1992 | Kimura et al. |
| 5,180,065 A | 1/1993 | Touge et al. |
| 5,182,617 A | 1/1993 | Yoneyama et al. |
| 5,195,979 A | 3/1993 | Schinkel et al. |
| 5,199,576 A | 4/1993 | Corio et al. |
| 5,215,376 A | 6/1993 | Schulte et al. |
| 5,219,729 A | 6/1993 | Hodgen |
| 5,247,339 A | 9/1993 | Ogino |
| 5,259,593 A | 11/1993 | Orme et al. |
| 5,260,764 A | 11/1993 | Fukuda et al. |
| 5,298,967 A | 3/1994 | Wells |
| 5,315,122 A | 5/1994 | Pinsky et al. |
| 5,346,990 A | 9/1994 | Spaulding |
| 5,359,907 A | 11/1994 | Baker et al. |
| 5,366,888 A | 11/1994 | Fry et al. |
| 5,367,474 A | 11/1994 | Auer et al. |
| 5,370,842 A | 12/1994 | Miyazaki et al. |
| 5,371,585 A | 12/1994 | Morgan et al. |
| 5,412,466 A | 5/1995 | Ogino |
| 5,437,987 A | 8/1995 | Teng et al. |
| 5,439,362 A | 8/1995 | Spaulding |
| 5,447,842 A | 9/1995 | Simons |
| 5,452,054 A | 9/1995 | Dewa et al. |
| 5,461,145 A | 10/1995 | Kudo et al. |
| 5,466,572 A | 11/1995 | Sasaki et al. |
| 5,467,189 A | 11/1995 | Kreikebaum et al. |
| 5,471,294 A | 11/1995 | Ogino |
| 5,471,299 A | 11/1995 | Kaye et al. |
| 5,480,774 A | 1/1996 | Hew et al. |
| 5,483,469 A | 1/1996 | Van den Engh et al. |
| 5,494,795 A | 2/1996 | Guerry et al. |
| 5,496,272 A | 3/1996 | Chung et al. |
| 5,503,994 A | 4/1996 | Shear et al. |
| 5,514,537 A | 5/1996 | Chandler ...................... 435/2 |
| 5,523,573 A | 6/1996 | Hanninen et al. |
| 5,532,155 A | 7/1996 | Ranoux |
| 5,558,998 A | 9/1996 | Hammond et al. |
| 5,578,449 A | 11/1996 | Fr asch et al. |
| 5,589,457 A | 12/1996 | Wiltbank et al. |
| 5,596,401 A | 1/1997 | Kusuzawa |
| 5,601,235 A | 2/1997 | Booker et al. |
| 5,601,533 A | 2/1997 | Hancke et al. |
| 5,602,039 A | 2/1997 | Van den Engh |
| 5,602,349 A | 2/1997 | Van den Engh |
| 5,622,820 A | 4/1997 | Rossi |
| 5,641,457 A | 6/1997 | Vardanega et al. |
| 5,643,796 A | 7/1997 | Van den Engh et al. |
| 5,650,847 A | 7/1997 | Maltsev et al. |
| 5,660,997 A | 8/1997 | Spaulding |
| 5,663,048 A | 9/1997 | Winkfein et al. |
| 5,672,880 A | 9/1997 | Kain |
| 5,675,401 A | 10/1997 | Wangler et al. |
| 5,684,575 A | 11/1997 | Steen |
| 5,687,727 A | 11/1997 | Kraus et al. |
| 5,690,895 A | 11/1997 | Matsumoto et al. |
| 5,691,133 A | 11/1997 | Critser et al. |
| 5,693,534 A | 12/1997 | Alak et al. |
| 5,700,692 A | 12/1997 | Sweet |
| 5,707,808 A | 1/1998 | Roslaniec et al. |
| 5,708,868 A | 1/1998 | Ishikawa |
| 5,726,364 A | 3/1998 | Van den Engh |
| 5,759,767 A | 6/1998 | Lakowicz et al. |
| 5,777,732 A | 7/1998 | Hanninen et al. |
| 5,780,230 A | 7/1998 | Li et al. |
| 5,786,560 A | 7/1998 | Tatah et al. |
| 5,793,485 A | 8/1998 | Gourley |
| 5,796,112 A | 8/1998 | Ichie |
| 5,804,436 A | 9/1998 | Okun et al. |
| 5,815,262 A | 9/1998 | Schrof et al. |
| 5,819,948 A | 10/1998 | Van den Engh |
| 5,824,269 A | 10/1998 | Kosaka et al. |

| | | |
|---|---|---|
| 5,835,262 A | 11/1998 | Iketaki et al. |
| 5,868,767 A | 2/1999 | Farley et al. |
| 5,873,254 A | 2/1999 | Arav |
| 5,876,942 A | 3/1999 | Cheng et al. |
| 5,880,457 A | 3/1999 | Tomiyama et al. |
| 5,888,730 A | 3/1999 | Gray et al. |
| 5,891,734 A | 4/1999 | Gill et al. |
| 5,895,764 A | 4/1999 | Sklar et al. |
| 5,895,922 A | 4/1999 | Ho |
| 5,899,848 A | 5/1999 | Haubrich |
| 5,912,257 A | 6/1999 | Prasad et al. |
| 5,916,144 A | 6/1999 | Prather et al. |
| 5,916,449 A | 6/1999 | Ellwart et al. |
| 5,919,621 A | 7/1999 | Brown |
| 5,985,216 A | 11/1999 | Rens et al. |
| 5,985,538 A | 11/1999 | Stachecki |
| 6,002,471 A | 12/1999 | Quake |
| 6,050,935 A | 4/2000 | Ranoux et al. |
| 6,071,689 A | 6/2000 | Seidel et al. |
| 6,087,352 A | 7/2000 | Trout |
| 6,117,068 A | 9/2000 | Gourley et al. |
| 6,119,465 A | 9/2000 | Mullens et al. |
| 6,133,044 A | 10/2000 | Van den Engh |
| 6,140,121 A | 10/2000 | Ellington et al. |
| 6,149,867 A | 11/2000 | Seidel et al. |
| 6,153,373 A | 11/2000 | Benjamin et al. |
| 6,154,276 A | 11/2000 | Mariella, Jr. |
| 6,175,409 B1 | 1/2001 | Nielsen et al. |
| 6,177,277 B1 | 1/2001 | Soini |
| 6,238,920 B1 | 5/2001 | Nagai et al. |
| 6,248,590 B1 | 6/2001 | Malachowski |
| 6,263,745 B1 | 7/2001 | Buchanan et al. |
| 6,283,920 B1 | 9/2001 | Eberle et al. |
| 6,357,307 B2 | 3/2002 | Buchanan et al. |
| 6,372,422 B1 | 4/2002 | Seidel et al. |
| 6,395,305 B1 | 5/2002 | Buhr et al. ............. 424/520 |
| 6,411,835 B1 | 6/2002 | Modell et al. |
| 6,463,314 B1 | 10/2002 | Haruna |
| 6,489,092 B1 | 12/2002 | Benjamin et al. |
| 6,524,860 B1 | 2/2003 | Seidel et al. |
| 6,528,802 B1 | 3/2003 | Koenig et al. |
| 6,534,308 B1 | 3/2003 | Palsson et al. |
| 6,537,829 B1 | 3/2003 | Zarling et al. |
| 6,577,387 B2 | 6/2003 | Ross, III et al. |
| 6,590,911 B1 | 7/2003 | Spinelli et al. |
| 6,604,435 B2 | 8/2003 | Buchanan et al. |
| 6,617,107 B1 | 9/2003 | Dean |
| 6,618,679 B2 | 9/2003 | Loehrlein et al. |
| 6,642,018 B1 | 11/2003 | Koller et al. |
| 6,667,830 B1 | 12/2003 | Iketaki et al. |
| 6,671,044 B2 | 12/2003 | Ortyn et al. |
| 6,673,095 B2 | 1/2004 | Nordquist |
| 6,704,313 B1 | 3/2004 | Duret et al. |
| 6,782,768 B2 | 8/2004 | Buchanan et al. |
| 6,819,411 B1 | 11/2004 | Sharpe et al. |
| 7,094,527 B2 | 8/2006 | Seidel et al. |
| 2002/0096123 A1 | 7/2002 | Whittier et al. |
| 2002/0113965 A1 | 8/2002 | Roche et al. |
| 2002/0119558 A1 | 8/2002 | Seidel et al. |
| 2002/0141902 A1 | 10/2002 | Asbury et al. |
| 2002/0186375 A1 | 12/2002 | Asbury et al. |
| 2003/0098421 A1 | 5/2003 | Ho |
| 2003/0129091 A1 | 7/2003 | Seidel et al. |
| 2003/0157475 A1 | 8/2003 | Schenk |
| 2003/0207461 A1 | 11/2003 | Bell et al. |
| 2003/0209059 A1 | 11/2003 | Kawano |
| 2004/0005582 A1 | 1/2004 | Shipwast |
| 2004/0031071 A1 | 2/2004 | Morris et al. |
| 2004/0049801 A1 | 3/2004 | Seidel |
| 2004/0053243 A1 | 3/2004 | Evans |
| 2004/0055030 A1 | 3/2004 | Maxwell et al. |
| 2004/0062685 A1 | 4/2004 | Norton et al. |
| 2004/0132001 A1 | 7/2004 | Seidel et al. |
| 2005/0003472 A1 | 1/2005 | Muhammad |
| 2005/0112541 A1 | 5/2005 | Durack |
| 2005/0214733 A1 | 9/2005 | Graham |
| 2005/0244805 A1 | 11/2005 | Ludwig et al. |
| 2005/0282245 A1 | 12/2005 | Ludwig et al. |

FOREIGN PATENT DOCUMENTS

| | | |
|---|---|---|
| DE | 69028526 | 2/1997 |
| DE | 195 49 015 C1 | 4/1997 |
| DE | 198 82 943.3 | 2/2001 |
| EP | 0025296 A2 | 3/1981 |
| EP | 0071538 A1 | 2/1983 |
| EP | 0160201 A2 | 11/1985 |
| EP | 0189702 A1 | 8/1986 |
| EP | 0288029 B1 | 4/1988 |
| EP | 0276166 A2 | 7/1988 |
| EP | A-0 366794 | 5/1990 |
| EP | 0461618 | 12/1991 |
| EP | 0468100 A1 | 1/1992 |
| EP | 0570102 A1 | 3/1993 |
| EP | 0 538 786 A | 4/1993 |
| EP | 606847 A2 | 7/1994 |
| EP | A-0 478155 | 1/1998 |
| EP | 0781985 A3 | 7/1998 |
| EP | 1250897 A1 | 10/2002 |
| EP | 1 403 633 A3 | 4/2004 |
| FR | 2574656 A1 | 6/1986 |
| FR | A-2 635453 | 2/1990 |
| FR | 2 647 668 A | 12/1990 |
| FR | 2699678 A1 | 6/1994 |
| GB | 1471019 | 4/1977 |
| GB | 0030480.1 | 1/2001 |
| JP | 61139747 (A) | 6/1986 |
| JP | 61159135 (A) | 7/1986 |
| JP | 2024535 | 1/1990 |
| JP | 4126064 (A) | 4/1992 |
| JP | 4126065 (A) | 4/1992 |
| JP | 4126066 (A) | 4/1992 |
| JP | 4126079 (A) | 4/1992 |
| JP | 4126080 (A) | 4/1992 |
| JP | 4126081 (A) | 4/1992 |
| SU | 1056008 | 11/1983 |
| SU | 1260778 A1 | 9/1986 |
| WO | WO 88/07198 | 9/1988 |
| WO | WO 90/13315 A1 | 11/1990 |
| WO | 93/17322 A1 | 9/1993 |
| WO | WO 96/12171 A2 | 4/1996 |
| WO | WO 96/31764 | 10/1996 |
| WO | WO 98/34094 A1 | 8/1998 |
| WO | WO 98/48259 | 10/1998 |
| WO | WO 99/05504 A2 | 2/1999 |
| WO | WO 99/33956 | 7/1999 |
| WO | WO 99/38883 A1 | 8/1999 |
| WO | WO 99/42810 A1 | 8/1999 |
| WO | WO 99/44037 A1 | 9/1999 |
| WO | WO 00/06193 A1 | 2/2000 |
| WO | WO 01/37655 A1 | 5/2001 |
| WO | WO 01/40765 A2 | 6/2001 |
| WO | WO 01/40765 A3 | 6/2001 |
| WO | WO 01/51612 A1 | 7/2001 |
| WO | WO 01/85913 A2 | 11/2001 |
| WO | WO 01/85913 A3 | 11/2001 |
| WO | WO 01/90295 A1 | 11/2001 |
| WO | WO 01/95815 A1 | 12/2001 |
| WO | WO 02/19943 A1 | 3/2002 |
| WO | WO 02/28311 A2 | 4/2002 |
| WO | WO 02/41906 A2 | 5/2002 |
| WO | WO 02/43486 A1 | 6/2002 |
| WO | WO 02/43574 A2 | 6/2002 |
| WO | WO 04/009237 A1 | 1/2004 |
| WO | WO 04/009237 A3 | 1/2004 |
| WO | WO 04/012837 A1 | 2/2004 |

| | | |
|---|---|---|
| WO | WO 04/012837 A3 | 2/2004 |
| WO | WO 04/017041 A1 | 2/2004 |
| WO | WO 04/017041 A3 | 2/2004 |
| WO | WO 04/024227 A1 | 3/2004 |
| WO | WO 2004/059282 A2 | 7/2004 |
| WO | WO 2004/003697 A2 | 10/2004 |
| WO | WO 2004/087177 | 10/2004 |
| WO | WO 2004/088283 A2 | 10/2004 |
| WO | WO 04/104178 A1 | 12/2004 |
| WO | WO 2004/104178 A3 | 12/2004 |
| WO | WO 2005/094852 A2 | 10/2005 |
| WO | WO 2005/095590 A2 | 10/2005 |
| WO | WO 2005/095960 A1 | 10/2005 |
| WO | 2006012597 A2 | 2/2006 |

OTHER PUBLICATIONS

Graham, J. K. and Hammerstedt, R. H.; "Differential Effects of Butylated Hydroxytoluene Analogs on Bull Sperm Subjected to Cold-Induced Membrane Stress," *Cryobiology*, 29:106-117 (1992).

Hammerstedt, et al, "Cryopreservation of Mammalian Sperm: What We Ask Them to Survive," *Journal of Andrology*, 11:1:73-88 (1990).

Maxwell, W. M. C. and Johnson, L. A.; "Chlortetracycline Analysis of Boar Spermatozoa After Incubation, Flow Cytometric Sorting, Cooling, or Cryopreservation," *Molecular Reproduction and Development*, 46:408-418 (1997).

Polge, et al, "Revival of Spermatozoa After Vitrification and Dehydration at Low Temperatures," *Nature*, 164:666 (1949).

Pursel, et al, "Effect of Orvus ES Paste on Acrosome Morphology, Motility and Fertilizing Capacity of Frozen-Thawed Boar Sperm," *Journal of Animal Science*, 47:1:198-202 (1978).

Salisbury, et al, *Physiology of Reproduction and Artificial Insemination of Cattle*, 2nd Ed., San Francisco: W. H. Freeman, 442-554 (1978).

Schenk, et al, "Cryopreservation of Flow-Sorted Bovine Spermatozoa," *Theriogenology*, 52:1375-1391 (1999).

Seidel, et al, "Insemination of Heifers and Sexed Sperm," *Theriogenology*, 52:1407-1420 (1999).

Watson, "Recent Developments and Concepts in the Cryopreservation of Spermatozoa and the Assessment of Their Post-Thawing Function," *Reprod. Fertil. Dev.*, 7:871-891 (1995).

Database WPI, Section CH, Week 199920; Derwent Publications Ltd., London, GB; Class B04, AN 1999-229816; XP002164167 & BR 9704313 (Alves EW, De Resende Matta M F et al (Apr. 6, 1999—Abstract).

DeLeeuw, F E et al. "Effects Of Various Cryoprotective Agents And Membrane-Stabilizing Compounds On Bull Sperm Membrane Integrity After Cooling And Freezing," (1993), *Cryobiology, US, Academic Press Inc.*; vol. 30, No. 1, pp. 32-44, XP002089949; ISSN: 0011-2240.

Stap, J. et al, "Improving The Resolution Of Cryopreserved X- and Y-Sperm During DNA Flow Cytometric Analysis" (1998), *J. Anim. Sci.*; vol. 76, pp. 1896-1902, XP000985715.

Australian Application No. 17552/01; Examiner's report dated Oct. 21, 2003.

Australian Application No. 17552/01; Notice of Acceptance dated Jul. 29, 2005.

Chinese Application No. 00818617.0, Notification of First Office Action.

European Application No. 05001937.1, European Search Report dated May 4, 2005.

European Appliction No. 00980567.9, European examination report dated Jun. 23, 2003.

European Appliction No. 00980567.9, Certificate of Grant of Patent dated Feb. 2, 2005.

European Appliction No. 00980567.9;Opposition filed by European Union Parliament Nov. 5, 2005 (This documents in filed herewith in German. A translation will be forwarded to the Examiner once it is received).

European Appliction No. 00980567.9; Opposition filed by Greenpeace Nov. 2, 2005 (This document in filed herewith in German. A translation will be forwarded to the Examiner once it is received).

European Appliction No. 00980567.9; Opposition filed by Monsanto Oct. 31, 2005.

New Zealand Application No. 519078, Examination Report dated Jul. 3, 2004.

New Zealand Application No. 519078, Letters Patent No. 519078 dated Nov. 22, 2000.

New Zealand Application No. 530441, Examination Report dated Jan. 8, 2004.

Brink, Z et al. A reliable procedure for superovulating cattle to obtain zygotes and early emryos for microinjection, Theriogenology vol. 41, p. 168, (1994).

Spectra-Physics, The Solid State Laser Company, Vanguard 350-HMD 355, User's Manual, Dec. 2002.

Photon, Inc. Light MeasuringSolutions, NanoScan for High-powered beam Applications, 2005.

Fluorescense Lifetime Systems, www.picoquant.com, Jan. 28, 2005 pp. 2.

NCI ETI Branch, Flow CytometryCore Laboratory, http://home.ncifcrf.gov/ccr/flowcore/ndyag.htm, pp. 5, May 11, 2004.

NCI ETI Branch, Flow CytometryCore Laboratory, http://home.ncifcrf.gov/ccr/flowcore/lsrll.htm, pp. 14, May 11, 2004.

Saacke,R.G., Can Spermatozoa with abnormal heads gain access to the ovum in artificially inseminated super- and single-ovulating cattle?, Theriogenology 50:117-128. 1998.

Hawk, H.W., Gamete Transport in the Superovulated Cow. Theriogenology: Jan. 1998 vol. 29 No. 1 pp. 125-142.

Blecher, S.R., et al. A new approach to immunological sexing of sperm, Theriogenology, 59, pp. 1309-1321, 1999 vol.

Wheeler, M. B., et al. Application of sexed semen technology to in vitro embryo production in cattle, Theriogenology, vol. 65 (2006) 219-227.

Garverick, H. A., et al. mRNA and protein expression of P450 aromatase (AROM) and estrigen recepters (ER) α and β during early development of bovine fetal ovaries; The society for the study of reproduction 38th annual meeting Jul. 24-27, 2005; Abstract only.

Bodmer, M., et al., Fertility in heifers and cows after low does insemination with sex-sorted and non-sorted sperm under field conditions; Theriogenology, vol. 64, (2005) 1647-1655.

Schenk J. L., et al. Embryo production from superovulated cattle following insemination of sexed sperm, Theriogenology, 65 (2006) 299-307.

Garner, D. L., Flow cytometric sexing of mammalian sperm, Theriogenology, (2006) pp. 15.

Habermann F. A., et al., Validation of sperm sexing in the cattle (Bos taurus) by dual colour flourescence in situ hybridization; J Anim Breed Genet. Apr. 2005; 122 Suppl 1:22-7 (Abstract only).

Abdel-Ghaffar, A. E., et al., "Rabbit Semen Metabolism" in Rabbit Production in Hot Climates Baselga and Marai (eds); International Conference of Rabbit Production in Hot Climates 1994, p. 305-312.

Akhtar, S., et al., "Prevalence of Five Stereotypes of Bluetongue Virus in a Rambouillet Sheep Flock in Pakistan", Veterinary Record 136, p. 495. (1995).

Aldrich, S. L., et al., "Parturition and Periparturient Reproductive and Metabolic Hormone Concentration in Prenatally Androgenized Beef Heifers", J. Anim. Sci. 73:3712. (1995).

Amann, R. P. et al., "Issues Affecting Commercialization of Sexed Sperm" Therio. 52:1441. (1999).

Amann, R. P., et al. "Prospects For Sexing Mammalian Sperm," Animal Reproduction Laboratory College of Veterinary Medicine and Biomedical Sciences, Colorado State University. (1982).

Amann, R.P. "Fertilizing Potential Vitro of Semen from Young Beef Bulls Containing a High or Low Percentage of Sperm with a Proximal Droplet" Theriogenology 54: 1499-1515, 2000.

Amann, Rupert P. "Cryopreservation of Sperm" 1999, Encyclopedia of Reproduction 1:733-783.

American Meat and Science Association in Cooperation with National Livestock and Meat Board, "Research Guidelines for Cookery and Sensory Evaluation and Instrumental Tenderness Measurements for Fresh Meat". (1995).

Amoah, E. A. and Gelaye, S., "Biotechnological Advances in Goat Reproduction", J. Anim. Sci. 75(2): 578-585. (1996).

Anderson, V. K., et al., Intrauterine und tiefzervikale Insemination mit Gefriersperma bein Schat (Intrauterine and Deep Cervical Insemination With Frozen Semen in Sheep). Zuchthygiene 8:113-118. (1973).

Asbury, Charles A. "Fluorescence Spectra of DNA Dyes Measured in a Flow Cytometer," University of Washington Feb. 19, 1996.

Bagley, C. P. "Nutritional Management of Replacement Beef Heifers: a Review" J. Anim. Science 71:3155-3163. (1993).

Bailey, C. M. et al., "Nulliparous Versus Primiparous Crossbred Females for Beef", J. Anim. Sci. 69:1403. (1991).

Baker, R.D., et al., "Effect of Volume of Semen, Number of Sperm and Drugs on Transport of Sperm in Artificially Inseminated Gilts", J. Anim. Sci. 27:88-93. (1968).

Bakker Schut, Tom C. "A New Principle of Cell Sorting by Using Selective Electroportation in a Modified Flow Cytometry," University of Twente, Mar. 10, 1990.

Barnes, F. L. and Eyestone, W. H., "Early Cleavage and the Maternal Zygotic Transition in Bovine Embryos", Therio. vol. 33, No. 1, pp. 141-149. (1990).

Batellier, F. et al., "Advances in Cooled Semen Technology" Animal Reproduction Science 68 p. 181-190 (2001).

Becker, S.E. and Johnson, A. L. "Effects of Gonadotropin-Releasing Hormone Infused in a Pulsatile or Continuous Fashion on Serum Gonadotropin Concentrations and Ovulation in the Mare", J. Anim. Sci. 70:1208-1215. (1992).

Bedford, S. J. and Hinrichs, K., "The Effect of Insemination Volume on Pregnancy Rates of Pony Mares", Therio. 42:571-578. (1994).

Bellows, R. A., et al., "Cause and Effect Relationship Associated With Calving Difficulty and Calf Birth Weight", J. Anim. Sci. 33:407. (1971).

Berardinelli, J. G., et al., "Source of Progesterolle Prior to Puberty in Beef Heifers". J. Anim. Sci. 49:1276. (1979).

Berger, G. S. "Intratubal Insemination", Fertil. Steril. 48:328-330, (1987).

Bergfeld, E. G., et al., "Ovarian Follicular Development in Prepubertal Heifers is Influenced by Level of Dietary Energy Intake", Bio. of Repro. 51:1051. (1994).

Berry, B. W., et al., "Beef Carcass Maturity Indicators and Palatability Attributes", J. Anim. Sci. 38:507 (1974).

Beyhan, Z., et al., "Sexual Dimorphism in IVF Bovine Embryos Produced by Sperm Sorted by High Speed Flow Cytometry", abstr. Therio. 49(1): 359 (1998).

Beyhan, Z., Et Al., 1999 Sexual Dimorphism In IVM-IVF Bovine Embryos Produced from X and Y Chromosome-Bearing Spermatozoa Sorted By High Speed Flow Cytometry. Theriogenology. 52: 35-48.

BigosBigos, Martin "Nine Color Eleven Parameter Immunophenotyping Using Three Laser Flow Cytometry," Stanford University Dec. 22, 1998.

Bioxcell, Bovine Sperm Preservation, Advertisement Jun. 28, 2005.

Bond, J., et al., "Growth and Carcass Traits of Open Beef Heifers Versus Beef Heifers That Have Calved", Nutrition Reports International 34:621. 1986.

Borini et al. Cryopreservation of Mature Oocytes: The use of a trypsin inhibitor enhances fertilization and obtained embryos rates, Fertil. Steril. (1997), vol. 68 (Suppl.).

Boucque, C. V., et al., "Beef-Production With Maiden and Once-Calved Heifers", Livestock Prod. Sci. 7:121. 1980.

Bourdon, R. M. and J. S. Brinks. "Simulated Efficiency of Range Beef-Production III. Culling Strategies and Nontraditional Management-Systems", J. Anim. Sci. 65:963. 1987.

Bracher, V. and Allen, W.R., "Videoendoscopic Examination of the Mare's Uterus: I. Findings in Normal Fertile Mares", Equine Veterinary Journal, vol. 24, p. 274-278. 1992.

Branscomb, D. P., The LLNL high-speed sorter: Design features, operational characteristics, and bioloical utility, Cyometry, 6:290-301 (1985).

Braselton, W. E. and McShan, W. H., "Purification and Properties of Follicle Stimulating and Luteinizing Hormones From Horse Pituitary Glands" Arch. Biochem. Biophys. 139:45-48. 1970.

Braun, J. et al, "Effect of Different Protein Supplements on Motility and Plasma Membrane Integrity of Frozen-Thawed Stallion Spermatozoa", Cryobiology (1995) 32:487-492.

Brethour, J. R. and Jaeger, J. R., "The Single Calf Heifer System", Kansas Agric. Sta. Rep. of Progress 570. 1989.

Brinsko, S.P. et al., "Artificial Insemination and Preservation of Semen." Veterinary Clinics of North America:Equine Practice vol. 8 No. 1 Apr. 1992 pp. 205-218.

Bristol, F. "Breeding Behavior of a Stallion at Pasture With 20 Mares in Synchronized Oestrus" J. Reprod. Fertil. Suppl. 32:71. 1982.

Brookes, A. J. and O'Byrne, M., "Use of Cow-Heifers in Beef Production" J. of the Royal Agricultural Society of England 126:30. 1965.

Buchanan, B. R., et al, "Insemination of Mares with Low Numbers of Either Unsexed or Sexed Spermatozoa", Therio. vol. 53, p. 1333-1344. 2000.

Buchanan, B.R. "Pregnancy Rates in Mares Following a Single Insemination with a Low Number of Spermatozoa into the Tip of the Uterine Horn" Theriogenology p. 395.

Burns, P.D. and Spitzer, J.C., "Influence of Biostimulation on Reproduction in Postpartum Beef-Cows", J. Anim. Sci. 70:358. 1992.

Burwash, L. D., et al., "Relationship of Duration of Estrus to Pregnancy Rate in Normally Cycling, Non Lactating Mares" J.A.V.M.A. 165:714-716. 1974.

Byerley, D. J., et al., "Pregnancy Rates of Beef Heifers Bred Either on Puberal or Third Estrus". J Anim. Sci. 65:645. 1987.

Caslick, E. A., "The Vulva and the Vulvo-Vaginal Orifice and its Relation to Genital Health of the Thoroughbred Mare", Cornell Veterinarian, vol. 27, p. 178-187. 1937.

Catt, et al., "Assessment of Ram and Boar Spermatozoa During Cell-Sorting by Flow Cytometry", Reproduction Dom Animal, vol. 32, pp. 251-258. 1997.

Catt, S. L., et al., "Birth of a Male Lamb Derived from an In Vitro Matured Oocyte Fertilized by Intracytoplasmic Injection of a Single Presumptive Male Sperm" , Veterinary Record 139, p. 494-495. 1996.

Cave-Penney, Tony, "Sexed Semen Offers Faster Genetic Gain", Farming News, Livestock Supplement, Feb. 1997, p. 28.

Celestron; Telescope Basics: www.celestron.com/tb-2ref/htm; 4 pages.

Cf. Milovanov V.K. "Biology of reproduction and artificial insemination of animals", Moscow, Izdatelstvo Selskokhoziastvennoi Literatury, 1962, pp. 392-619.

Chandler, J. E., "Videomicroscopic Comparison of Bull Sperm and Leukocyte Chromosone Areas as Related to Gender", J Dairy Sci 73, p. 2129-2135. 1990.

Chandler, J. E., et al, "Bovine Spermatozoal Head Size Variation and Evaluation of a Separation Technique Based on this Size", Therio. 52, p. 1021-1034. 1999.

Chen, S.H. "Effects of Oocyte Activation and Treatment of Spermatozoa on Embryonic Development Following Intracytoplasmic Sperm Injection in Cattle" Theriogenology 48: 1265-1273, 1997.

Chen, Y. et al., Survival of Bull Spermatozoa Seeded and Frozen at Different Rates in Egg Yolk-Tris and Whole Milk Extenders, 1993 J Dairy Sci 76:1028-1034.

Chin, W. W. and Boime, I. 1990. In Glycoprotein Hormones. Serona Symp. Norwell, MA. pp. 19-20.

Choi, Y.H. "Development Cappacity of Equine Oocytes Matured and Cultured in Equine Trophoblast-Conditioned Media" Theriogenoogy 56: 320-339, 2001.

Chung, Y. G., et al. "Artificial insemination of Superovulated Heifers With 600,000 Sexed Sperm". J Anim. Sci. Suppl. 1. 836:215. 1998 abstr.

Clement, F., et al., "Which Insemination Fertilizes When Several Successive Inseminations are Performed Before Ovulation" 7th Int. Symp. Eq. Repro. 151. 1998 abstr.

Cran et al. The predetermination of embryonic sex using flow cytometrically separated X and Y spermatozoa, Human Reproduction Update 1996, vol. 2, No. 4 pp. 355-363.

Cran, D. G., et al, "Production of Lambs by Low Dose Intrauterine Insemination With Flow Cytometrically Sorted and Unsorted Semen", Therio. p. 267. 1997.

Cran, D. G., et al., "Sex Preselected in Cattle: A Field Trial", Veterinary Record 136, 1995, p. 495-496.

Cran, D. G., et al., "Production of Bovine Calves Following Separation of X- and Y-Chromosome Bearing Sperm and In Vitro Fertilization", Vet. Rec. 132:40-41. 1993.

Cran, D. G., et al., "The Predetermination of Embryonic Sex Using Flow Cytometrically Separated X and Y Spermatozoa" Human Reproduction Update 1996, vol. 2 (4) p. 355-63.

Crowley, J. P. "The facts of Once-Bred Heifer Production" School of Agric., Univ. of Aberdeen, Scotland. 1973.

Cui, K. et al, "X Larger than Y", Nature 366, p. 177-118, 1993.

Cui, K., "Size Differences Between Human X and Y Spermatozoa and Prefertilization Diagnosis", Molecular Human Reproduction, vol. 3, No. 1, pp. 61-67. 1997.

Curran, S. "Fetal Gender Determination" in *Equine Diagnostic Ultrasonography* 1st ed. Rantanen, N.W. and McKinnon A.O. (eds.) Williams and Williams, 1998, p. 165-69.

da Silva, Coutinho M.A.."Effect of time of oocyte collection and site of insemination on oocyte transfer in mares." Animal Reproduction and Biotechnology Laboratory, Colorado State Uniuversity, Fort Collins Journal of Animal Science 2002. 80:1275-1279.

Dako Cytomation, "MoFlo® Sorters" http://www.dakocytomation.us/prod_productrelatedinformation?url=gprod_moflo_index.htm one page, printed Jun. 26, 2003.

Day, B. N., et al. Birth of Piglets Preselected for Gender Following In Vitro Fertilization of In Vitro Matured Pig Oocytes by X and Y Bearing Spermatozoa Sorted by High Speed Flow Cytometry. Therio. 49(1): 360. 1998 abstr.

Dean, P.N., et al. "Hydrodynamic Orientation of Spermatozoa Heads for Flow Cytometry". Biophys. J. 23:7-13. 1978.

Demick, D.S., et al. "Effect of Cooling, Storage, Glycerization and Spermatozoal Numbers on Equine Fertility" J. Anim. Sci. 43:633-637. 1976.

DenDaas, J. H. G., et al. "The relationship between the number of spermatozoa inseminated and the reproductive efficiency of dairy bulls" J Dairy Sci. 81: 1714-1723. 1998.

Denham, A. "In-vitro studies on Sandhill Range Forage as Related to Cattle Preference", M.S. Thesis. Colorado State University. 1965.

Denk, Winfried. "Two-Photon Molecular Excitation in Laser-Scanning Microscopy," Handbook of Biological Confocal Microscopy. 1995.

Deutscher, G. H. "Extending Interval From Seventeen to Nineteen Days in the Melengestrol Acetate-Prostaglandin Estrous Synchronization Program for Heifers". The Professional Animal Scientist 16:164. 2000.

Dhali et al. Vitrification of Buffalo (Bubalus Bubalis)Oocytes, Embryo Theriogenology vol. 53, pp. 1295-1303 (2000).

*Diagnostic Products Corporation, "Coat-A-Count"* http://www.Progesterone.com. 1998.

Dikeman, M. E. "Cattle Production Systems to Meet Future Consumer Demands" J. Anim. Sci. 59:1631, 1984.

Dinnyes, A., et al., "Timing of the First Cleavage Post-Insemination Affects Cryosurvival of In Vitro-produced Bovine Blastocysts", Molec. Reprod. Develop. 53, p. 318-324. 1999.

Dippert, K.D. "Fertilization Rates in Superovulated and Spontaneously Ovulating Mares" Theriogenology 41: 1411-1423, 1994.

Donaldson, L. E., "Effect of Insemination Regiman on Embryo Production in Superovulated Cows", The Veterinary Record, Jul. 13, p. 35-37, 1985.

Donoghue, A.M., et al. "Timing of Ovulation after Gonadotropin Induction and its Importance to Successful Intrauterine Insemination in the Tiger (Panthera tigris)" J. Reprod. Fertil. 107:53-58. 1996.

Douglas, R. H., "Review of Induction of Superovulation and Embryo Transfer in the Equine" Therio. 11:33-46. 1979.

Douglas, R. H., et al. "Induction of Ovulation and Multiple Ovulation on Seasonally-Anovulatory Mares with Equine Pituitary Fractions." Therio. 2(6): 133-142. 1974.

Doyle, S. P., et al. "Artificial Insemination of Lactating Angus Cows with Sexed Semen". Proc. Western Sect. Am. Soc. Anim. Sci. 50:203. 1999.

Dresser D.W. et at. Analysis of DNAcontent ofLiving Spermatozoa Using Flow Cytometry Technique Journal of Reproduction and Fertility, 1993, vol. 98, pp. 357-365.

Duchamp, G., et al. "Alternative Solutions to hCG Induction of Ovulation in the Mare" J. Reprod. Fertil. Suppl. 35:221-228. 1987.

Evans, M. J. and Irvine, C. H. G. "Induction of Follicular Development, Maturation and Ovulation by Gonadotropin Releasing Hormone Administration to Acyclic Mares" Bio. Reprod. 16:452-462. 1977.

Ferrell, C. L. Effects of Post-Weaning Rate of Gain on Onset of Puberty and Productive Performance of Heifers of Different Breeds. J. Anim. Sci. 55:1272. 1982.

Ferrell, C. L. and T. G. Jenkins. "Energy-Utilization by Mature, Nonpregnant, Nonlactating Cows of Different Types" J. Anim. Sci. 58:234. 1984.

Field, R. A., et al., "Bone-Ossification and Carcass Characteristics of Wethers Given Silastic Implants Containing Estradiol", J. Anim. Sci. 68:3663-3668. 1990.

Field, R. et al., "Growth, Carcass, and Tenderness Characterisitcs of Virgin, Spayed, and Single-Calf Heifers", J. Anim. Sci. 74:2178. 1996.

Fitzgerald, B. P., et al. "Effect of Constant Administration of a Gonadotropin-Releasing Hormone Agonist on Reproductive Activity in Mares: Preliminary Evidence on Suppression of Ovulation During the Breeding Season." Am. J. Vet. Res. 54:1746-1751. 1993.

Fluharty, F. L., et al., "Effects of Age at Weaning and Diet on Growth of Calves", Ohio State University Dept. of Animal Scieneces. 1966 Ohio Agri. Res. And Den. Circular, 156:29 1966.

Foote, et al. Motility and Fertility of Bull Sperm Frozen-Thawed Differently in Egg Yolk and Milk Extenders Containing Detergent, 1987 J Dairy Sci 70:2642-2647.

Foulkes, J. A., et al. "Artificial Insemination of Cattle Using Varying Numbers of Spermatozoa." Vet. Rec. 101:205. 1977.

Francon, M. and Yamamoto, T., "Un Noveau es tres simple dispositif interferentiel applicable as microscope" Optica Acta 9, p. 395-408. 1962.

Fugger, E. F. "Clinical Experience with Flow Cytometric Separation of Human X- and Y- Chromosome Bearing Sperm", Therio. vol. 52, pp. 1435-1440. 1999.

Fuller, Robert R. "Characterizing Submicron Vesicles With Wavelength-Resolved Fluorescence in Flow Cytometry," University of Illinois, May 13, 1996.

Fulwyler, M. J. "Electronic Separation of Biological Cells by Volume." Sicence. 150:910. 1965.

Fulwyler, M. J. "Hydrodynamic Orientation of Cells." J of Histochem. and Cytochem. 25:781-783.

Garner, D. L., et al. "Quantification of the X and Y Chromosome-Bearing Spermatozoa of Domestic Animals by Flow Cytometry." Biol. Reprod. 28:312-321. 1983.

Ginther, O. J., "Sexual Behavior Following Introduction of a Stallion into a Group of Mares" Therio. vol. 19 (6) Jun. 1983.

Ginther, O. J., "Some Factors Whcih Alter Estrus Cycle in Mares." J. Anim. Sci. 33:1158. 1971 abstr.

Ginther, O. J., Reproductive Biology of the Mare. (2nd Ed.) Equiservices, Cross Plains, WI. 1992.

Gledhill, B. L. "Gender Preselection: Historical, Technical and Ethical Perspective." Semen Reprod. Endocrinol. 6:385-395. 1988.

Gombe, S. and Hansel, W. "Plasma Luteinizing Hormone (LH) and Progesterone Levels in Heifers on Restricted Energy Intakes." J. Anim. Sci. 37:728. 1973.

Goppert-Mayer,"Uber Elementarakte mit zwei Quantensprungen Von Maria Copper -Mayer".

Gottlinger et al., "Operation of a Flow Cytometer", Flow Cytometry and Cell Sorting, A. Radbruch (Ed.), 1992, pp. 7-23.

Gourley, D. D. and Riese, R. L. "Laparoscopic Artificial Insemination in Sheep." Vet. Clin. N. Amer: Food Anim. Prac. 6(3): 615-633 (1990).

Graham, J. Analysis of Stallion semen and its Relation to Fertility. Abstract.

Graham, James K., "Effect of Cholesterol-Loaded Cyclodextrins in Semen Extenders", Proceedings of the 19th Technical Conference on Artificial Insemination & Reproduction, 2003, pp. 91-95.

Gravert, H. O., "Genetic Aspects of Early Calving." In: J.C. Taylor (Ed.) *The Early Calving of Heifers and Its Impact on Beef Production*. 59 (1975).

Gregory, K. E., et al., "Characterization of Biological Types of Cattle—Cycle III: II Growth Rate and Puberty in Females" J. Anim. Sci. 49:461 (1979).

Grimes, I. F, and T. B. Turner. "Early Weaning of Fall Born Calves II. Post Weaning Performance of Early and Normal☐Weaned Calves". I. Prod. Agric. 4:168 (1991).

Grondahl, C., et al, "In Vitro Production of Equine Embryos", Biology of Reproduction, Monograph Series I, p. 299-307 (1995).

Guillou, F. and Combarnous, Y. "Purification of Equine Gonadotropins and Comparative Study of Their Acid-Dissociation and Receptor-Binding Specificity." Biochemica Et Biophysica Acta 755:229-236 (1983).

Gurnsey, M. P., and Johnson, L.A., "Recent Improvements in Efficiency of Flow Cytometric Sorting of X and Y-Chromosome Bering Sperm of Domestic Animals: a Review" New Zealand Society of Animal Protection, three pages (1998).

Hall, J. B., et al., "Effect of Age and Pattern of Gain on Induction of Puberty with a Progestin in Beef Heifers." J. Anim. Sci. 75:1606 (1997).

Hamamatsu Photonics K.K. Electronic Tube Center, Photomultiplier Tubes, Brochure Dec. 1997.

Hamamatsu, "*Photomultiplier Tubes*," http://www.optics.org/hamamatsu/pmt.html. Printed on Apr. 15, 2000 4.

Hamamatsu, "*Technical Information, Optical Detector Selection: A Delicate Balancing Act*", web pages, http://www.optics.org/hamamatsu/photodiode.html, printed on Apr. 15, 2000, 6 pages total.

Hamano, K., et al., "Gender Preselection in Cattle with Intracytoplasmically Injected, Flow Cytometrically Sorted Sperm Heads", Biology of Reproduction 60, p. 1194-1197 (1999).

Harrison, L.A., et al., "Comparison of HCG, Buserelin and Luprostiol for Induction of Ovulation in Cycling Mares." Eq. Vet. Sci. 3:163-166 (1991).

Harte, F. J. "System of Production of Beef From Once Calved Heifers." In: J.C. Taylor (Ed.) *The Early Calving of Heifers and its Impact on Beef Production*. 123 (1975).

Hawk, H. W., et al., "Fertilization Rates in Superovulating Cows After Deposition of Semen on the Infundibulum Near the Uterotubal Junction or After Insemination with High Numbers of Sperm", XP-002103478, Therio. vol. 29, No. 5, p. 1131-1142 (1988).

Hermesmeyer, G. N., et al. "Effects of Prenatal Androgenization and Implantation on the Performance and Carcass Composition of Lactating Heifers in the Single-Calf Heifer System." The Professional Animal Scientist 15:173. 1999.

Hermesmeyer, G.N., et al. Effects of Lactation and Prenatal Androgenization on the Performance, Carcass Composition, and Longissimus muscle sensory characteristics of heifers in the single-calf heifer system. The Professional Animal Scientist 15: 14-23.

Herweijer, Hans. "High-Speed Photodamage Cell Selection Uing Bromodeoxyuridine/Hoechst 33342 Photosensitized Cell Killing," Sep. 23, 1987.

Herzenberg, Leonard A. "Fluorescence-activated Cell Sorting," pp. 108-117.

Hilton, G. G., et al., "An Evaluation of Current and Alternative Systems for Quality Grading Carcasses of Mature Slaughter Cows." J. Anim. Sci. 76:2094. 1998.

Ho, L., et al., "Influence of Gender, Breed and Age on Maturity Characteristics of Sheep." J. Anim. Sci. 67:2460-2470. 1989.

Hofferer, S., et al. "Induction of Ovulation and Superovulation in Mares Using Equine LH and FSH Separated by Hydrophobic Interaction Chromatography." J. Reprod. Fertil. 98:597-602. 1993.

Hohenboken, W. D. "Applications of sexed semen in cattle production." Therio. 52:1421. 1999.

Hollinshead F. K. et al. "Production of lambs of predetermined sex after the insemination of ewes with low numbers of frozen-thawed sorted X- or Y- Chromosome-bearing spermatozoa", Reprod. Fertil. And Develop. 2002, vol. 14, pp. 503-508.

Hollinshead F. K. et al. "Sex-Sorting and Re-cryopreservation of Frozen-Thawed Ram Sperm for In Vitro Embryo Production" Theriogenology, vol. 59. (2003) pp. 209.

Hollinshead, F.K. et al. "In vitro and in vivo assessment of functional capacity of flow cytometrically sorted ram spermatozoa after freezing and thawing." Reprod. Fertil. And Develop. 2003. vol. 15, pp. 351-359.

Holtan, D. W., et al., "Estrus, Ovulation and Conception Following Synchronization With Progesterone, Prostaglandin F2a and Human Chorionic Gonadotropin in Pony Mares." J. Anim. Sci. 44:431-437. 1977.

Horan, Paul K. "Quantitative Single Cell Ana,lysis and Sorting, Rapid Analysis and sorting of cells is emerging as an important new technology in research and medicine."

Householder, D. D., et al. "Effect of Extender, Number of Spermatozoa and hCG on Equine Fertility." J. Equine Vet. Sci. 1:9-13. 1981.

Howard, J. G., et al., "Comparative Semen Cryopreservation in Ferrets (Mustela putorious furo) and Pregnancies After Laparoscopic Intrauterine Insemination With Frozen-Thawed Spermatozoa." J. Reprod. Fertil. 92:109-118. 1991.

Howard, J. G., et al., "Sensitivity to Exogenous Gonadotropins for Ovulation and Laparoscopic Artificial Insemination in the Cheetah and Clouded Leopard." Biol. Reprod. 56:1059-1068. 1997.

Hunter, R. H. F. "Transport and Storage of Spermatozoa in the Female Tract." Proc 4th Int. Congress Anim. Repro. and A. I. 9:227-233. 1980.

Hyland, J. H., et al., "Gonadotropin Releasing Hormone (GnRH) Delivered by Continuous Infusion Induces Fertile Estrus in Mares During Seasonal Acycility" Proceedings of the Annual Convention of the American Association of Equine Practitioners (34th) 989, p. 181-190.

IMV Technologies, Protocol of Bioxcell with Fresh Semen, 1 page, 2000.

IMV Technologies, Protocol of Bioxcell with Frozen Semen, 2 pages, 2000.

Irvine, C H. G. and Alexander, S. L. "GnRH" Chapter 4 in Equine Reproduction, McKinnon and Voss eds. Lea and Febiger. Philadelphia, London. p. 37. (1993).

Iwazumi, Y., et al., "Superovulation Using CIDR in Holstein Cows" J. of Reprod. Dev. vol. 40 (3) 1994, pp. 259-66.

Jafar, et al., "Sex Selection in Mammals: A Review", Therio. vol. 46, p. 191-200. (1996).

Jakubiczka, S. et al. "A Bovine Homologue of the Human TSPY Gene." Genomics. 1993, vol. 17, No. 3, pp. 732-735.

Jarriage, R. "Age of Cows at First Calving in France." In: J.C. Taylor (Ed.) *The Early Calving of Heifers and its Impact on Beef Production*. 10. (1975).

Jasko, D. J., et al., "Effect of Insemination Volume and Concentration of Spermotozoa on Embryo Recovery in Mares", Therio. 37:1233-1239, (1992).

Jasko, D. J., et al., "Pregnancy Rates Utilizing Fresh, Cooled and Frozen-Thawed Stallion Semen", American Association of Equine Practitioners 38th Annual Convention Proceedings, 1992, p. 649-60.

Johnson, A. L. "Pulsatile Administration of Gonadotropin Releasing Hormone Advances Ovulation in Cycling Mares", Biol. Reprod. 35:1123-1130. (1986).

Johnson, A. L., et al. "Use of Gonadotropin-Releasing Hormone (GnRH) Treatment to Induce Multiple Ovulations in the Anestrous Mare" Eq. Vet. Sci. 8:130-134, (1988).

Johnson, L. A., et al. The Beltsville Sperm Sexing Technology: High-speed sperm sorting gives improved sperm output for In Vitro fertiliation and Al, Journal of Animal Science, vol. 77, Suppl 2/J, Dairy Sci. vol. 82, Suppl. 2/1999 pp. 213-220.

Johnson, L.A., "Flow Cytometric Determination of Spermatozoa Sex Ratio in Semen Purportedly Enriched for X or Y Bearing Spermatozoa", Therio. 29:265 abstr.

Johnson, L.A., "Gender Preselection in Domestic Animals Using Flow Cytometrically Sorted Sperm" J. Anim. Sci. (Suppl I) 70:8-18. (1992).

Johnson, L.A., "The Safety of Sperm Selection by Flow Cytometry" Ham. Reprod. 9(5): 758. (1994).
Johnson, L.A., "Advances in Gender Preselection in Swine" Journal of Reproduction and Fertility Supplement, vol. 52, p. 255-266 (1997).
Johnson, L.A., "Gender Preselection in Humans? Flow Cytometric Separation of X and Y Spermatozoa for the Prevention of X-Linked Diseases" Human Reproduction vol. 8 No. 10, p. 1733-1739 (1993).
Johnson, L.A., "Gender Preselection in Mammals: An Overview", Deutsch. Tierarztl. Wschr, vol. 103, p. 288-291 (1996).
Johnson, L.A., "Isolation of X- and Y-Bearing Spermatozoa for Sex Preselection." Oxford Reviews of Reproductive Biology. Ed. H. H. Charlton. Oxford University Press. 303-326. (1994).
Johnson, L.A., "Sex Preselection by Flow Cytometric Separation of X and Y Chromosome Bearing Spermatozoa Based on DNA Difference: a Review." Reprod. Fertil. Dev. 7:893-903. (1995).
Johnson, L.A., "Sex Preselection in Rabbits: Live Births from X and Y Sperm Separated by DNA and Cell Sorting", Biology of Reproduction 41, pp. 199-203 (1989).
Johnson, L.A., "Sex Preselection in Swine: Altered Sex Rations on Offspring Following Surgical Insemination of Flow Sorted X- and Y- Bearing Sperm", Reproduction in Domestic Animals, vol. 26, pp. 309-314 (1991).
Johnson, L.A., "Sex Preselection in Swine: Flow Cytometric Sorting of X- and Y- Chromosome Bearing Sperm to Produce Offspring", Boar Semen Preservation IV, p. 107-114. (2000).
Johnson, L.A., "Successful Gender Preselection in Farm Animals", Agricultural Biotechnology, p. 439-452. (1998).
Johnson, L.A., et al. "Sex Preselection: High-speed Flow Cytometric Sorting of X and Y Sperm for Maximum Efficiency", Therio. vol. 52, p. 1323-1341 (1999).
Johnson, L.A., et al., "Enhanced Flow Cytometric Sorting of Mammalian X and Y Sperm: High Speed sorting and Orienting Nozzle for Artificial Insemination", Therio. 49(1): 361 (1988) abstr.
Johnson, L.A., et al., "Flow Sorting of X and Y Chromosome-Bearing Spermatozoa into Two Populations", Gamete Res. 16:203-212. (1987).
Johnson, L.A., et al., "Improved Flow Sorting Resolution of X- and Y-Chromosome Bearing Viable Sperm Separation Using Dual Staining and Dead Cell Gating" Cytometry 17 (suppl 7): 83, (1994).
Johnson, L.A., et al., "Flow Cytometry of X- and Y-Chromosome Bearing Sperm for DNA Using an Improved Preparation Method and Staining with Hoechst 33342." Gamete Research 17: 203-212. (1987).
Johnson, L.A., et al., "Modification of a Laser-Based Flow Cytometer for High-Resolution DNA Analysis of Mammalian Spermatozoa" Cytometry 7, pp. 268-273 (1986).
Joseph, R. L. "Carcass composition and meat quality in once calved heifers." In: J.C. Taylor (Ed.) *The Early Calving of Heifers and its Impact on Beef Production.* 143. (1975).
Joseph, R. L. and J. P. Crowley. "Meat Quality of Once-Calved Heifers." Irish J. of Agric. Research 10:281. (1971).
Kachel, V., et al., "Uniform Lateral Orientation, Caused by Flow Forces, of Flat Particles in Flow-Through Systems", The Journal of Histochemistry and Cytochemistry, vol. 25, No. 7, pp. 774-780. (1997).
Kanayama, K., et al., "Pregnancy by Means of Tubal Insemination and Subsequent Spontaneous Pregnancy in Rabbits." J. Int. Med. Res. 20:401-405. (1992).
Karabinus, et al., "Effects of Egg Yolk-Citrate and Milk Extenders on Chromatin Structured Vability of Cryopreserved Bull Sperm", Journal of Dairy Science, vol. 74, No. 11, pp. 3836-3848. (1999).
Keeling, P. "A Modeling Study of Once-Bred Heifer Beef Production." Proceedings of the New Zealand Society of Animal Production. 51. (1991).
Kilicarslan, M. R., et al., "Effect of GnRH and hCG on Ovulation and Pregnancy in Mares." Vet. Rec. 139:119-120. (1996).
Kinder, J. E., et al. "Endocrine Basis for Puberty in Heifers and Ewes." J. Repro. and Fertility, p. 393. (1995).
Kinder, J. E., et al., "Endocrine Regulation of Puberty in Cows and Ewes." J. Repro. and Fertility, Suppl. 34:167. (1987).
Kinoshita, Shuichi. "Spectroscopic Properties of Fluorescein in Living Lymphocytes," Osaka Uinversity Aug. 7, 1986.

Klindt, J. and J. D. Crouse. "Effect of Ovariectomy and Ovariectomy with Ovarian Autotransplantation on Feedlot Performance and Carcass Characteristics of Heifers." J. Anim. Sci. 68:3481. (1990).
Klosterman, E. W. and C. F. Parker. "Effect of Size, Breed and Sex Upon Feed Efficiency in Beef Cattle." North Central Regional Research Publication 235, Ohio Agric. Research and Development Center 1090:3. (1976).
Kniffen, D. M., et al., "Effects of Long-Term Estrogen Implants in Beef Heifers." J. Anim. Sci. 77:2886. (1999).
Kobata, Akira, "Structures and Functions of the Sugar Chains of Human Chorionic Gonadotropin", in *Glycoprotein Hormones* Chin, W.W. and Boime, I., eds. Serono Symposia, Norwell, MA. p. 19-20. 1990.
Koch, R. M., et al., "Characterization of Biological Types of Cattle -Cycle-II .3." Carcass Composition, Quality and Palatability. J. Anim. Sci. 49:448. (1919).
Kommisrud E., et al. "Comparison of Two Processing Systems for Bull Semen with Regard to Post-Thaw Motility and Nonreturn Rates." Theriogenology, vol. 45, 1996, pp. 1515-1521.
Lapin, D. R. and Ginther, O. J. "Induction of Ovulation and Multiple Ovulations in Seasonally Anovulatory and Ovulatory Mares with an Equine Pituitary Extract." J. Anim. Sci. 44:834-842. (1977).
Laster, D. B., "Factors Affecting Dystocia and Effects of Dystocia on Subsequent Reproduction in Beef-Cattle." J. Anim. Sci. 36:695. (1973).
Lawrenz, R. "Preliminary Results of Non-Surgical Intrauterine Insemination of Sheep With Thawed Frozen Semen." J S Afr. Vet. Assoc. 56(2):61-63. (1985).
Levinson, G., et al., "DNA-based X-Enriched Sperm Separation as an Adjunct to Preimplantation Genetic Testing for the Preparation of X-linked Disease." Mol. Human Reprod. 10:979-982. (1995).
Lightwave Electronics, "Xcyte," www.LightwaveElecronics.com.
Lindsey, A. C., et al., "Low Dose Insemination of Mares Using Non-Sorted and Sex-Sorted Sperm" Animal Reproduction Science 68 p. 279-89 (2001).
Lindsey, A., et al., "Hysteroscopic Insemination of Mares with Nonfrozen Low-dose Unsexed or Sex-Sorted Spermatozoa", pp. 1-15 currently unpublished.
Linge, F. "Faltforsok med djupfrost sperma (Field Trials With Frozen Sperm)." Farskotsel. 52:12-13. (1972).
Liu, Z, et al. "Survival of Bull Sperm Frozen at Different rates in Media Varying in Osmolarity." Cryobiology, vol. 27, 1998, pp. 219-230.
Lonergan, P., et al., "Effect of Time Interval from Insemination to First Cleavage on the Development of Bovine Embryos In Vitro and In Vivo", Therio. p. 326 (1999).
Long, C.R., et al., "In Vitro Production of Porcine Embryos From Semen Sorted for Sex With a High Speed Cell Sorter: Comparison of Two Fertilization Media." Therio. 49(1): 363 (1998) abstr.
Loy, R. G. and Hughes, J.P. "The Effects of Human Chorionic Gonadotropin on Ovulation, Length of Estrus, and Fertility in the Mare." Cornell Vet. 56:41-50 (1965).
Lu, K. H. et al., "In Vitro Fertilization of Bovine Oocytes with Flow-Cytometrically Sorted and Unsorted Sperm from Different Bulls" Therio. abstr.
Lu, K. H., et al., "In Vitro Fertilization with Flow-Cytometrically-Sorted Bovine Sperm", Therio 52, p. 1393-1405. (1999).
Lynch, I. M., et al., "Influence of timing of gain on growth and reproductive performance of beef replacement heifers." J. Anim. Sci. 75:1715. (1997).
Macmillan, K. L. and Day, A.M., "Prostaglandin F2a: A Fertility Drug In Dairy Cattle?", Animal Research Station, Private Bag, Hamilton, New Zealand, Therio. vol. 18, No. 3, p. 245-253 (1982).
Manni, Jeff. "To-Photon Excitation Expands the Capabilities of Laser-Scanning Microscopy,".
Manning, S.T., et al., "Development of Hysteroscopic Insemination of the Uterine Tube in the Mare", Proceedings of the Annual Meeting of the Society for Theriogenology, 1998, p. 84-85.
Martin, A. H., et al., "Characteristics of Youthful Beef Carcasses in Relation to Weight, Age and Sex. III. Meat Quality Attributes." Canadian J. Anim. Sci. 51:305. (1971).

Martin, L. C., et al., "Genetic-effects on Beef Heifer Puberty and Subsequent Reproduction." J. Anim. Sci. 70:4006. (1992).

Martinez, E. A., et al., "Successful Low-Dose Insemination by a Fiberoptic Endoscope Technique in the Sow", Proceedings Annual Conference of the International Embryo Transfer Society, Netherlands, Therio. vol. 53 p. 201, Jan. 2000.

Matsuda, Y. and Tobari, I. "Chromosomal Analysis in Mouse Eggs Fertilized In Vitro With Sperm Exposed to Ultraviolet Light (UV) and Methyl and Ethyl Methanesulfonate (MMS and EMS)." Mutat. Res. 198:131-144. (1988).

Matulis, R. J., "Growth and carcass characteristics of cull cows after different times-on-feed." J. Anim. Sci. 65:669. (1987).

Mauleon, P. "Recent research related to the physiology of puberty." In: J. C. Taylor (ed.) *The Early Calving of Heifers and its Impact on Beef Production*. (1975).

Maxwell, W. M. C., et al., "Fertility of Superovulated Ewes After Intrauterine or Oviductal Insemination with Low Numbers of Fresh or Frozen-Thawed Spermatozoa." Reprod. Fertil. Dev. 5:57-63. (1993).

Maxwell, W. M. C., et al., "The Relationship Between Membrane Status and Fertility of Boar Spermatozoa After Flow Cytometric Sorting in the Presence or Absence of Seminal Plasma" Reprod. Fertil. Dev. vol. 10 p. 433-40 (1998).

Maxwell, W. M. C., et al., "Viability and Membrane Integrity of Spermazota after Dilution and Flow Cytometric Sorting in the Presence or Absence of Seminal Plasma." Reprod. Fertil. Dev. 8:1165-78. (1997).

McCormick, R. J. "The Flexibility of the Collagen Compartment of Muscle." Meat Sci. 36:79. (1994).

McCue, P.M. "Superovulation" Vet. Clin. N. Amer. Eq. Prac. 12:1-11. (1996).

McCue, P.M., et al., "Oviductal insemination in the mare." 7th Internat. Symp. Eq. Reprod. 133 (1997) abstr.

McDonald, L. E. "Hormones of the Pituitary Gland." Veterinary Pharmacology and Therapeutics. 6th ed. Edited by N. H. Booth and L. E. McDonald. Ames, Iowa State Univ. Press. p. 590 (1988).

McKenna, T. et al., "Nonreturn Rates of Dairy Cattle Following Uterine Body or Cornual Insemination." J. Dairy Sci. 73:1179-1783 (1990).

McKinnon, A.O. and Voss, J. L. *Equine Reproduction*. Lea and Febiger. Philadelphia, London (1993).

McKinnon, A.O., et al., "Predictable Ovulation in Mares Treated With an Implant of the GnRH Analogue Deslorelin." Eq. Vet. J. 25:321-323. (1993).

McKinnon, A.O., et al., "Repeated Use of a GnRH Analogue Deslorelin (Ovuplant) for Hastening Ovulation in the Transitional Mare." Eq. Vt. J. 29:153-155. (1996).

McLeod, John H., "The Axicon: A New type of Optical Element", Journal of the Optical Society of America, vol. 44 No. 8, Aug. 1954, Eastman Kodak Company, Hawk-Eye Works, Rochester, New York.

McNutt, T. L. et al., "Flow Cytometric Sorting of Sperm: Influence on Fertilization and Embryo/Fetal Developement in the Rabbit", Molecular Reproduction and Developement, vol. 43, p. 261-267 (1996).

Meilgaard, M., et al., "Sensor Evaluation Techniques." CRC Press Inc., Boca Raton, FL. (1991).

Meinert, C., et al., "Advancing the Time of Ovulation in the Mare With a Short-Term Implant Releasing the GnRH Analogue Deslorelin", Equine Veterinary Journal, 25, p. 65-68 (1993).

Melamed et al, "An Historical Review of the Development of Flow Cytometers and Sorters", 1979, pp. 3-9.

Mendes Jr., J.O.B. "Effect of heparin on cleavage rates and embryo production with four bovine sperm prepration protocols" Theriogenology 60 (2003) 331-340.

Menke,E. A Volume Activated Cell Sorter Journal of Histo chemistry and Cyto Chemistry, 1977, vol. 25,No. 7, pp. 796-803.

Merton, J., et al., "Effect of Flow Cytometrically Sorted Frozen/Thawed Semen on Success Rate of In Vitro Bovine Embryo Production", Therio. 47, p. 295. (1997).

Metezeau P. et al. Improvement of Flow Cytometry Analysis and Sorting of Bull Spermatozoa by Optical Monitoring of Cell Orientation as Evaluated by DAN Specific Probing Molecular Reproduction and Development, 1991, vol. 30 pp. 250-257.

Meyers, P. J., et al., "Use of the GnRH Analogue, Deslorelin Acetate, in a Slow Release Implant to Accelerate Ovulation in Oestrous Mares." Vet. Rec. 140:249-252. (1997).

Michaels, C., "Beef A. I. Facilities That Work", Proc. Fifth N.A.A.B Tech. Conf. A. I. Reprod. Columbia, MO. pp. 20-22.

Michel, T. H., et al., "Efficacy of Human Gonadotropin and Gonadotropin Releasing Hormone for Hastening Ovulation in Thoroughbred Mares." Eq. Vet. J. 6:438-442. (1986).

Miller, S. J. "Artificial Breeding Techniques in Sheep." Morrow, D.A. (ed): Current Therapy in Therio 2. Philadelphia, WB Saunders. (1986).

Mirskaja, L. M. and Petropavloskii, V.V. "The Reduction of Normal Duration of Heat in the Mare by the Administration of Prolan." Probl. Zivotn. Anim. Breed. Abstr. 5:387. (1937).

Moe, P. W., "Energetics of Body Tissue Mobilization." J. of Dairy Sci. 54:548.

Molinia, F. C., et al., "Successful Fertilization After Superovulation and Laparoscopic Intrauterine Insemination of the Brushtail Possum Trichosurus vulpecula, and Tammar Wallaby, Macropus eugenii." Reprod. Fertil. 112:9-17. (1998).

Moran, C., et al., "Puberty in Heifers -a Review." Animal Reproduction Sci. 18:167. (1989).

Moran, D. M. et al., "Determination of Temperature and Cooling Rate Which Induce Cold Shock in Stallion Spermatozoa", Therio. vol. 38 p. 999-1012 (1992).

Morcom, C. B. and Dukelow, W.R. "A Research Technique for the Oviductal Insemination of Pigs Using Laparoscopy." Lab. Anim. Sci. p. 1030-1031. (1980).

Morgan, J. B., et al., "National Beef Tenderness Survey." J. Anim. Sci. 69: 3274. (1991).

Morris, L. H., et al., "Hysteroscopic Insemination of Small Numbers of Spermatozoa at the Uterotubal Junction of Preovulatory Mares", Journal of Reproduction and Fertility, vol. 118, pp. 95-100 (2000).

Morris, S. T., et al., "Biological efficiency: How relevant is this concept to beef cows in a mixed livestock seasonal pasture supply context?" Proceedings of the New Zealand Society of Animal Production 54:333. (1994).

Moseley, W. M., et al., "Relationship of Growth and Puberty in Beef Heifers Fed Monensin" J. Anim. Sci. vol. 55 No. 2 p. 357-62 (1982).

Mount, D. E. "Fibrous and Non-fibrous Carbohydrate Supplementation to Ruminants Grazing Forage From Small Grain Crops." M.S. Thesis. Abstr. Colorado State University. (2000).

Muller, W. and Gautier, F. "Interactions of Heteroaromatic Compounds with Nucleic Acids." Euro. J Biochem. 54:358. (1975).

Mullis, K. B. and F. A. Faloona, "Specific Synthesis of DNA in Vitro Via a Polymerase-Catalyzed Chain Reaction" Methods in Enzymology vol. 155 p. 335-350 (1978).

Munne, S. "Flow Cytometry Separation if X and Y Spermatozoa Could be Detrimental to Human Embryos", Hum. Reprod. 9(5): 758 (1994).

Myers, S. E., "Performance and Carcass Traits of Early-Weaned Steers Receiving Either a Pasture Growing Period or a Finishing Diet at Weaning." J. Anim. Sci. 77:311. (1999).

Myers, S. E., et al., "Comparison of Three Weaning Ages on Cow-Calf Performance and Steer Carcass Traits." J. Anim. Sci. 77:323. (1999).

Myers, S. E., et al., "Production Systems Comparing Early Weaning to Normal Weaning With or Without Creep Feeding for Beef Steers." J. Anim. Sci. 77:300. (1999).

Nix, J. P., et al., "Serum Testosterone Concentration, Efficiency of Estrus Detection and Libido Expression in Androgenized Beef Cows." Therio. 49: 1195. (1998).

Nowshari, et al., "Superovulation of Goats with Purified pFSH Supplemented with Defined Amounts of pLH", Therio. vol. 43, p. 797-802 (1995).

NRC. "Nutrient Requirements for Beef Cattle." National Academy of Sci. National Research Council, Washington, DC. (1996).

O'Brien, Justine K. et al., "Preliminary Developments of Sperm Sorting Technology in Non-human Primates", Biology of Reproduction 2001(Su;;I. 1) 64:158.

Olive, M.D., "Detection of Enterotoxigenic *Escherichia coli* after Polymerase Chain Reaction Amplification with a Tehrmostable DNA Polymerase", J of Clinical Microbiology, Feb. 1989 p. 261-265.

Olson, S.E. and Seidel, G. E. Jr., "Reduced Oxygen Tension and EDTA improve Bovine Zygote Development in a Chemically Defined Medium", J. of Anim. Sci. 78, pp. 152-157. (2000).

Owen, J. B. "The Maiden Female-A Means of Increasing Meat Production." Proc. Symp. On the Use of Once Bred Heifers and Gilts. (1973).

Ozhin F.V. et al. Artificial insemination of farm animals. Moscow, Izdatelstvo Selskokhozyaastvennoi Literatury, 1961, pp. 350-361 and pp. 380-393.

Pace, M. M. and Sullivan, J. J. "Effect of Timing of Insemination, Numbers of Spermatozoa and Extender Components on Pregnancy Rates in Mares Inseminated with Frozen Stallion Semen." J. Reprod. Fertil. Suppl. 23:115-121.

Parrish, J. J., et al., "Capacitation of Bovine Sperm by Heparin", Department of Meat and Animal Science, Biology of Reproduction 38, p. 1171-1180 (1988).

Patterson, D. J., et al., "Estrus Synchronization with an Oral Progestogen Prior to Superovulation of Postpartum Beef Cows" Therio. 48, 1025-33 (1997).

Peippo, J., et al., "Sex Diagnosis of Equine Preimplantation Embryos Using the Polymerase Chain Reaction", Therio. vol. 44:619-627 (1995).

Penfold, L.M.et al., "Comparative Motility of X and Y Chromosome-Bearing Bovine Sperm Separated on the Basis of DNA Content", Mol. Reprod. And Develop. 1998, vol. 50,pp. 323-327.

Perry, E. J., "Historical Background" The Artificial Insemination of Farm Animals. 4th ed. E. J. Perry (ed.) New Brunswick, Rutgers University Press, pp. 3-12. (1968).

Petersen, G. A., et al, "Cow and Calf Performance and Economic-Considerations of Early Weaning of Fall-Born Beef Claves", J. Anim. Sci., 64:15, pp. 15-22. (1987).

Petit, M. "Early Calving in Suckling Herds." In: J.C. Taylor (ed.) *The Early Calving of Heifers and its Impact on Beef Production*. p. 157-176. (1975).

Picket B.W., et al., "Livestock Production Science," 1998.

Pickett, B. W, et al., "Factors Influencing the Fertility of Stallion Spermatozoa in an A. I. Program." Proc. 8th International Congress Anim. Reprod. A. I. Krakow, Poland. 4:1049-1052. (1976).

Pickett, B. W., et al., "Effect of Seminal Extenders on Equine Fertility." J. Anim. Sci. 40:1136-1143. (1975).

Pickett, B. W., et al., "Influence of Seminal Additives and Packaging Systems on Fertility of Bovine Spermatozoa." J. Anim. Sci. Suppl. II. 47:12. (1978).

Pickett, B. W., et al., "Management of the Mare for Maximum Reproductive Efficency." CSU Anim. Repro. Lab. Bull. No. 06. Fort Collins CO. (1989).

Pickett, B. W., et al., "Procedures for Preparation, Collection, Evaluation and Insemination of Stallion Semen." CSU Exp. Sta. Artira. Reprod. Lab. Gen. Series Bull. 935. (1973).

Pickett, B. W., et al., "Recent Developments in Artificial Insemination in Horses", Livestock Production Science, 40, p. 31-36 (1994).

Pickett, B. W., et al., "The Effect of Extenders, Spermatozoal Numbers and Rectal Palpation on Equine Fertility." Proc. Fifth N.A.A.B Tech. Conf. A. I. Reprod. Columbia, MO. pp. 20-22. (1974).

Pinkel et al., "Flow Chambers and Sample Handling", Flow Cytometry: Instrumentation and Data Analysis, Van Dilla et al. (Eds.), 1985, pp. 77-128.

Pinkel, D., et al, "Flow Cytometric Determination of the Proportions of X- and Y- Chromosome-Bearing Sperm in Samples of Purportedly Separated Bull Sperm", J. of Anim. Sci., vol. 60, p. 1303-1307 (1998).

Pinkel, D., et al., "High Resolution DNA Content Measurements of Mammalian Sperm", Cytometry 3:1-9. (1982).

Pinkel, D., et al., "Sex Preselection in Mammals? Separation of Sperm Bearing the Y and "O" Chromosomes in the Vole Microtus Oregoni", Science vol. 218 p. 904 (1982).

Piston, D.W. "Three-dimensionally resolved NAD(P)H cellular metabolic redox imaging of the in situ cornea with two-photon excitation laser scanning microscopy," Journal of Microscopy, vol. 178, Nov. 29, 1994.

Polge, E. J., "Historical Perspective of AI: Commercial Methods of Producing Sex Specific Semen, IVF Procedures", Proceedings of the 16th Technical Conference on Artificial Insemination & Reproduction, Cambridge, England, pp. 7-11. (1996).

Preza, C. et al, "Determination of Direction-Independent Optical Path-Length Distribution of Cells Using Rotational-Diversity Transmitted-Light Differential Interference Contrast (DIC) Images", Presented at the Multidimensional Microscopy: Image Acquisition and Processing V, p. 1-11 (1998).

Prokofiev M.I. Regoulyatsia Razmnozhenia Selskokhozyastvennykh Zhivotnykh, Leningrad, NAOUKA Publishing House, 1983, pp. 181-195.

Province, C.A., et al., Cooling Rates, Storage, Temperatures and Fetility of Extended Equine Spermatozoa Therio. vol. 23 (6) p. 925-934, Jun. 1985.

Purvis, H. T. and J. C. Whittier. "Effects of Ionophore Feeding and Anthelmintic Administration on Age and Weight at Puberty in Spring-Born Beef Heifers." J. Anim. Sci. 74:736-744. (1996).

Randel, R. D. "Nutrition and Postpartum Rebreeding in Cattle." J. Anim. Sci. 68:853. (1990).

Rath, D., et al., "Low Dose Insemination Technique in the Pig", Boar Semen Preservation IV, p. 115 118. (2000).

Rath, D., et al., "Production of Piglets Preselected for Sex Following in Vitro Fertilization with X and Y Chromosome-Bearing Spermatozoa Sorted by Flow Cytometry", Therio. 47, p. 795-800 (1997).

Rathi, R. et al., "Evaluation of In Vitro Capacitation of Stallion Spermatoza", Biology of Reproduction 2001, vol. 65, pp. 462-470.

Recktenwald, Diether. "Cell Separation Methods and Applications," New York 1997.

Reiling, B.A., et al., "Effect of Prenatal Androgenization on Performance, Location, and Carcass and Sensory Traits on Heifers in Single Calf Heifer System", J. Anim. Sci., 1995, 73: 986, p. 986-992.

Reiling, B.A., et al., "Effects of Prenatal Androgenization and Lactation on Adipose Tissue Metabolism in Finishing Single-Calf Heifers" J. Anim. Sci. vol. 75 p. 1504-1512 (1997).

Reiling, B.A., et al., "Effects of prenatal Androgenization, Melengestrol Acetate, and Synovex-H on Feedlot Performance, Carcass, and Sensory Traits of Once-Calved Heifers" J. Anim. Sci. vol. 74 p. 2043-51 (199).

Rens W., et al Slit-scan flow cytometry for consistent high resdolution DNA analysis of X- and Y- chromosome bearing sperm, Cytometry 25:191-199 (1996).

Rens, W., et al., "A Novel Nozzle for More Efficient Sperm Orientation to Improve Sorting Efficiency of X and Y Chromosome-Bearing Sperm", Technical Notes, Cytometry 33, p. 476-481 (1998).

Rens, W., et al., "Improved Flow Cytometric Sorting of X- and Y-Chromosome Bearing Sperm: Substantial Increase in Yield of Sexed Semen", Molecular Reproduction and Development, p. 50-56(1999).

Rieger, D., et al, "The Relationship Between the Time of First Cleavage of Fertilized Cattle Oocytes and Their Development to the Blastocyst Stage", Therio. 1999, p. 190.

Rigby, S. L., et al., "Pregnancy Rates in Mares Following Hysterscopic or Rectally-Guided Utero-Tubal insemination with Low Sperm Numbers" Abstracts/Animal Reproduction Science vol. 68 p. 331-333 (2001).

Riggs, B.A. "Integration of Early Weaning and Use of Sexed Semen in a Single-Calf Heifer System to Increase Value of Non-Replacement Heifers" MS Thesis, Colorado State University, Spring 2000.

Ritar, A. and Ball, A., "Fertility of Young Cashmere Goats After Laparoscopic Insemination." J. Agr. Sci. 117: p. 271-273. (1991).

Roberts, J. R., Veterinary Obstetrics and Genital Diseases. Ithaca, New York. p. 740-749. (1971).

Romero-Arredondo, A. "Effects of Bovine Folicular Fluid on Maturation of Bovine Oocytes" Theriogenology 41: 383-394, 1994.

Romero-Arrendondo, A. "Effects of Follicular Fluid dring In Vitro Maturation of Bovine Oocytes on In Vitro Fertilization and Early Embryonic Developement" Biology of Reproduction 55, 1012-1016 1996.

Romita, A. "Some Considerations on the Beef Situation in Italy." In: J.C. Taylor (ed.) *The Early Calving of Heifers and its Impact on Beef Production*. 23. (1975).

Roser, J. F., et al., "Reproductive Efficiency in Mares With Anti-hCG Antibodies." Proc 9th Int. Congr. Anim. Repro. and A. I. 4:627 (1980) abstr.

Roth, T. L., et al., "Effects of Equine Chorionic Gonadotropin, Human Chorionic Gonadotropin, and Laparoscopic Artificial Insemination on Embryo, Endocrine, and Luteal Characteristics in the Domestic Cat." Bio. Reprod. 57:165-171 (1997).

Roux, M., et al., "Early Calving Heifers Versus Maiden Heifers for Beef-Production from Dairy herds. I. The Effects of Genotype (Friesian and Carloads x Friesian) and Two Feeding Levels in the Rearing Period on Growth and Carcass Quality." Livestock Prod. Sci. 16:1 (1987).

Rowley, H. S., et al., "Effect of Insemination Volume on Embryo Recovery in Mares." J. Equine Vet. Sci. 10:298-300 (1990).

Roy, J. H., "Rearing Dairy-Herd Replacements." Journal of the Society Of Dairy Technology 31:73-79 (1978).

Rutter, L. M., et al., "Effect of Abomasal Infusion of Propionate on the GnRH-Induced Luteinizing Hormone Release in Prepuberal Heifers." J. Anim. Sci. 56:1167 (1983).

Salamon, S., *Artificial Insemination of Sheep*, Chippendale, New South Whales. Publicity Press. p. 83-84 (1976).

Schenk, J. L, et al., "Imminent Commercialization of Sexed Bovine Sperm", Proceedings, The Range Beef Cow Symposium XVL, p. 89-96 (1999).

Schenk, J. L. "Applying Semen Sexing Technology to the AI Industry", Proceedings of the 18th Technical Conference on Artificial insemination & Reproduction, 2000.

Schiewe, M. C., et al., "Transferable Embryo Recovery Rates Following Different Insemination Schedules in Superovulated Beef Cattle" Therio. 28 (4) Oct. 1997, pp. 395-406.

Schillo, K. K., et al, "Effects of Nutrition and Season on the Onset of Puberty in the Beef Heifer." J. Anim. Sci. 70:3994 (1992).

Schmid, R. L., et al, "Fertilization with Sexed Equine Spermatozoa Using Intracytoplasmic Sperm Injection and Oviductal Insemination", 7th International Symposium On Equine Reproduction, pp. 139 (1998) abstr.

Schnell, T. D., et al, "Performance, Carcass, and Palatability Traits for Cull Cows Fed High-Energy Concentrate Diets for 0, 14, 28, 42, or 56 days." J. Anim. Sci. 75:1195. (1997).

Schoonmaker, J. P., et al., "Effects of Age at Weaning and Implant Strategy on Growth of Steer Calves." J. Anim. Sci. (Suppl. II) 76:71. (1998) abstr.

Scmid, R. L., et al. Effects of follicular fluid or progesterone on *in vitro* maturation of equine oocytes before intracytoplasmic sperm injection with non-sorted and sex-sorted spermatozoa, Journal of Reproduction and Fertility 56:519-525, 2000.

Seidel, G. E. Jr et al., "Current of Sexing Mammalian Spermatozoa," Society for Reproduction and fertility, pp. 733-743, 2002.

Seidel, G. E. Jr. "Cryopreservation of Equine Embryos" Veterinary Clinics of North America: Equine Practice vol. 12, No. 1, Apr. 1996.

Seidel, G. E. Jr. "Sexing Bovine Sperm" The AABP Proceedings—vol. 34.

Seidel, G. E. Jr. Sexing mammalian spermatozoa and embryos-state of the art Journal of Reproduction and Fertility Supp 54, 477-487 1999.

Seidel, G. E. Jr. "Uterine Horn Insemination of Heifers With Very Low Numbers of Nonfrozen and Sexed Spermatozoa", Atlantic Breeders Cooperative, Therio. 48: pp. 1255-1264, (1997).

Seidel, G. E. Jr., "Use of Sexed Bovine Sperm for In Vitro Fertilization and Superovulation", Animal Reproduction and Biotech Lab, CSU, Proceedings of the 2000 CETA/ACTE Convention, Charlottetown, Prince Edward Island, Aug. 2000, pp. 22-24.

Seidel, G. E. Jr., "Artificial Insemination With X-and Y-Bearing Bovine Sperm", Animal Reproduction and Biotechnology Laboratory, Colorado State University, (1996).

Seidel, G. E. Jr., "Commercilizing Repreductive Biotechnology—The Approach used by XY, Inc.," Theriogenology, p. 5, 1999.

Seidel, G. E. Jr., "Fertility of Bulls on the Edge of the Dose-Response Curve for Numbers of Sperm per Inseminate"; Proceedings of the 17th Technical comference on Artificial Insemination & Reproduction, 1998.

Seidel, G. E. Jr., "Status of Sexing Semen for Beef Cattle", Texas A & M University 45th Annual Beef Cattle Short Course and Trade Show Proceedings, Aug. 9-11, p. III24-III27, (1999).

Seidel, G. E. Jr., Economics of Selecting for Sex: The Most Important Genetic Trait, Theriogenology 59, (2003), pp. 585-598.

Seidel, G. E. Jr., et al, "Insemination Of Heifers With Very Low Numbers Of Frozen Spermatozoa", CSU, Atlantic Breeders Cooperative, Lancaster, PA, DUO Dairy, Loveland, CO, Jul. (1996).

Seidel, G. E. Jr., et al, "Insemination of Holstein Heifers With Very Low Numbers Of Unfrozen Spermatozoa", CSU, Atlantic Breeders Cooperative, (1995).

Seidel, G. E. Jr., et al, "Sexing Mammalian Sperm—Overview", Therio. 52: 1267-1272, (1999).

Seidel, G. E. Jr., et al., "Artificial Insemination of Heifers with Cooled, Unfrozen Sexed Semen", Therio, vol. 49 pp. 365 (1998) abstr.

Seidel, G. E. Jr., et al., "Insemination of Heifers with Sexed Frozen or Sexed Liquid Semen." Therio. 51. (in press) (1999) abstr.

Sell, R. S., et al., "Single-calf Heifer Profitability Compared to Other North Dakota Beef Production Systems."0 Department of Ag. Eco., North Dakota State University, Ag. Econ. Rpt. 20.

Senger, P. L., et al., "Influence of Cornual Insemination on Conception in Dairy Cattle." J Anim. Sci. 66:3010-3016. (1988).

Shabpareh, V. "Methods for Collecting and Maturing Equine Oocytes in Vitro" Theriogenology 40: 1161-1175, 1993.

Shackelford, S. D., et al, "Effects of Slaughter Age on Meat Tenderness and USDA Carcass Maturity Scores of Beef Females." J. Anim. Sci. 73:3304. (1995).

Shapiro, Howard M. MD., PC. "Practical Flow Cytometry Third Edition," New York 1994.

Sharpe, J.C., et al., "A New Optical Configuration for Flow Cytometric Sorting of Aspherical Cells" Horticulture and Food Research Institute of New Zealand Ltd., Hamilton, New Zealand (PNS) Nov. 2, 1997 ABSTRACT.

Sharpe, Johnathan, Thesis; "An Introduction of Flow Cytometry", Ch. 2-2.2, 1997.

Sharpe, Johnathan, Thesis; "Gender Preselection-Principle Scientific Options," Ch. 3.4-3.4.8, 1997.

Sharpe, Johnathan, Thesis; "Sperm Sexing using Flow Cytometry," Ch. 3.5-3.5.8, 1997.

Sharpe, Johnathan, Thesis; "Sperm Sexing-Method of Johnson et al," Ch. 3.6-4.3.4, 1997.

Shelton, J. N. and Moore, N.W. "The Response of the Ewe to Pregnant Serum Mare Gonadotropin and to Horse Anterior Pituitary Extract." J. Reprod. Fertil. 14:175-177. (1967).

Shilova, A. V., et al., "The Use of Human Chorionic Gonadotropin for Ovulation Date Regulation in Mares." VIIIth Int. Congress On Anim. Repro. and A. I. 204-208. (1976).

Shorthose, W. R. and P. V. Harris. "Effect of Animal Age on the Tenderness of Selected Beef Muscles." J. Food Sci. 55:1- (1990).

Silbermann, M., "Hormones and Cartilage. Cartilage: Development, Differentiation, and Growth." pp. 327-368. Academic Press, Inc. (1983).

Simon, M., "The Effect of Management Option on the Performance of Pregnant Feedlot Heifers." M.S. Thesis. Kansas State University. (1983).

Skogen-Hagenson, M. J. et al; "A High Efficiency Flow Cytometer," The Journal of Histochemistry and Cytochemistry, vol. 25, No. 7, pp. 784-789, 1977, USA.

Smith, G. C., et al, "USDA Maturity Indexes and Palatability of Beef Rib Staeks." J. of Food Quality 11:1. (1988).

Smith, G. C., et al., "Relationship of USDA Maturity Groups to Palatability of Cooked Beef." J. of Food Sci. 47:1100. (1982).

Smith, R. L., et al, Influence of Percent Egg Yolk during Cooling and Freezing on Survival of Bovine.

Solsberry G.U., Van-Denmark N.L., Theory and practice of artificial cow insemination in USA, Moscow, KOLOS Publishing House, 1966, p. 346.

Spectra Physics, The Solid State Laser Company, "Vanguard 4 Watts of UV from a Quasi-CW, All Solid State Laser," http://www.splasers.com/products/isl_products/vangaurd.html three pages, printed Nov. 14, 2002.

Spectra-Physics Products, "Fcbar" http://www.splasers.com/products/oem_products/ov_fcbar.html two pages printed Nov. 14, 2002.

Spectra-Physics, The Solid State Laser Company, Vanguard 2000-HDM 532, www.spectra-physics.com.

Spectra-Physics, The Solid State Laser Company, Vanguard 350-HDM 355, www.spectra-physics.com.

Squires, E. L, et al., "Effect of Dose of GnRH Analog on Ovulation in Mares." Therio. 41:757-769. (1994).

Squires, E. L., "Simultaneous Analysis of Multiple Sperm Attributes by Flow Cytometry", Diagnostic Techniques and Assisted Reproductive Technology, The Veterinary Clinics of North America, Equine Practice, vol. 12, No. 1, p. 127-130 (1996).

Squires, E. L., "Early Embryonic Loss" Equine Diagnostic Ultrasonography, first ed., Rantanen & McKinnon. Williams and Wilkins, Baltimore, Maryland, p. 157-163 (1998).

Squires, E. L., et al, "Cooled and Frozen Stallion Semen", Bulletin No. 9, Colorado State University, Ft. Collins, CO. (1999).

Squires, E.L., "Procedures for Handling Frozen Equine Semen for Maximum Reproductive Efficiency", pp. 1, 39-41, 81-89.

Staigmiller, R.B. "Superovulation of Cattle with Equine Pituitary Extract and Porcine FSH" Theriogenology 37: 1091-1099 1992.

Steel, N. L., "Cost Effectiveness of Utilizing Sexed-Semen in a Commercial Beef Cow Operation", MS Thesis, Colorado State University, Summer 1998.

Steinkamp: "Flow Cytometry" vol. 55, No. 9, Sep. 1984 pp. 1375-1400, New York Review of Scientific Instruments Abstract Only.

Stellflug, J. N., "Plasma Estrogens in Periparturient Cow." Therio 10:269. (1978).

Stevenson, J. S., et al., "Detection of Estrus by Visual Observation and Radiotelemetry in Peripubertal, Estrus-Synchronized Beef Heifers." J. Anim. Sci. 74:729. (1996).

Story, C. E., et al., "Age of Calf at Weaning of Spring-Calving Beef Cows and the Effect on Cow and Calf Performance and Production Economics." J. Anim. Sci. 78:1403. (2000).

Stovel R.T. A Means for Orienting Flat Cells in flow systems Biophysical Journal, 1978, vol. 23, pp. 1-5.

Sullivan, J. J., et al., "Duration of Estrus and Ovulation Time in Nonlactating Mares Given Human Chorionic Gonadotropin During Three Successive Estrous Periods." J.A.V.M.A. 162:895-898. (1973).

Sumner, A. T. and Robinson, J. A., "A Difference in Dry Mass Between the Heads of X and Y- Bearing Human Spermatozoa", J Reprod Fertil. 48, p. 9-15 (1976).

Swanson, E. W. "Future Research on Problems of Increasing Meat Production by Early Calving." In: J.C. Taylor (ed.) The Early Calving of Heifers and its Impact on Beef Production. (1975).

Swenson, S. L., et al., "PRRS Virus Infection in Boars: Isolation From Semen and Effect on Semen Quality" from the 1995 Research Investment Report, Iowa State University, Veterinary Clinical Sciences, Iowa State University.

Taljaard, T. L., et al., "The Effect of the Laparoscopic Insemination Technique on the Oestrus Cycle of the Ewe." J. South Afr. Vet. Assoc. 62(2): 60-61. (1991).

Tatum, J. D., et al., "Carcass Characteristics, Time on Feed and Cooked Beef Palatability Attributes." J. Anim. Sci. 50:833. (1980).

Taylor, C. S., "Efficiency of Food Utilization in Traditional and Sex-Controlled Systems of Beef Production", AFRC Animal Breeding Research Organization, West Mains Road, Edinburg EH9 3JQ, pp. 401-440.

Tervit, H.R., et al., "Successful Culture In Vitro of Sheep and Cattle Ova", Agricultural Research Council, Unit of Reprod. Physio. and Biochem., Univ of Cambridge, p. 493-497 (1972).

Thun, Rico, et al., Comparison of Biociphos-Plus® and TRIS-Egg Yolk Extender for Cryopreservation of Bull Semen; Theriogenology Symposium, Dec. 1999, vol. 52, #8.

Time-Bandwidth Products "GE—100—XHP", www.tbsp.com, 2 pages, Jan. 2002.

Unruh, J. A. "Effects of Endogenous and Exogenous Growth-Promoting Compounds on Carcass Composition, Meat Quality and Meat Nutritional-Value." J. Anim. Sci. 62:1441. (1986).

USDA "Official United States Standards for Grades of Carcass Beef." Agric, Marketing Serv., USDA, Washington, DC. (1997).

Van Dilla, Martin, "Overview of Flow Cytometry: Instrumentation and Data Analysis", Flow Cytometry: Instrumentation and Data Analysis, Van Dilla et al. (Eds.), 1985, pp. 1-8.

Van Munster, E. B., "Geslachtsbepaling met interferometrie", Derde prijs NtvN-prijsvraag voor pas-gepromoveerden 65/4, (Sex Determination with Interferometry) p. 95-98 (1999).

Van Munster, E. B., et al, "Difference in Sperm Head Volume as a Theoretical Basis for Sorting X & Y-Bearing Spermatozoa: Potential and Limitations", Therio 52, pp. 1281-1293 (1999).

Van Munster, E. B., et al, "Difference in Volume of X- and Y-chromosome Bearing Bovine Sperm Heads Matches Difference in DNA Content" Cytometry vol. 35 p. 125-128 (1999).

Van Munster, E. B., et al, "Measurement-Based Evaluation of Optical Path Length Distributions Reconstructed From Simulated Differential Interference Contrast Images", J of Microscopy 191, Pt. 2, p. 170-176 (1998).

Van Munster, E. B., et al, "Reconstruction of Optical Pathlength Distributions From Images Obtained by a Wide Field Differential Interference Contrast Microscope", J of Microscopy 188, Pt. 2, p. 149-157 (1997).

van Munsterm, E. B. Interferometry in flor to sort unstained X- and Y-Chromosome- Bearing Bull Spermatozoa, Cytometry 47:192-199 (2002).

Vazquez, J. J. et al., "Nonsurgical Uterotubal Insemination in the Mare", Proceedings of the 44th Annual Convention of the American Association of Equine Practitioners, vol. 44, pp. 68-69 (1998).

Vazquez, J. M., et al., "A. I. in Swine; New Strategy for Deep Insemination with Low Number of Spermatozoa Using a Non-surgical Methodology", 14th International Congress on Animal Reproduction, vol. 2, Stockholm, Jul. 2000, p. 289.

Vazquez, J., et al., "Developement of a Non-surgical Deep Intra Uterine Insemination Technique", Boar Semen Preservation IV, IVth International Conference on Boar Semen Preservation, Maryland, pp. 262-263.

Vazquez, J., et al., "Hyposmotic Swelling Test as Predictor of the Membrane Integrity in Boar Spermatozoa", Boar Semen Preservation IV, IVth International Conference on Boar Semen Preservation, Maryland, pp. 263.

Vazquez, J., et al., "Successful low dose insemination by a fiber optic Endoscope technique in the Sow", Proceedings Annual Conference of the International Embryo Transfer Society, Netherlands, Theriogenology, vol. 53 Jan. 2000.

Vidament, M., et al., "Equine Frozen Semen Freezability and Fertility Field Results." Therio. 48:907. (1997).

Vincent, B.C., et al, "Carcass Characteristics and Meat Quality of Once-Calved Heifers." Canadian J. Anim. Sci. 71:311. (1991).

Vogel, T., et al, "Organization and Expression of Bovine TSPY", Mammalian Genome, vol. 8, pp. 491-496 (1997).

Voss, J. L. and Pickett, B. W., "Reproductive Management of the Broodmare." CSU Exp. Sta. Anim. Reprod. Lab. Gen. Series. Bull. 961. (1976).

Voss, J. L., et al., "Effect of Number and Frequency of Insemination on Fertility in Mares." J. Reprod. Fertil. Suppl. 32:53-57. (1982).

Voss, J. L., et al., Effect of Human Chorionic Gonadotropin on Duration of Estrus Cycle and Fertility of Normally Cycling, Nonlactating Mares. J.A.V.M.A. 165:704-706. (1974).

Waggoner, A. W., et al., "Performance, Carcass, Cartilage Calcium, Sensory and Collagen Traits of Longissimus Muscles of Open Versus 30-month-old Heifers That Produced One Calf." J. Anim. Sci. 68:2380. 1990.

Welch G., et al., Fluidic and Optical Modifications to a FACS IV for Flow Sorting of X- and Y- Chromosome Bearing Sperm Based on DNA. Cytometry 17 (Suppl. 7): 74. (1994).

Welch, G., et al., "Flow Cytometric Sperm Sorting and PCR to Confirm Separation of X- and Y- Chromosome Bearing Bovine Sperm", Animal Biotechnology, 6, pp. 131-139 (1995).

Wheeler, T. L., et al., "Effect of Marbling Degree on Beef Palatability in Bos-taurus and Bos-indicus cattle." J. Anim. Sci. 72:3145. (1994).

Wickersham, E. W. and L. H. Schultz. "Influence of Age at First Breeding on Growth, Reproduction, and Production of Well-Fed Holstein Heifers." J. Dairy Sci. 46:544. (1963).

Wilhelm, K.M. et al, "Effects of Phosphatidylserine and Cholesterol Liposomes on the Viability, Motility, and Acrosomal Integrity of Stallion Spermatozoa Prior to and after Cryopreservation", Cryobiology 33:320, 1996.

Wilson, C. G., et al., "Effects of Repeated hCG Injections on Reproductive Efficiency in Mares." Eq. Vet. Sci. 4:301-308. (1990).

Wilson, D. E. et al., "Mammal Species of the World", Smithsonian Institution Press, 1993, 1206 pp.

Wilson, M.S. "Non-surgical Intrauterine Artificial Insemination in Bitches Using Frozen Semen." J. Reprod. Fertil. Suppl. 47:307-311. (1993).

Windsor, D. P., et al, "Sex Predetermination by Separation of X and Y Chromosome-bearing Sperm: A Review", Reproduction of Fertilization and Development 5, pp. 155-171, (1993).

Wintzer Et al.:"Krankheiten des Pferdes Ein Leitfaden fur Studium und Praxiz," 1982, nParey, Berlin Hamburg XP002281450.

Woods, G. L. and Ginther, O. J. "Recent Studies Related to the Collection of Multiple Embryos in Mares." Therio. 19:101-108. (1983).

Woods, J., et al., "Effects of Time of Insemination Relative to Ovulation on Preganancy Rate and Enbryonic-Loss Rate in Mares." Eq. Vet. J. 22(6): 410-415. (1990).

Zhou, Hongwei, et al. "Research on and Development of Flow Cell Sorting Apparatuses," Gazette of Biophysics, vol. 13, ed. 3, 1997.

Australian Application No. 17552/01; Monsanto Opposition, Statement of Grounds Mar. 6, 2006.

European Appliction No. 00980567.9; English Translation of Opposition filed by European Union Parliament Nov. 5, 2005 (Document originally filed in German).

European Appliction No. 00980567.9; English Translation of Opposition filed by Greenpeace Nov. 2, 2005 (Document originally filed German).

New Zealand Application No. 530441, Examination Report dated Jul. 13, 2005.

New Zealand Application No. 530441, Letters Patent No. 530441 dated Jan. 12, 2006.

New Zealand Application No. 541086, Examination Report dated Jul. 13, 2005.

Johnson, L. A., Sexing mammalian sperm for production of offspring: the state-of-the-art; Animal Reproduction Science; 60-61 (2000) pp. 93-107.

Seidel, G.E. Jr., et al., Methods of Ovum Recovery and Factors Affecting Fertilization of Superovulated Bovine Ova, Control of Reproduction in the Cow, Sneenan ed., 1978, pp. 268-280.

Hawk, H. W. et al., Effect of Unilateral Cornual Insemination upon Fertilization Rate in Superovulating and Single-Ovulating Cattle, Journal of Animal Sciences, 1986 vol. 63, pp. 551-560.

Andersson, M. et al., Pregnancy Rates in Lactating Holstein-Greisian Cows after Artificial Insemination with Sexed Sperm. Reprod. Dom. Anim 41, 95-97, 2006.

Morton, K. M., et al., In vitro and in vivo survival of bisected sheep embryos derived from frozen-thawed unsorted, and frozen-thawed sex-sorted and refrozen-thawed ram spermatozoa; Theriogenology, 65 (2006) 1333-1345.

Wilson, R. D., et al., In vitro production of bovine embryos using sex-sorted sperm, Theriogenology, 65 (2006) 1007-1015.

Johnson, L.A., et al, 1996 Gender preselection in mammals. XX Beltsville Symposium in Agricultural Research Technolgy's Role in the Genetic Improvement of Farm Animals. pp. 151-164, Amer. Soc. Anim. Sci. IL, USA.

Smorag, Z., et al., Cattle Sex Regulation by Separation of X and Y Spermatozoa—Preliminary Resluts of Field Experiment in Poland, Reproduction, Fertility and Development 17(2) 306-306; Jan. 1, 2005.

Crichton, E., et al. (Abstract) Artificial Insemination of Lactating Holstein Cows with Sexed Sperm, Reproduction, Fertility and Development 18(2) 281-281, Dec. 14, 2005.

Lindsey, A.C., et al. Hysteroscopic insemination of low numbers of flow sorted fresh and frozen/thawed stallion spermatozoa, Equine Vet J. Mar. 2002;34(2):106-7.

Drobnis, E. Z, Cold shock damage is due to lipid phase transitions in cell membranes : a demonstration using sperm as a model, Journal of experimental zoology (J. exp. zool.) 1993, vol. 265, No. 4, pp. 432-437 (22 ref.).

Hagele, W.C., et al., Effect of Separating Bull Semen into X and Y Chromosome-bearing Fractions on the Sex Ratio of Resulting Embryos; Cran J. Comp. Med, 1984: 48:294-298.

U.S. Appl. No. 11/422,735, filed May 25, 2006; Apparatus, Methods and Processes for Sorting Particles and for Providing Sex-Sorted Animal Sperm.

Suh, T.K, et al., Pressure during flow sorting of bull sperm affects post-thaw motility characteristics: Theriogenology vol. 59, No. 1, Jan. 2003 p. 516.

U.S. Appl. No. 10/266,562, filed Oct. 7, 2002; Office Action Dated Aug. 23, 2006.

Rath, D, et al., In Vitro Production of Sexed Embryos for Gender Preselection: High-speed sorting of X-Chromosome-Bearing Sperm to Produce Pigs After Embryo Transfer, J. Anim. Sci. 1999, 77:3346-3352.

Auchtung, T.L., et al., Effects of Photoperiod During the Dry Period on Prolactin, Prolactin Receptor, and Milk Production of Dairy Cows; Journal of Dairy Sci. 88: 121-127; American Dairy Sci. Assoc., 2005.

Bailey, Tom and Currin, John Milk Production Evaluation In First Lactation Heifers; 1999 Virginia Cooperation Extension/Dairy Science Publication 404-285.

Belloin, J.C., Milk and Dairy products: production and processing costs Food and Agriculture Organization of United Nations Rome 1988 FAO; web page where found: www.fao.org/docrep/003/x6931e/X6931E00.htm.

Kume, Shin-ichi; Dept of Animal Nutrition National Institute of Animal Industry Tsukuba 305, Japan The Dairy Industry $IN ASIA B. Japan; www.agnet.org/library/article/eb384b.html.

Crichton,E.; Huffman,S.;McSweeney,K.;and Schenk, J. 347 Artificial Insemination of Lactating Holstein Cows with sexed sperm: Abstract CSORP Publishing—Reproduction, Fertility and Development www.publish.csiro.au/nid/44/paper/RDv18n2Ab347.htm.

Lopez, H., Caraviello, D.Z., Satter, L.D. ,Fricke, P.M. and Wiltbank, M.C.; Relationship Between Level of Milk Production and Multiple Ovulation in Lactating Dairy Cows Journal of Dairy Sci. 88:2783-2793; American Dairy Science Association, 2005.

Managing the Dairy Cow During the Dry Period; Dairy Cattle Production 341-450A; Macdonald Campus of McGill University/Faculty of Agricultural & Environmental Sciences/Department of Animal Science.

Milk Production and Biosynthesis University of Guelph/Dairy Science and Technology www.foodsci.uoguelph.ca/dairyedu/biosyntheses.html.

Milk Production Released Jul. 18, 2006, by the National Agricultural Statistics Service (NASS), Agri. Stats. Board, US Dept of Agri.

De Vries, A. Ecomonic Value of Pregnancy in Dairy Cattle Journal of Dairy Sci. 89:3876-3885/American Dairy Sci. Assoc. 2006.

* cited by examiner

METHOD OF CRYOPRESERVING SELECTED SPERM CELLS

CROSS-REFERENCE TO RELATED APPLICATIONS

The applications claims the benefit of U.S. Provisional Application No. 60/167,423, filed Nov. 24, 1999.

FIELD OF THE INVENTION

The invention relates to a method for freezing sperm selected for a particular characteristic, as well as to a frozen selected sperm sample and methods of using such a sample. The invention is particularly useful for preserving sex-selected sperm.

BACKGROUND OF THE INVENTION

Over half a century ago, artificial insemination was introduced in the United States as a commercial breeding tool for a variety of mammalian species. Although artificial insemination was initially limited to regions relatively close to the site of sperm collection, advances in the cryopreservation and storage of sperm have facilitated widespread distribution and commercialization of sperm intended for artificial insemination or in vitro fertilization.

Further improvements in mammalian sperm collection, selection, cryopreservation, storage, and handling techniques have enhanced the ability of breeders to produce animals having desired traits. For example, advances in selection of mammalian sperm based on slight differences in physical characteristics has made it possible to separate sperm based on sex-type, that is, to select for cells containing either the X or Y chromosome. This technique allows the breeder to manipulate the relative percentage of X- or Y-type sperm in a sample and thereby determine offspring sex. The ability to select sperm based on sex-type or any other desirable characteristic provides an important tool for accelerating genetic progress, increasing production efficiency, and achieving greater flexibility in livestock management. Full exploitation of this tool, however, depends on the ability to freeze and store selected sperm.

A variety of methods are available for selecting cells; however, the selection and subsequent processing of sperm presents unique challenges because sperm are incapable of DNA repair and because of sperm morphology. Each sperm has an acrosome overlying the head and a tail, which are important for fertility and which are relatively susceptible to physical injury. In addition, sperm fertility decreases with increasing time between collection and use. As most of the available selection methods involve physical stresses and take time, selected sperm are typically somewhat compromised compared to non-selected cells. Fertility may be further reduced if the selection technique involves significant dilution. It has been suggested that this "dilution effect" may be due to the loss of protective components in seminal plasma.

Flow cytometry is a particularly efficient selection method that has been employed for sorting sperm by sex-type. However, sorted sperm are subject to stresses beyond those normally encountered in standard artificial insemination or in vitro fertilization protocols. In particular, flow cytometry is time consuming, and, because of the physical constraints of flow cytometers, sperm must be diluted for sorting to levels that are not optimal for storage (usually to on the order of $10^5$–$10^6$/ml). Furthermore, sorted sperm intended for artificial insemination must be concentrated so that conventional packaging and delivery equipment can be used. The need for a concentration step thus exposes already somewhat compromised sperm to additional physical stresses.

The freezing of sperm also invariably reduces fertility, motility, and/or viability, and, although techniques for freezing unselected sperm are well known, no technique for cryopreservation of selected sperm has been described.

SUMMARY OF THE INVENTION

The present invention provides a method of cryopreserving sperm that have been selected for a specific characteristic. The method is particularly useful for cryopreserving sperm selected by a method that results in dilution of the sperm, since the method provides for the isolation of sperm from a selected sperm sample, followed by addition of a final extender to the isolated sperm to produce a suspension having a desired concentration of sperm. In a preferred embodiment, the method is employed to freeze sex-selected sperm. Although the cryopreservation method of the invention can be used to freeze sperm selected by any number of selection methods, selection using flow cytometry is preferred.

The present invention also provides a frozen sperm sample that has been selected for a particular characteristic, such as sex-type. In preferred embodiments, the frozen sperm sample includes mammalian sperm, such as, for example, human, bovine, equine, porcine, ovine, elk, or bison sperm. Also within the scope of the invention is a container including a frozen sperm sample according to the invention.

The frozen selected sperm sample can be used in a variety of applications. In particular, the sample can be thawed and used for fertilization. Accordingly, the invention also includes a method of using the frozen selected sperm sample for artificial insemination or in vitro fertilization.

DETAILED DESCRIPTION OF THE INVENTION

The present invention allows cryopreservation of sperm that have been selected for a particular characteristic, facilitating storage and/or shipment of selected sperm samples to sites distant from the collection site. Thawing yields viable sperm that can be used in procedures such as artificial insemination ("AI") and in vitro fertilization ("IVF"). This result was surprising because of the well-documented fragility of sperm. Prior researchers had demonstrated that the stresses associated with various selection methods or with cryopreservation resulted in significant losses in fertility and/or viability. The present inventors have demonstrated, for the first time, that pregnancies can be achieved with sperm that have been selected and then frozen.

The invention represents an important advance in livestock management, where selection of sperm for use in such procedures can be used to increase the production of offspring having desirable traits. For example, selection to obtain sperm carrying either the X or the Y chromosome allows control over offspring sex, which is advantageous for producers of animals such as dairy or beef cattle. Sex selection also finds application in breeding valuable (e.g., show or race horses) or endangered animals. The ability to freeze selected sperm, which the invention provides, will enable widespread use of such selection methods to, e.g., increase livestock production efficiency as well as quality.

Definitions

The term "acrosome" or "acrosomal cap" refers to the cap that covers the anterior half of the head of sperm and that contains enzymes necessary for ovum penetration.

The term "sex-type" refers to the type of sex chromosome present in the sperm (i.e., the X or Y chromosome).

The term "capacitation" refers to the specific changes a sperm undergoes to develop the capacity to fertilize ova, such as enzymic changes on the surface of the acrosome that lead to release of acrosomal enzymes that facilitate penetration of the sperm into the ovum.

As used with reference to sperm, the term "cryoprotectant" refers to a molecule that protects sperm during a freeze-thaw cycle, promoting survival and retention of fertilizing capacity.

The term "dilution effect" refers to the rapid decline in motility and/or viability of sperm when highly diluted.

As used herein, the term "selection" refers to a method whereby a sample is subdivided based on presence or absence of a specific characteristic (unless context dictates otherwise). Thus, a "selected sperm sample" is a sample obtained by subjecting a source sample to selection for the specific characteristic. A selected sperm sample is therefore enriched, relative to the source sample, in sperm having the specific characteristic.

The term "sorting" is used herein to describe a selection method carried out using a fluorescence-activated cell sorter (FACS).

The term "extender" refers to any medium that tends to preserve sperm viability. The term "extension" refers to the dilution of sperm with extender.

The term "initial extender" refers to a medium used to extend sperm prior to the isolation step of the method of this invention.

The term "final extender" refers to a medium used to extend sperm prior to the freezing step of the method of this invention.

An "organic substance" in an extender described herein is any organic substance that tends to reduce cold shock and preserve fertility of sperm.

An "energy source" in an extender described herein is any substance or substrate that sperm can utilize for cell maintenance and/or motility.

The term "osmolality," as used herein, is a measure of the osmotic pressure of dissolved solute particles in a an aqueous solution (e.g., an extender). The solute particles include both ions and non-ionized molecules. Osmolality is expressed as the concentration of osmotically active particles (i.e., osmoles) dissolved in 1 kg of water.

Cryopreservation Method

The invention provides a method of cryopreserving selected sperm includes the following steps:
(1) obtaining a selected sperm sample;
(2) cooling the selected sperm sample;
(3) isolating sperm from the selected sperm sample;
(4) adding final extender to the isolated sperm to produce a suspension of sperm; and
(5) freezing the suspension of sperm.

Obtaining a Selected Sperm Sample

The first step in the cryopreservation method of the invention encompasses obtaining a previously selected sperm sample, as well as subjecting a source sample to any suitable selection method. Sperm from any species can be selected and frozen according to the method of the invention. The method can be carried out with sperm from domesticated animals, especially livestock, as well as with sperm from wild animals (e.g., endangered species). Preferably, the selected sperm sample contains mammalian sperm. Human sperm, bovine, equine, porcine, ovine, elk, and bison sperm are particularly preferred.

Generally, the selected sperm sample contains normal, viable sperm. To this end, the ejaculate from which the sperm are obtained typically has at least about 50%, and preferably at least about 75% morphologically normal sperm. In these embodiments, generally at least about 40%, and preferably at least about 60% of the sperm in the ejaculate exhibit progressive motility.

A wide variety of methods for selecting cells from a mixed populations are available, including, for example, selection based on binding of cells or cell components with antibodies, antibody fragments, or other binding partners and differential staining.

The invention is exemplified herein with selection based on sex-type, and sex-selected sperm for use in the invention can be obtained using any selection strategy that takes advantage of slight differences in characteristics between X- and Y-type sperm. Exemplary sex-selection methods include magnetic techniques (see, e.g., U.S. Pat. No. 4,276,139), columnar techniques (see, e.g., U.S. Pat. No. 5,514,537) gravimetric techniques (see, e.g., U.S. Pat. No. 3,894,529, reissue Pat. No. 32350, U.S. Pat. Nos. 4,092,229, 4,067,965, and 4,155,831). Sex-selection based on differences in electrical properties is disclosed in U.S. Pat. No. 4,083,957, and techniques that select based on differences in electrical and gravimetric properties are discussed in U.S. Pat. Nos. 4,225,405, 4,698,142, and 4,749,458. U.S. Pat. Nos. 4,009,260 and 4,339,434 describe selection based on differences in motility. Biochemical techniques relying on antibodies are disclosed in U.S. Pat. Nos. 4,511,661, 4,999,283, 3,687,803, 4,191,749, 4,448,767, whereas U.S. Pat. Nos. 5,021,244, 5,346,990, 5,439,362, and 5,660,997 describe selection based on differences in membrane proteins.

Flow cytometry is a preferred method for separating cells from mixed populations based on differential staining with fluorescent dyes or binding to fluorescently labeled molecules, such as antibodies or nucleic acids. In fluorescence activated cell sorting ("FACS"), cells are "sorted" into different populations based on the fluorescence intensity upon irradiation. FACS can be used for sex-selection of sperm because the X chromosome contains slightly more DNA than the Y chromosome. When sperm are stained with a fluorescent DNA-binding dye, X-chromosome bearing sperm absorb more dye than Y-chromosome bearing sperm and the two populations can therefore can be separated by FACS. This strategy was discussed in U.S. Pat. No. 4,362,246 and significantly expanded upon in U.S. Pat. No. 5,135,759 (issued to Johnson). Separation has been enhanced through the use of high-speed flow cytometers, such as the MoFlo® flow cytometer produced by Cytomation, Inc. (Ft. Collins, Colo.) and described in U.S. Pat. Nos. 5,150,313, 5,602,039, 5,602,349, and 5,643,796, as well as in PCT Publication No. WO 96/12171.

The selection method used to obtain the selected sperm sample is preferably one that preserves sperm viability. Because of the relative fragility of sperm, normal flow cytometry techniques should generally be modified for sorting sperm. More specifically, the flow cytometry entails staining, dilution, and interrogation of cells with light. All of these steps represent stresses that can reduce sperm viability. The sensitivity of sperm to these stresses can vary between species and even between individuals within species. Such sensitivities have either been documented or can readily be determined by empirical studies, such as those described in Examples 1–5.

Modifications that enhance viability are described the patent publications discussed above. For instance, procedures that provide improved sheath and collector systems for sorting sperm are disclosed in PCT Publication No. WO 99/33956 (Application No. PCT/US98/27909). Further, Examples 1–7 below describe exemplary procedures for staining and sorting sperm. Example 3 describes a study of the effects of laser intensity and dye concentration of post-thaw motility of sorted frozen sperm. This study indicates that the use of lower laser intensities during sorting can increase post-thaw motility.

The selected sperm sample can contain a variety of components besides sperm and will often contain components added to protect the sperm during the selection process. In the case of FACS, the selected sperm sample can contain component(s) of the solutions used for staining and sorting (e.g., the sheath fluid and the catch buffer).

In addition, the selected sperm sample typically contains an extender or extender fraction. For example, "two-step" extenders including an "A fraction" lacking glycerol and a "B fraction" Containing glycerol are well known. The A fraction is added to sperm first, followed by addition of an equal volume of the B fraction. For this step, the B fraction is often divided into at least two aliquots and added sequentially; e.g., the second B fraction aliquot is added 15 minutes after the first.

If no extender components are present, an extender or extender fraction is typically added to the selected sperm sample before the sperm are isolated from the sample. If only some extender components are present, additional components can optionally be added so that selected sperm sample includes a complete extender or an extender fraction before the isolation step. In exemplary embodiments, bovine sperm are flow-sorted so as to produce a selected sperm sample including the A fraction of an extender (see Examples 2, 3, and 4). If desired, the B fraction can then be added to the selected sperm sample before the isolation step (see Example 5). The pre-isolation step extender (or extender fraction) is termed "the initial extender" to distinguish it from the "final extender" employed for the extension of isolated sperm before freezing. If the selected sperm sample was selected using FACS, the initial extender can be matched to the sheath fluid employed for sorting. Exemplary matched sheath fluids and extenders are described in detail in Example 4.

An extender suitable for use in the selected sperm sample includes a physiologically acceptable carrier. The physiologically acceptable carrier is typically aqueous, and, in preferred embodiments, includes deionized water. Suitable extenders commonly comprise one or more of the following additional components: a cryoprotectant, a component that maintains osmolality and buffers pH, an organic substance that prevents cold shock and preserves fertility of sperm, a detergent that acts synergistically with certain organic substances to enhance preservation of sperm, an energy source that can be readily utilized by sperm, an antioxidant, which protects sperm from cold shock, a substance that facilitates sperm capacitation, and one or more antibiotics.

Although cryoprotectants useful in the invention are not limited to those acting by a particular mechanism, most conventional cryoprotectants act, at least in part, by reducing intracellular dehydration. Specifically, freezing is accompanied by an increase in solute concentration in the medium surrounding sperm. This increase in solute concentration draws water out of the cells, which increases intracellular electrolyte concentration. Exemplary cryoprotectants include glycerol, dimethyl sulfoxide, ethylene glycol, propylene glycol, and the like. The cryoprotectant suitable for use in a given extender can vary, depending on the species from which sperm are derived. For example, glycerol is suitable for use in cryopreservation of human and bovine sperm, but is generally not used for cryopreservation of porcine or rabbit sperm. Such preferences are well known for many commercially valuable sperm and can readily be determined empirically for other types of sperm.

The extender useful in the invention optionally includes one or more components that help maintain osmolality and provide buffering capacity. In preferred embodiments of the invention, the osmolality of the extender approximates that of physiological fluids. More preferably, the osmolality of the extender is in the range of about 280 mOsm to about 320 mOsm. The pH is also preferably within a physiologically acceptable range, more preferably in the range of about 6.5 to about 7.5.

Substances helpful in maintaining omolality and pH within these ranges are well known in the art and can be added to the extender as a solid or already in solution. A buffer containing a salt, a carbohydrate, or a combination thereof can be employed for this purpose. Specific examples include sodium citrate, Tris[hydroxymethyl]aminomethane, and TES (N-Tris[Hydroxymethyl]methyl-2-aminoethanesulfonic acid), and monosodium glutamate buffers; milk; HEPES-buffered medium; and any combination thereof. The component employed to help maintain osmolality and provide buffering capacity in a particular application can vary depending on the other components of the extender and, in some cases, on the species from which the sperm are derived. The selection of such a component for use in the present invention is, however, within the level of skill in the art.

One or more organic substances that protect sperm against cold shock and help preserve fertilizing capacity can also be included in the extender. Such substances are well known and are sometimes described as "nonpenetrating cryoprotectants." One skilled in the art can readily determine an organic substance suitable for a particular application of the cryopreservation method described herein. For example, organic substances containing protective constituents (e.g., lipoproteins, phospholipids, lecithin) that are believed to reduce the impact of cold shock and the dilution effect can be included in the extender. Suitable organic substances include disaccharides, trisaccharides, and any combination thereof. Exemplary organic substances include egg yolk, an egg yolk extract, milk, a milk extract, casein, albumin, lecithin, cholesterol, and any combination thereof.

The extender can also include a detergent. Alkyl ionic detergents, such as sodium dodecyl sulfate (SDS), have been reported to act synergistically with egg yolk to enhance protection against cold shock. Other detergents useful in the cryopreservation of cells can also be employed in the extender, and the selection of a particular detergent for a specific application is within the level of skill in the art in light of the guidance provided herein. See, e.g., Example 5.

Preferably, the extender includes an energy source that is readily utilized by sperm. In the absence of an energy source, sperm may oxidize intracellular phospholipids and other cellular components. Thus, the inclusion of an energy source in the extender protects intracellular reserves and cellular components. As is well known in the art, sugars, particularly monosaccharides, provide a convenient energy source, although any conventional energy source can be employed in the extender. Exemplary monosaccharides useful in the extender include glucose, fructose, and/or mannose.

One or more antioxidants can optionally be included in the extender to provide additional protection against cold shock. Exemplary antioxidants include butylated hydroxytoluene (BHT), its derivatives, and the like. However, other antioxidants useful in the cryopreservation of cells can also be employed in the extender, and the selection of a particular antioxidant for a specific application is within the level of skill in the art in light of the guidance provided herein.

The extender can also contain a substance that facilitates sperm capacitation. A variety of capacitation facilitators are known in the art and any can be employed in the extender. Examples include enzymes such as alpha amylase, beta amylase, beta glucuronidase, which can be used in combination, if desired.

Finally, the extender preferably includes an antibiotic, since substantial bacterial growth can threaten sperm viability and increase the risk of infection of the host in artificial insemination or in vitro fertilization procedures. Any of a variety of antibiotics useful in the cryopreservation of cells can also be employed in the extender. The selection of a suitable antibiotic depends on the species from which the sperm was obtained, the procedures involved in obtaining and handling the sperm sample, and the specific microorganism(s) to be targeted. Exemplary antibiotics include tylosin, gentamicin, lincomycin, spectinomycin, linco-spectin (a combination of lincomycin and spectinomycin), penicillin, streptomycin, and ticarcillin, which can be used alone or in combination. However, one skilled in the art can readily determine other antibiotics suitable for use in the extender.

Exemplary extenders are discussed in greater detail below and in the examples.

The sperm concentration is typically lower in the selected sperm sample than in the source sample, and, as indicated above, when FACS is employed, the dilution is significant. A typical sort based on sex-type can produce a sample containing sperm at $6 \times 10^5$ cells/ml catch buffer. As such a low concentration is not optimal for storage (at least for most species tested), the cryopreservation method of the invention generally concentrates the selected sperm sample.

Cooling the Selected Sperm Sample

The second step in the cryopreservation method entails cooling the selected sperm sample, typically, by reducing the temperature at a controlled rate. Cooling too rapidly can cause cold shock, which can result in a loss of membrane integrity and cell function. The severity of the effects of cold shock vary from species to species and depend on factors such as the rate of cooling and the temperature range. Under suitable controlled cooling conditions, the sperm are able to adapt to thermal effects. Example 2, among others, describes conditions for cooling bovine sperm, and determining suitable conditions for cooling sperm of other species is within the level of skill in the art.

In a preferred embodiment of the invention, the selected sperm sample is cooled typically from about 22° C., to about 5° C., and cooling is generally carried out over a period of about 60 minutes to about 24 hours, preferably over a period of about 90 minutes to about 240 minutes, and most preferably over a period of about 90 minutes to about 120 minutes. Cooling can be accomplished by any convenient method, including simply placing the selected sperm sample in a 5° C. environment.

Isolation of Sperm Cells from the Selected Sperm Sample

After initial extension of the selected sperm sample, sperm are isolated from the sample using any sufficiently gentle isolation method that provides at least about 50% recovery of sperm, more preferably about 75% to about 90% recovery of sperm, and most preferably about 80% to about 90% recovery of sperm. During the isolation step, the cooled sperm should generally be kept cold, i.e., between about 1 and about 8° C., and preferably close to 4 or 5° C.

Any of a variety of methods suitable for recovering cells from a suspension can be used to isolate the sperm, including for example, filtration, sedimentation, and centrifugation. In an exemplary, preferred embodiment, the selected sperm sample is aliquoted into 50 ml tubes at volumes not exceeding about 27 ml, and preferably between about 20 to about 27 ml. Centrifugation is carried out at about 4° C., at about 850×g, for about 20 minutes. Preferably, the centrifugation step provides at least about 50% to about 90% recovery of sperm, more preferably about 60% to about 90% recovery of sperm, and most preferably about 70% to about 90% recovery of sperm. After isolation, the supernatant is removed and the pellet is suspended by vortexing gently or repeated aspiration at 4° C. The sperm concentration is then typically determined (e.g., using a hemacytometer).

Final Extension of Isolated Sperm Cells

After isolation, the sperm are pooled, if desired, and extended with final extender to an appropriate concentration for freezing. The concentration of sperm after the final extension and prior to freezing is preferably in the range of about $1 \times 10^6$/ml to about $300 \times 10^6$/ml, more preferably about $10 \times 10^6$/ml to about $50 \times 10^6$/ml, and most preferably about $10 \times 10^6$/ml to about $20 \times 10^6$/ml.

The description of the initial extender above also applies to the final extender, which can be the same as or different from the initial extender. In particular embodiments, the composition of the sperm sample extended with the final extender is substantially similar to (if not the same as) the composition of the sperm sample after addition of the initial extender.

In a preferred embodiment of the invention, an egg yolk-Tris extender is used. After the addition of the extender, the sperm suspension comprises glycerol (cryoprotectant); citric acid and Tris[hydroxymethyl]aminomethane (buffer); egg yolk (organic substance); fructose (energy source); tylosin, gentamicin, and linco-spectin (antibiotics). The typical approximate concentrations of these components after addition of the final extender to the isolated sperm are:

| Components of Egg Yolk-Tris Extender | |
|---|---|
| Glycerol: | 4–8% vol/vol |
| Citric Acid: | 55–75 mM |
| Tris [hydroxymethyl]aminomethane: | 190–210 mM |
| Egg yolk: | 5–25% vol/vol |
| Fructose: | 45–65 mM |
| Tylosin: | 25–100 µg/ml |
| Gentamicin: | 200–300 µg/ml |
| Linco-spectin: | 100–400 µg/ml* |

*100–400 µg/ml lincomycin and 100–400 µg/ml spectinomycin

In a variation of this embodiment particularly suitable for freezing bovine sperm, the concentrations of these components after addition of the final extender to the isolated sperm are about 6% (vol/vol) glycerol, about 65 mM citric acid, about 200 mM Tris[hydroxymethyl]aminomethane, about 20% (vol/vol) egg yolk, about 56 mM fructose, about 50 μg/ml tylosin, about 250 μg/ml gentamicin, and about 150/300 μg/ml linco-spectin (i.e., 150 μg/ml lincomycin and 300 μg/ml spectinomycin), in deionized water.

In an alternative embodiment, an egg yolk-citrate extender is employed. After the addition of the extender, the sperm suspension comprises glycerol (cryoprotectant); sodium citrate (buffer); egg yolk (organic substance); tylosin, gentamicin, and linco-spectin (antibiotics). The typical approximate concentrations of these components after addition of the final extender to the isolated sperm are:

| Components of Egg Yolk-Citrate Extender | |
|---|---|
| Glycerol: | 4–8% vol/vol |
| Sodium Citrate: | 60–80 mM |
| Egg yolk: | 5–25% vol/vol |
| Tylosin: | 25–100 μg/ml |
| Gentamicin: | 200–300 μg/ml |
| Linco-spectin: | 100–400 μg/mL* |

*100–400 μg/ml lincomycin and 100–400 μg/ml spectinomycin

Exemplary, preferred concentrations for freezing bovine sperm are about 7% (vol/vol) glycerol, about 72 mM sodium citrate, about 20% (vol/vol) egg yolk, about 50 μg/ml tylosin, about 250 μg/ml gentamicin, and about 250/300 μg/ml linco-spectin.

In another alternative embodiment, an egg yolk-TES-Tris ("EY TEST") extender is employed. After the addition of the extender, the sperm suspension comprises glycerol (cryoprotectant); egg yolk and heated milk, e.g., homogenized milk containing 1.25% fructose with 10% glycerol (organic substances); tylosin, gentamicin, and linco-spectin (antibiotics). The typical approximate concentrations of these components after addition of the final extender to the isolated sperm are:

| Components of Egg Yolk TES-Tris Extender | |
|---|---|
| Glycerol: | 3–7% vol/vol |
| Tris [hydroxymethy-methyl]-2-aminoethanesulfonic acid: | 140–170 mM |
| Tris [hydroxymethyl]aminomethane: | 60–80 mM |
| Egg yolk: | 5–25% vol/vol |
| Fructose: | 5–12 mM |
| Tylosin: | 50–150 μg/ml |
| Gentamicin: | 400–600 μg/ml |
| Linco-spectin: | 200–700 μg/mL* |

*200–700 μg/ml lincomycin and 200–700 μg/ml spectinomycin

Exemplary, preferred concentrations for freezing bovine sperm are about 5% (vol/vol) glycerol, about 158 mM Tris[hydroxymethy-methyl]-2-aminoethanesulfonic acid, about 72 mM Tris[hydroxymethyl]aminomethane, about 20% (vol/vol) egg yolk, about 8 mM fructose, about 100 μg/ml tylosin, about 500 μg/ml gentamicin, and about 300/600 μg/ml linco-spectin.

In yet another alternative embodiment of the invention, a Milk extender is employed. After the addition of the extender, the sperm suspension comprises glycerol (cryoprotectant); heated homogenized milk (organic substance); fructose (energy source); and tylosin, gentamicin, and linco-spectin (antibiotics). The typical approximate concentrations of these components after addition of the final extender to the isolated sperm are:

| Components of Milk Extender | |
|---|---|
| Homogenized Milk | 90% (vol/vol) |
| Glycerol: | 3–7% (vol/vol) |
| Fructose: | 1.25% (wt/vol) |
| Tylosin: | 50 μg/ml |
| Gentamicin: | 250 μg/ml |
| Linco-spectin: | 250/300 μg/ml* |

*250–300 μg/ml lincomycin and 250–300 μg/ml spectinomycin

Exemplary preferred concentrations for freezing bovine sperm are about 90% milk, about 10% (vol/vol) glycerol, about 1.25% fructose (wt/vol?), about 50 μg/ml tylosin, about 250 μg/ml gentamicin, and about 250/300 μg/ml linco-spectin.

Other extenders standardly used to freeze sperm can also be employed as the final extender in freezing selected sperm. A variety of extenders optimized for use in freezing sperm from various species have been described, and many are commercially available. Freezing extenders for equine sperm typically consist of milk, egg yolk, various sugars, electrolytes and a cryoprotectant. Exemplary freezing extenders are described by Squires, E. L., et al., *Cooled and Frozen Stallion Semen Animal Reprod. and Biotechnology Laboratory*, Bulletin No. 69, Chapter 8, "Seminal Extenders" pp. 49–51 (July, 1999).

Equilibration and Freezing of Sperm

Extension of the sperm sample produces a suspension of sperm, which is then transferred into containers for freezing. If the sperm are intended for use in fertilization, the cells are conveniently aliquoted into individual doses sufficient to achieve fertilization. The required dose can vary substantially from one species to the next and is either well-known (e.g., for cattle and horses) or can readily be determined. In the case of sex-selected bovine sperm, convenient doses range from about $1.0 \times 10^6$ sperm to about $3.0 \times 10^6$ sperm.

Any suitable container can be employed for freezing, including, for example, an ampule, a vial, and a straw. Sperm intended for AI are typically frozen in straws (e.g., 0.25 ml or 0.50 ml straws) designed for use with an insemination gun. Preferably, a bolus of extender is drawn into the straw, followed, in sequence, by air, sperm, air, and extender, so that the sperm are flanked on either side by an air space, which separates the sperm from a bolus of extender at either end of the straw.

Prior to freezing, the sperm are generally allowed to equilibrate at about 5° C. Preferably, the sperm are allowed to equilibrate for a period in the range of about 1 hour to about 18 hours, more preferably between about 3 hours and about 18 hours, and most preferably between about 3 hours and about 6 hours (see Example 2).

Following equilibration, any standard freezing method can be employed, provided the freezing rate is not too rapid (i.e., not in excess of about 0.5° C./minute). Preferably, the freezing rate is about 0.5° C./minute. In an exemplary, preferred embodiment, the sperm are placed in static liquid nitrogen vapor, and freezing is carried out in three distinct stages over a period of about 10 minutes. In the first stage of freezing, the sperm are cooled from about 5° C. to about ⁻15° C. at a rate of about 40° C./minute to about 65° C./minute. In the second stage of freezing, the sperm are cooled from about ⁻15° C. to about ⁻60° C. at a rate of about 25° C./minute to about 35° C./minute. In the third stage, the sperm are plunged into liquid nitrogen at about ⁻100° C.

Selected Sperm Samples

In addition to a freezing method, the invention provides a frozen sperm sample including sperm selected from a source sample for a particular characteristic. The sperm can be from any species, including any of those discussed above with reference to the freezing method. The invention encompasses frozen sperm selected for any characteristic by any suitable method, such as those described above. Preferred embodiments include frozen sex-selected human, bovine, equine, porcine, ovine, elk, or bison sperm. Sex-selection is preferably carried out using flow cytometry as described generally above.

Also within the scope of the invention is a container containing a frozen sperm sample according to the invention. The container can be formed from any material that does not react with the frozen sperm sample and can have any shape or other feature that facilitates use of the sample for the intended application. For samples intended for use in AI, for example, the container is conveniently a straw (e.g., 0.25 ml or 0.5 ml straw) designed for use with an insemination gun. The container is sealed in any manner suitable for preserving the sample at the intended storage temperature, which is typically below −80° C. 0.25 ml straws can be sealed, for instance, with PVC powder, ultrasonically, or with a cotton-polyvinyl plug and/or a stainless steel ball (BB).

As the frozen sperm sample of the invention is typically thawed before use, the invention also provides a thawed, previously frozen, selected sperm sample and a container including such a thawed sample.

Methods of Using the Selected Sperm Sample

The frozen selected sperm sample of the invention is suitable for use in any method in which sperm are used. The sample can be thawed and used in any conventional fertilization method, such as artificial insemination or in vitro fertilization. Thawing is carried out in the same manner as for frozen, non-selected sperm. Briefly, the straw containing the frozen sperm is submerged in a water bath maintained at a temperature of about 35° C. to about 37° C. for a period of about 20 to about 30 seconds. After thawing, semen deposition (e.g., insemination) is carried out according to standard procedures, taking care to protect the sperm from environmental fluctuations.

EXAMPLES

Example 1

Effects of Dilution on Sperm

Objective: to determine the effect of sperm concentration on sperm motility for non-frozen, non-sorted, but highly diluted sperm.

A. Effects of Dilution on Non-Washed Sperm

1. Collection of Source Sample. Sperm were collected from bulls on a routine collection schedule using an artificial vagina as described in Schenk J., Proc 17th NAAB, p. 48–58 (1998), and Saacke R G, Proc NAAB Tech Conf AI Reprod. 41:22–27 (1972). All ejaculates used contained greater than 50% progressively motile and greater than 75% morphologically normal sperm. Antibiotics were added to the raw ejaculate as described by Shin S., Proc NAAB Tech Conf AI Reprod. 11:33–38 (1986) within 15 minutes of collection, and the concentration of sperm was determined using a spectrophotometer.

2. Methods. Sperm from 4 bulls were diluted to 1.25, 2.5, 5, 10, 15, and $20 \times 10^6$/ml using an egg yolk-citrate extender (EYC) prepared with 20% egg yolk (vol/vol) in 72 mM sodium citrate, 50 µg/ml tylosin, 250 µg/ml gentamicin, and 250/300 µg/ml linco-spectin. Each sample was prepared in duplicate (2 tubes/dilution/bull) and comprised 8 ml total volume per tube. All samples were incubated for 60 minutes at 22° C., after which they were centrifuged using a swinging bucket centrifuge (Eppendorf, Model # 5810R) at 600×g for 10 minutes to concentrate the sperm. After centrifugation, the supernatant from one set of the duplicate tubes was not removed; the sperm were resuspended in the same medium and at the original concentration by repeated gentle aspiration using a 5-ml serological pipette. (The second set of the duplicate tubes were used in Example 1B.) Sperm samples were then cooled to 5° C. at 0.2° C./min over 90 minutes. These sperm were termed "non-washed sperm." All samples were incubated at 5° C. for 24 or 48 h post-collection.

3. Evaluation of Motility. After incubation, the samples were warmed to 37° C. using a dry block incubator for 10 minutes prior to determination of motility. For this experiment, a single, blind estimate of the percentage of progressively motile sperm was determined for each sample. Progressive sperm motility was determined subjectively for each subclass by a single observer (×200, phase-contrast microscopy); another person prepared the microscope slides in a randomized manner so the observer was unaware of treatments.

4. Statistical Analysis. Data were analyzed by analysis of variance (SAS Institute, Cary, N.C.) with factors bulls and initial dilution concentration. Separate analyses were done for each incubation time. Dilution trends were tested using (log) linear contrasts.

5. Results. Data for non-washed sperm (Table 1) revealed (log) linear relationships (P<0.01) for both incubation times. Percentages of motile sperm increased as sperm concentration increased from $1.25 \times 10^6$/ml to $10 \times 10^6$/ml, but there was little difference thereafter. The cubic term was significant (P<0.05) for 24-h and marginally significant (P<0.1) for 48-h incubations. There was a bull effect (P<0.01) at both times.

TABLE 1

Effects of cooling on non-washed sperm motility (%) after cooling to 5° C.

| Dilution | Incubation at 5° C. | |
|---|---|---|
| ($10^6$/ml) | 24 h[a] | 48 h[b] |
| 1.25 | 18[c] | 0[c] |
| 2.5 | 38[c,d] | 6[c,d] |
| 5.0 | 56[d] | 31[d,e] |
| 10.0 | 61[d] | 42[e] |
| 15.0 | 55[d] | 44[e] |
| 20.0 | 58[d] | 41[e] |
| S.E.[f] | 5.6 | 6.4 |

[a](log) linear (P < 0.01) and cubic effects (P < 0.05).
[b](log) linear (P < 0.01) and cubic effects (P < 0.1).
[c,d,e]Means within columns without common superscripts differ (P < 0.05).
[f]$\sqrt{\text{error mean square of ANOVA}} \div \sqrt{N}$ (SAS Institute, Cary, NC, USA)

B. Effects of Dilution on Washed Sperm

1. Collection of Source Sample. The second set of the duplicate tubes containing samples prepared in Example 1A were used in this experiment.

2. Methods. The sperm were diluted, incubated and concentrated by centrifugation as in Example 1A. Following centrifugation, 7.1 ml of the supernatant was aspirated from each tube, removing most of the seminal plasma and leaving the sperm in a 900-μl pellet. The sperm were diluted with EYC (see Example 1A) to make $10 \times 10^6$/ml or $20 \times 10^6$/ml sperm suspensions. The samples were then cooled to 5° C. over 90 minutes as in Example 1A.

3. Evaluation of Motility. The samples were warmed and evaluated for progressive motility as in Example 1A.

4. Statistical Analysis. Data were analyzed as in Example 1A. In addition, data in Example 1B were analyzed for incubation concentration at 5° C.

5. Results. Data for washed sperm (Table 2) revealed no significant treatment effects when sperm were evaluated after 24 h. However, after storage for 48 h at 5° C., there were bull, initial dilution, incubation concentration and bull by incubation effects ($P<0.05$). More sperm remained motile when held at $20 \times 10^6$/ml than at $10 \times 10^6$/ml (31% vs. 20%; $P<0.05$). Initial dilutions of 1.25, 2.5, and $5 \times 10^6$ sperm/ml resulted in lower progressive motility than $10 \times 10^6$ sperm/ml ($P<0.05$), with respective main effect means of 19, 20, 27, and 37% motile sperm.

TABLE 2

Cumulative effects of washing, dilution, concentration and cooling on progressive sperm motility (%)

| Sperm conc ($10^6$/ml) during 1 h preincubation at 37° C. | Storage at 5° C. - Sperm Concentration and Duration | | | |
|---|---|---|---|---|
| | 24 h | | 48 h[a] | |
| | $20 \times 10^6$/ml | $10 \times 10^6$/ml | $20 \times 10^6$/ml | $10 \times 10^6$/ml[b] |
| 1.25 | 45 | 49 | 24 | 15 |
| 2.5 | 51 | 40 | 29 | 11 |
| 5.0 | 54 | 54 | 32 | 21 |
| 10.0 | 51 | 50 | 40 | 34 |
| 15.0 | 60 | | 41 | |
| 20.0 | 55 | | 40 | |

[a]Concentration to $20 \times 10^6$ sperm/ml was superior ($P < 0.05$) to $10 \times 10^6$ sperm/ml after 48 h storage. Also, initial dilution to $10 \times 10^6$ was superior to lower dilutions ($P < 0.05$).
Pooled standard errors ($\sqrt{\text{error mean square of ANOVA}} \div \sqrt{N}$) were 4.0 for 24 h, and 2.8 for 48 h incubations.
[b]Significant (log) linear trend ($P < 0.06$).

C. Conclusion

High sperm dilution and cooling resulted in a substantial reduction in the percentage of motile sperm, regardless of the presence or removal of seminal plasma. However, this dilution effect was greatly attenuated by concentrating the diluted sperm to $10 \times 10^6$/ml and even more, to $20 \times 10^6$/ml before storage at 5° C. Sperm from some bulls tolerated dilution better than sperm from other bulls; however, the bull differences found are typical. Extremely dilute sperm might be compromised during sorting, in part, by removal of protective compounds in seminal plasma.

Example 2

Effects of Equilibration Time Before Freezing Sorted Sperm

Objective: to evaluate the effect of equilibration times (3, 6 and 18 h, 5° C.) before freezing on flow-sorted sperm.

The following experiment was replicated in its entirety using the same bulls:

1. Collection of Source Sample. Sperm of 4 bulls were collected and prepared as described in Example 1A.

2. Methods.

a) Staining and Preparation for Sort.

i) Preparation of Stain Stock Solution: a stock solution of 8.89 mM Hoechst 33342 (bis-Benzimide H-33342; #190305, ICN Biomedicals Inc., Aurora, Ohio) was prepared in deionized water.

ii) Sperm Stain Procedure: sperm were diluted in a modified TALP buffer (Table 3) to $400 \times 10^6$ sperm/ml. Following dilution, Hoechst 33342 dye was added to the sperm suspensions at a concentration of 224 μM. After the stain was added to the sperm suspensions, the samples were incubated for 60 minutes at 34° C. Following incubation, sperm were diluted to $100 \times 10^6$/ml with TALP containing 2.67% clarified egg yolk and 0.002% food coloring dye (FD&C #40) which quenches the fluorescence of Hoechst 33342 in sperm with compromised cell membranes, allowing them to be gated out during the sorting process. Just prior to flow sorting, samples were filtered at unit gravity through a 40-μm nylon mesh filter to remove any debris and/or clumped sperm.

b) Sorting. A two-line argon laser operating at 351 and 364 nm and 150 mW was used to excite the Hoechst 33342 dye. The flow cytometer/cell sorter used was an SX MoFlo® (Cytomation, Inc., Fort Collins, Colo., USA) operating at 50 psi. A Tris-based sheath fluid was used, consisting of Tris(hydroxymethyl)aminomethane (Tris; 197.0 mM; #T-1503, Sigma Chemical Co., St. Louis, Mo., USA), citric acid monohydrate (55.4 mM; #C-7129, Sigma Chemical Co., St. Louis, Mo., USA) and fructose (47.5 mM; #F-0127, Sigma Chemical Co., St. Louis, Mo., USA). Baseline antibiotics were also added to the Tris-based sheath fluid consisting of 0.58 g/L of penicillin and 0.05 g/L of streptomycin sulfate.

The sperm were sorted by a process referred to as "bulk sorting" which permits rapid accumulation of large numbers of sperm so that large-scale examples can be done within a reasonable time. The sperm pass through the flow cytometer under the standard operating conditions with the exception that all droplets containing viable sperm were collected into a single tube rather than being sorted into 2 tubes based upon specific characteristics (e.g., sorting by sex-type). Sperm were sorted on the basis of viability; hence, sperm that have compromised plasma membranes were excluded during bulk sorting.

Stained sperm were maintained at 22±1° C. during sorting. Bulk sorted sperm were collected in 50-ml plastic tubes containing 2 ml of 20% egg yolk-Tris extender prepared with 20% egg yolk (vol/vol) in 200 mM Tris, 65 mM citric acid, 56 mM fructose, 50 μg/ml tylosin, 250 μg/ml gentamicin, and 150/300 μg/ml linco-spectin in deionized water. The egg yolk-Tris extender was termed "Tris-A fraction" to denote the lack of glycerol at this point in the procedure. Sperm were collected in tubes to contain 12 ml and approximately 6×10⁶ sperm. The sperm were subsequently incubated at 22° C. for 1 to 3 h to simulate conditions of a sort based on sex-type.

c) Preparation for Freezing. Following incubation, the sorted sperm were cooled to 5° C. over the period of 70 minutes. After cooling, the contents of the two tubes were pooled and transferred to a refrigerated, swinging bucket centrifuge set at 5° C. and centrifuged at 850×g for 20 minutes. After removing the supernatant, processing continued at 5° C. by adding about 150 µl of Tris-A fraction extender to about 150-µl of sperm pellet to bring the sperm concentration to approximately 40×10⁶/ml. The sperm of individual bulls were pooled and diluted immediately with an equal volume of egg yolk-Tris extender containing 12% (v/v) glycerol ("Tris-B fraction"). The Tris-B fraction was added to the sperm suspension as 2 equal volumes at 15-minute intervals to adjust the final sperm concentration to 20×10⁶/ml. The final glycerol concentration of the complete egg yolk-Tris extender containing the sperm was 6% (v/v).

d) Equilibration and Freezing. Extended sperm were then packaged into 0.25-ml polyvinylchloride straws to be frozen by routine procedures on racks in static liquid nitrogen vapor. Two straws from each of 4 bulls were frozen after 3, 6 and 18 h of total equilibration time at 5° C.

3. Evaluation of Post-Thaw Motility. Straws were thawed in a 37° C. water bath for 30 sec. Blind estimates of progressive motility were made after incubating samples at 37° C. for 0, 1 and 2 h post-thawing. Each of two observers estimated progressive sperm motility from each of two straws of semen. These four blind estimates for each experimental unit represent subsampling.

4. Statistical Analysis. Statistically, the subsamples were analyzed as a subplot to the main plot least-squares ANOVAs to analyze effects of any observer and observer x treatment interaction. N refers to the number of experimental units, not subsamples; standard errors were calculated on the basis of means of the 4 subsamples from error mean squares of ANOVAs and the numbers of experimental units; least-squares means are presented.

Treatment effects were evaluated via separate ANOVAs for each incubation time. The model included bulls as a random effect and equilibration time and observer as fixed effects; the subplot consisted of the observer term and related interactions.

5. Results. The 3- or 6-h equilibration times were superior to 18-h (Table 4), based on the percentage of progressively motile sperm, for 0 and 1 h (P<0.01) but not 2 h of post-thaw incubation. Effects of bull were evident at 1 and 2 h incubation times (P<0.05), but not at 0 h. There was no significant (P>0.1) bull by equilibration time interaction nor was there a significant observer effect for any response.

TABLE 3

| Modified TALP Buffer | |
| --- | --- |
| Ingredient | Concentration |
| NaCl | 95.0 mM |
| KCl | 3.0 mM |
| NaHPO₄ | 0.3 mM |
| NaHCO₃ | 10.0 mM |
| MgCl₂.6H₂O | 0.4 mM |
| Na Pyruvate | 2.0 mM |

TABLE 3-continued

| Modified TALP Buffer | |
| --- | --- |
| Ingredient | Concentration |
| Glucose | 5.0 mM |
| Na lactate | 25.0 mM |
| HEPES[a] | 40.0 mM |
| Bovine serum albumin[b] | 3.0 mg/ml |
| Gentamycin Sulfate | 30.0 µg/ml |

[a]#H3375, Sigma Chemical Co., St. Louis, MO, USA
[b]#US70195, fraction V; Amersham/Life Science, Cleveland, OH, USA

TABLE 4

| Effect of pre-freeze equilibration time on post-thaw progressive motility (%) | | | |
| --- | --- | --- | --- |
| Equilibration at 5° C. | Post-thaw incubation at 37° C. | | |
|  | 0 h | 1 h | 2 h |
| 3 h | 41[a] | 36[a,b] | 16 |
| 6 h | 41[a] | 37[a] | 18 |
| 18 h | 35[b] | 31[b] | 12 |
| S.E.[c] | 1.5 | 0.8 | 2.0 |

[a,b]Within columns, means without common superscripts differ (P < 0.05), Tukey's HSD.
[c]Pooled standard errors, √error mean square of ANOVA ÷ √N 6. Conclusion. The results indicated no differences in post-thaw sperm motility between 3 and 6 h of total equilibration time at 5° C., but there was a significant decline in sperm motility following 18 h of equilibration at 5° C. before freezing. The 3- to 6-h range permits pooling 2 consecutive 3-h sorting batches for freezing sperm without decreasing post-thaw motility.

As the bull by equilibration-time interaction was not significant, 3 to 6 h equilibration was adequate, with the caveat that only 4 bulls were used. The optimum equilibration time for a minority of bulls is expected to be >6 h.

Example 3

Effects of Stain Concentration and Laser Power on Sorted Sperm

Objective: to evaluate the effects of Hoechst 33342 dye concentration in combination with laser intensity on flow-sorted sperm.

1. Collection of Source Sample. Sperm of 6 bulls were collected and prepared as described in Example 1A.

2. Methods.
   a) Experimental Design. One ejaculate (2 bulls) and 2 ejaculates on different days (4 bulls) were used in a 2 by 2 design plus control.
   b) Staining and Sorting. Staining, preparation for sorting and sorting sperm were achieved as described in Example 2 except that the Hoechst 33342 dye was added to sperm suspensions at a final concentration of 149 µM or 224 µM; and sperm were bulked-sorted with the laser operating at 100 mW or 150 mW of incident power. Bulk-sorted sperm were collected into 50-ml plastic tubes as described in Example 2. Four tubes containing approximately 15×10⁶ total sperm/tube were collected over 1 h for each bull. The sorted sperm were incubated for 1 h at 22° C. to simulate a longer sorting time.

c) Preparation for Freezing. Following incubation, the sperm were cooled as in Example 2. The sperm were then concentrated by centrifugation at 5° C. at 850×g for 20 minutes. After removing the supernatant, 150 μl of Tris-A fraction extender was added to each 150-μl sperm pellet at 5° C. All of the sperm pellets were suspended by gentle repeated aspiration and the sperm of individual bulls were pooled. Tris B-fraction extender was added stepwise as described in Example 2. A non-stained, non-sorted control for each bull was prepared at 20×10$^6$ sperm/ml in Tris extender containing 6% glycerol and cooled to 5° C. while the bulk-sorted sperm were being prepared.

d) Equilibration and Freezing. The control and sorted sperm were packaged into 0.25-ml polyvinylchloride straws as described in Example 2, equilibrated at 5° C. for 3 h and then frozen conventionally.

3. Evaluation of Post-Thaw Motility. Straws were thawed and evaluated as described in Example 2.

4. Statistical Analysis. A general description of statistical analyses is provided in Example 2. Specifically, treatment effects were evaluated via ANOVA. The model included dye concentration, laser intensity and bulls in the main plot, and observer and related interactions in the subplot. Bulls were considered a random effect and the other factors as fixed.

5. Results. Bull effects were significant for percentages of progressively motile sperm immediately after thawing (P<0.1) and after 1 h and 2 h of incubation at 37° C. (P<0.05). There was no effect of dye concentration or bull by dye concentration on sperm motility at any incubation time. With bulls considered as a random effect, 150 mW of laser power resulted in lower post-thaw motility of sperm than 100 mW at 0 h of incubation (P<0.1), but not at other incubation times (Table 5). If bulls are considered as fixed effects, 150 mW of power resulted in lower sperm motility than 100 mW (P<0.05) at all 3 incubation times. There was an effect of bull by laser power (P<0.05) on sperm motility at 1 h, but not at 0-h or 2-h incubation times. Also, the higher laser power resulted in lower sperm motility than the control (P<0.05) at 0- and 1-h incubation times (Table 5). There was a significant observer effect at 1-h, but not at 0=h or 2-h, incubation times. There was no observer by treatment interaction (P>0.1).

TABLE 5

Effects of laser intensity and dye concentration on post-thaw motility (%).

| Main effect means | Incubation at 37° C. | | |
|---|---|---|---|
| | 0 h | 1 h | 2 h |
| Control | 49 | 44 | 33 |
| Dye Concentration | | | |
| 149 μM | 41 | 39 | 30 |
| 224 μM | 42 | 39 | 30 |
| Laser Intensity | | | |
| 100 mW | 46 | 42 | 33 |
| 150 mW | 38[a] | 35[b] | 27 |
| S.E.[c] | 2.2 | 1.2 | 1.3 |

[a]Significant main effect (P < 0.1) and differs from control (P < 0.05).
[b]Differs from control (P < 0.05).
[c]Pooled standard errors, √error mean square of ANOVA ÷ √N 6. Conclusion. Percentages of progressively motile sperm post-thaw were diminished by the staining and sorting process. Higher laser intensity was more damaging than the lower laser intensity. There was no effect of dye concentration on post-thaw sperm motility. Thus, excitation of the sperm-bound Hoechst 33342 dye at lower laser intensities is less damaging and that staining sperm at the higher dye concentration had no detrimental effect on post-thaw motility. The damage observed was presumably to the sperm-motility apparatus.

Example 4

Evaluation of Pre-Sort Staining Procedures and Selection of Extenders for the Cryopreservation of Sperm Objective: (1) to evaluate three pre-sort treatments for sperm; and, (2) and to evaluate sheath fluid and extender combinations for the cryopreservation of flow-sorted sperm.

The following experiment was replicated in its entirety:

1. Collection of Source Sample. Sperm from 4 bulls were collected and prepared as described in Example 1A.

2. Methods.

a) Experimental Design. A 3 (pre-sort treatments) by 3 (extenders) by 2 (sheath fluids) by 4 (bulls) by 2 (observers) factorial experiment was designed to determine the best procedure to hold sperm prior to sorting, and to evaluate three extenders for cryopreserving the sorted sperm.

b) Sample Preparation and Staining. Freshly collected sperm from each of 4 bulls were treated as follows:

(1) diluted to 400×10$^6$/ml in modified TALP (see Example 2, Table 3) and stained for 1 h at 34° C. before bulk-sorting ("Dilute—0 h");

(2) incubated neat at 22° C. for 3 h before dilution, staining and sorting ("Neat—3 h"); or, (3) diluted and stained as "Dilute-0 h" and then incubated at 22° C. for 3 h before bulk-sorting ("Diluted—3 h").

c) Extenders. The following freezing extenders were compared: EYC (see Example 1) containing 7% glycerol, egg yolk-Tris (see Example 2) containing 6% glycerol, and egg yolk-TES-Tris (TEST) containing 5% glycerol. EYC "A Fraction" refers to the EYC extender containing no glycerol, and EYC "B Fraction" refers to EYC extender containing twice the final, desired glycerol concentration (i.e., 14%). Thus, when EYC A and B fractions are combined in equal volume, the final EYC extender contains 7% glycerol. Tris A and B fractions are similarly named, and described in Example 2. TEST extender is prepared as a complete extender containing 5% glycerol; hence, there were no "A" and "B" fractions for TEST.

d) Sheath Fluid. Sheath fluid was either 98.6 mM sodium citrate dihydrate (#S279-3, Fisher Scientific, Fair Lawn, N.J.) or Tris as described in Example 2. Both types of sheath fluid were adjusted to pH 6.8; osmolality was about 270 to 280 mOsm/kg. Tris sheath fluid was used to collect sperm that were later extended in egg yolk-Tris and TEST freezing extenders. Sheath fluid containing 98.6 mM sodium citrate dihydrate was used to collect sperm to later be extended in EYC freezing extender.

e) Sorting. Approximately 58×10⁶ sperm for each combination of pre-sort treatment, sheath fluid and extender were bulk-sorted as described in Example 2 using 150 mW of incident laser power. For each sort, sperm were collected over approximately 1 h. After sorting, the samples were incubated at 22° C. for 2 h to simulate a 3 h sort.

f) Preparation for Freezing. Following incubation, the sperm were cooled as described in Example 2. After cooling, the samples were centrifuged at 5° C. at 850×g for 20 min. Each sample comprised about 28 ml total volume and was contained in a 50-ml plastic tube After the supernatant was removed, the sperm were returned to a 5° C. cold room for extension. Samples were extended to 40×10⁶/ml by depositing 131 µl of the sperm suspension into 69 µl of A-fraction EYC, A-fraction egg yolk-Tris, or TEST extender. Immediately, suspensions were adjusted to 20×10⁶ sperm/ml with the addition of the matched glycerol containing extender (i.e., B-fraction EYC, B-fraction Tris) or TEST. B-fraction extenders were added to their respective samples stepwise (2×) at 15-min intervals as described in Example 2. The TEST was added to sperm stepwise in the same manner as B-fraction EYC and Tris extenders.

g) Equilibration and Freezing. Sperm were packaged into 0.25-ml polyvinylchloride straws, equilibrated for 3 h at 5° C. and then frozen in static liquid nitrogen vapor.

3. Evaluation of Post-Thaw Motility. Thawing and post-thaw evaluations of sperm were done as described for Example 2.

4. Statistical Analysis. A general description of statistical analyses is provided in Example 2. Specifically, treatment effects were evaluated via separate analyses of variance for each post-thaw incubation time. The main plot included pre-sort treatment, extenders, and bulls; the subplot consisted of observers and associated interactions. Bulls were considered a random effect, and the other factors, fixed. The entire experiment was replicated twice. Tukey's HSD test was used to separate means.

5. Results. Post-thaw progressive motility of bulk-sorted sperm was affected (P<0.05) by extender and bulls at each post-thaw incubation time and by pre-sort procedure at 0 h of incubation (Table 6). There were no differences due to sheath fluids (P>0.05). At 0-h post-thaw incubation, use of the neat-3 h treatment resulted in more motile sperm after freezing and thawing than the other 2 pre-sort staining treatments (P<0.05; Table 6). However, pre-sort procedures were not statistically significant after post-thaw incubation of sperm for 1 or 2 h with bulls considered as a random effect. Importantly, at these 2 incubation times, there were significant pre-sort treatment by bull interactions (P<0.05). Furthermore, pre-sort treatment would have been a significant effect at all post-thaw incubation times had bulls been considered as fixed effects.

Immediately after thawing (0 h), TEST was the best extender, but after 1 or 2 h of incubation of 37° C., Tris was the best extender. Importantly, there was no pre-sort treatment by extender interaction for any response. There were observer effects (P<0.01) at all incubation times, but no observer by treatment interactions. There was a bull by extender interaction (P<0.05) at all 3 incubation times.

TABLE 6

Main effects of pre-sort treatment and freezing extenders on post-thaw progressive motility (%)

|  |  | Incubation at 37° C. | | |
| --- | --- | --- | --- | --- |
| Pre-sort procedure | Extender | 0 h | 1 h | 2 h |
| Dilute - 0 h | Mean | 39[a] | 32 | 22 |
| Neat - 3 h | Mean | 43[b] | 36 | 25 |
| Dilute - 3 h | Mean | 38[a] | 31 | 19 |
| Mean | EYC | 36[a] | 29[a] | 17[a] |
| Mean | Tris | 40[b] | 39[b] | 29[b] |
| Mean | TEST | 44[c] | 33[c] | 20[a] |
| S.E.[d] |  | 0.8 | 0.8 | 0.7 |

[a,b,c]Means within columns, within main effects, without common superscripts differ (P < 0.05).
[d]Pooled standard errors = $\sqrt{\text{error mean square of ANOVA}} \div \sqrt{N}$ 6. Conclusion. This study showed that holding sperm neat for 3 h before dilution, staining and sorting was better than immediate dilution and staining 0 h or 3 h later. Thus, by 3 h into the sort, it is best to continue with a new aliquot of the original ejaculate that was held neat 3 h and then stained, rather than continuing with the original sample of sperm stained and held at 400×10⁶ sperm/ml.

Even though TEST extender provided higher post-thaw motility at 0 h, Tris was the superior extender when sperm were stressed by incubation at 37° C. Either sheath fluid worked equally well for each extender. Based on these results, we have incorporated the use of Tris sheath fluid in combination with Tris freezing extender into our standard operating procedure.

Example 5

Effects of Extender Additives on Sorted Sperm

Objective: to evaluate the effect of adding sodium dodecyl sulfate ("SDS") to the freezing extender on flow-sorted sperm.

A. Evaluation of Effect of Concentration of SDS in Freezing Extender

1. Collection of Source Sample. Sperm of 6 bulls were collected and prepared as described in Example 1A.

2. Methods. Sperm from each of 6 bulls were extended to 20×10⁶/ml in 20% whole egg Tris ("WET") extender containing 0, 0.03, 0.06, 0.09, or 0.12 percent SDS, packaged into straws and frozen. WET extender was prepared using 3.028 g of Tris[hydroxymethyl]aminomethane, 1.78 g of citric acid monohydrate, and 1.25 g of fructose per 100 ml of double distilled water, to which 20% whole egg (vol/vol) was added. The WET extender was prepared at a pH of about 7.0 and contained a final glycerol concentration of about 6% (vol/vol). The WET extender also contained 1000 IU of penicillin "G" sodium and 100 µg of streptomycin sulfate/ml.

3. Results. The respective means (n=1 sample from each of 6 bulls) were 51, 51, 50, 51, and 48% progressive motile sperm approximately 10 minutes post-thaw. Based on these results, 0.06 percent SDS was used in Example 5B.

B. Evaluation of the Effects of 0.06 Percent SDS in Various Freezing Extenders on Post-Thaw Motility of Flow-Sorted Sperm 1. Collection of Source Sample. Sperm of 8 bulls were collected and prepared as described in Example 1A.

2. Methods. Post-thaw motility was studied for sperm frozen in egg yolk-Tris (see Example 2) and WET extenders (see Example 5A) with and without 0.06% SDS. Final glycerol content for both extenders was 6%.

a) Staining, Preparation for Sort. Sorting. Stained sperm samples were prepared from an ejaculate from each of 8 bulls as described in Example 2. Stained sperm were bulked-sorted using Tris sheath fluid as described in Example 2 except that the sort was achieved using 135 mW of incident laser power. Sorted sperm were collected in a 50-ml plastic tube containing 2 ml of A-fraction freezing buffer for each extender; $15 \times 10^6$ total sorted sperm (25 ml) for each treatment were collected and incubated for 1 h at 22° C. to simulate longer sorting.

b) Preparation for Freezing. Diluted sperm were then cooled to 5° C. over 90 minutes. An equal volume of appropriate B-fraction extender was added stepwise (2×) at 15-minute intervals to each 50-ml plastic tube containing sorted sperm. Aliquots of 25 ml/extender treatment were concentrated by centrifugation for 20 minutes at 850×g in a refrigerated centrifuge. The supernatant was removed leaving a 600 µl sperm pellet, which was suspended by gentle vortexing for 15 seconds. No additional extender was added to the sperm pellet since the suspension containing the pellet already contained glycerol. The concentration of the sperm suspension was approximately $20 \times 10^6$/ml. A non-stained, non-sorted control for each bull was prepared at $20 \times 10^6$ sperm/ml in egg-yolk-Tris extender containing 6% glycerol. The control was placed in a 5° C. cold room while bulk-sorting occurred.

c) Equilibration and Freezing. All control and bulk-sorted sperm were packaged and frozen at the same time. Sperm were packaged into 0.25-ml polyvinylchloride straws, equilibrated for about 3 h to about 6 h at 5° C. and then frozen in static liquid nitrogen vapor.

3. Evaluation of Post-Thaw Motility. Thawing and post-thaw evaluations of sperm were done as described for Example 2 with the exception that progressive motility was evaluated 0.5 and 2.0 h after incubation.

4. Statistical Analysis. A general description of statistical analyses is provided in Example 2. Specifically, treatment effects were evaluated via separate analyses of variance for each incubation time; the model included bull and extender in the main plot and observer and related interactions in the subplot. Differences in means were determined by the least significant difference test.

5. Results. Extender affected (P<0.05) progressive motility of sperm after 0.5 or 2 h post-thaw incubation (Table 7). At 0.5 h, WET plus SDS resulted in lower motility than Tris with SDS. At 2 h, all treatments with bulk-sorted sperm were worse than the non-sorted control sperm. There were significant bull and observer effects (P<0.01) at both incubation times, but no observer by treatment interactions.

TABLE 7

Effect of extender on post-thaw progressive motility (%)

| | Incubation at 37° C. | |
|---|---|---|
| Extender | 0.5 h | 2 h |
| Tris (non-sort) | 42[a] | 41[a] |
| Tris w/o SDS | 40[a,b] | 35[b] |
| Tris w/SDS | 42[a] | 37[b] |

TABLE 7-continued

Effect of extender on post-thaw progressive motility (%)

| | Incubation at 37° C. | |
|---|---|---|
| Extender | 0.5 h | 2 h |
| WET w/o SDS | 40[a,b] | 35[b] |
| WET w/SDS | 38[b] | 35[b] |
| S.E.[c] | 1.0 | 1.2 |

[a,b]Means within columns without common superscripts differ (P < 0.05).
[c]√error mean square of ANOVA ÷ √N 6. Conclusion. The inclusion of SDS in Tris or WET extenders did not benefit sperm quality as determined by visual estimates of motility after thawing. Also, results using WET and Tris extenders were similar; hence, WET appeared as efficacious as Tris for cryopreserving sorted bovine sperm.

Example 6

Quality of Sperm Sexed by Flow Sorting for Field Trials

Objective: to evaluate post-thaw quality of sorted sperm based on acrosomal integrity.

1. Collection of Source Sample. Sperm of 3 bulls were collected and prepared as described in Example 1A.

2. Methods. Sorted and non-sorted control sperm from the same ejaculate were stained, processed, and sorted as described in Example 2 except the sperm were sorted for sex-type at a 90% purity level. Sorted sperm were collected to a volume of approximately 20 ml and were cooled to 5° C. for 90 minutes (0.2° C./min). After cooling, an equal volume of egg yolk-Tris B extender (see Example 2) was added to the sorted sperm in 2 equal volumes at 15-minute intervals. Centrifugation and aspiration of the supernatant were achieved as described in Example 5. After centrifugation and aspiration, egg yolk-Tris extender containing 6% glycerol (v/v) was added to the sperm pellet to bring the concentration of sperm to about $20 \times 10^6$/ml. Freezing and thawing were done as described in Example 2 except that equilibration time was about 3 h.

3. Evaluation of Post-Thaw Motility. Visual estimates of the percentage of progressively motile sperm at 37° C. were made approximately 10 minutes after thawing. The acrosomal integrity of sperm was assessed using differential interference-contrast microscopy (×1000) after 2 h of incubation at 37° C. Sperm were treated with 40 mM sodium fluoride, a wet was smear made, and 100 sperm per treatment were examined. Acrosomes were classified as: (a) intact acrosome, (b) swollen or damaged acrosome, or (c) missing acrosome (non-intact).

4. Statistical Analysis. The data analyzed were from 19 different freeze dates balanced across 3 bulls used in field trials. Treatment effects (sort vs. control) were evaluated via analysis of variance with bulls as a fixed effect.

5. Results. The percentage of progressively motile sperm post-thaw was significantly higher (P<0.05) for non-sorted sperm (50%) than for sorted sperm (46%; Table 8), despite removal of dead sperm during sorting. However, the percentage of sperm with an intact acrosome was not different. Sorting increased the percentage of sperm missing an acrosome, but also reduced the percentage of sperm with a damaged acrosome, relative to control sperm (P<0.05).

There were significant differences among bulls for percent of intact acrosomes (P<0.05), percent of non-intact acrosomes (P<0.01), and post-thaw progressive motility (P<0.01). There was a bull by sorting effect for post-thaw motility (p<0.01) but not for the other responses. From bulls A and B, differences in post-thaw motility between sorted and unsorted sperm were near zero; for bull C, sorted sperm were 10 percentage points (19%) lower in motility than control sperm.

TABLE 8

Effect of sorting on post-thaw motility (%) and acrosomal status (%).

| | Acrosomal status | | | Post-thaw motility |
|---|---|---|---|---|
| | Intact | Damaged | Non-intact | |
| Control | 64[a] | 20[a] | 15[a] | 50[a] |
| Sorted | 65[a] | 14[b] | 21[b] | 46[b] |

[a,b]Column means with different superscripts differ (P < 0.05).

6. Conclusion. Visual estimates of progressive motility for sorted, frozen sperm on average were slightly lower (4 percentage points; 8%) than for control sperm, although this difference was larger for one bull. These evaluations were made approximately 10 minutes after thawing. The small average difference is consistent with that for non-intact acrosomes after 2 h of incubation. Sperm with a damaged or missing acrosome are likely to be immotile. The increased percentage of sperm with a non-intact acrosome, for sorted samples, indicates damage associated with sorting or with cryopreservation before or after actual sorting. Presumably, sorting converted damaged acrosomes to missing acrosomes. Based on standard procedures for evaluation of sperm quality, there is no basis for assuming that fertilizing potential of these flow-sorted sperm should be severely compromised for most bulls.

Example 7

Sex-Selection and Cryopreservation of Bull Sperm Using 20% Egg Yolk-Tris Extender Objective: to provide a protocol for the cryopreservation of flow-sorted bull sperm.

1. Collection and Ejaculate Assessment. Collect and prepare ejaculates as described in Example 1A. Select ejaculates from those bulls with >75% morphologically normal sperm. Visually estimate the percentage of progressively motile sperm (ejaculates that have progressive motility >60% are best for sorting). Add antibiotics to raw semen as follows: tylosin at a final concentration 100 μg/ml, gentamicin at a final concentration of 500 μg/ml, and linco-spectin at a final concentration of 300/600 μg/ml.

2. Staining and Preparation for Sort. Following the addition of the antibiotics to the raw semen sample, allow 15–20 minutes before staining. Stain samples as described in Example 2.

3. Sorting. Sort for both X— and Y— type sperm, setting the sorting gates for 90% purity. Sort sperm into 50-ml Falcon tubes containing 2 ml 20% egg yolk-Tris A-fraction extender (see Example 2) until each tube contains a maximum of 20 ml total volume (or a maximum of 2 h per sort) and final sorted sperm concentration is 6×10⁶/ml. Note that additional 20% egg yolk-Tris-A fraction catch buffer must be added after the sort and prior to cooling so that the final percentage of egg yolk is at least 3%.

4. Preparation for Freezing. Following the sort, cool the sorted samples to 5° C. over a period of 90 minutes. After cooling, add 20% egg yolk-Tris B-fraction extender (see Example 2) stepwise (2×) at 15 minutes intervals. The final volume of Tris B-fraction extender added to the sperm sample should be equal to the volume of Tris A-fraction extender. The total volume of sperm sample after the Tris B-fraction extender is added should not exceed 27 ml total volume.

After the Tris B-fraction extender is added to the sperm sample, concentrate the sample by centrifugation for 20 minutes at 850×g. Aspirate the supernatant leaving approximately 150 μl sperm pellet. Resuspend the sperm and pool the sperm for each individual bull.

5. Freezing. Add complete egg yolk-Tris extender (6% glycerol) to achieve a final sperm concentration of 20×10⁶/ml. Package the extended sperm into 0.25-ml polyvinylchloride straws for freezing as described in Example 2.

Example 8

Evaluation of the Fertility of Flow-Sorted, Frozen Bull Sperm in Field Studies

Materials and Methods

Semen Collection and Processing

Semen from young bulls of unknown fertility was collected via artificial vagina (see Example 1A). After determining sperm concentration with a spectrophotometer and subjective evaluation of progressive sperm motility, semen was processed and sorted as described in Example 2 except that the sperm were sorted by sex-type at 90% purity using a laser incident power of about 135 to about 150 mW. Processing and freezing was achieved as in Example 2 except that the equilibration time was about 3 h. Cornell Universal Extender (Seidel G E Jr., Theriogenology 1997; 48:1255–1264) was used for liquid semen in field trials 1, 2, and 3. For frozen semen in field trials 2 and 3, the extender used was 2.9% Na citrate+20% egg yolk with a final glycerol concentration of 7% (see Example 1). For field trials 4 through 11, sperm were frozen in a Tris-based extender composed of 200 mM Tris, 65 mM citric acid, 56 mM fructose, 20% egg yolk, and a final glycerol concentration of 6% (see Example 2). The sheath fluid used in the flow cytometer was 2.9% Na citrate (see Example 4) for trials 1, 2, and 3, and a Tris buffer for the remaining trials (see Example 2).

Sperm were packaged in 0.25-mi French straws in columns as small as 50 μl in the center of the straw. To minimize dilution effects, low volumes were used so there were at least 10⁷ sperm/ml. In most trials, a column of extender without sperm was aspirated into the straw first to wet the cotton plug, followed by a small column of air, and then the sexed sperm. When sperm were frozen, one straw from each batch was thawed in 35° C. water for 30 sec for quality control, and batches with less than 25% progressive motility post thaw were discarded. A sample of sexed sperm from each batch was sonicated and analyzed by flow cytometry to determine the accuracy of sexing.

Heifer Management and Artificial Insemination

The heifers used were in 6 widely scattered production units with different management practices. Seasonal and breed differences contributed further to the heterogeneity of the experiments (Table 9). Insofar as possible, treatments and controls were alternated systematically within bulls within inseminators as heifers entered the insemination facilities.

Estrus was synchronized in one of 4 ways (Table 9): (1) 500 mg of melengesterol acetate (MGA) fed daily in 2.3 kg of grain for 14 days followed by an i.m. injection of 25 mg prostaglandin $F_2\alpha$ (Lutalyse, Upjohn, Kalamazoo, Mich., USA) 17, 18 or 19 days after the last day of feeding MGA (MGA/PG); (2) a single injection of 25 mg of prostaglandin $F_2\alpha$ (PG); (3) 20 or 25 mg of prostaglandin $F_2\alpha$ injected i.m. at 12-day intervals (PG/PG) or (4) 50 or 100 µg of GnRH injected i.m., followed by 25 mg of prostaglandin $F_2\alpha$ 7 days later (GnRH/PG).

Heifers were inspected visually for standing estrus mornings and evenings, but inseminated only in the evenings after 16:00, approximately ½ or 1 day after onset of estrus. Insemination was either into the uterine body conventionally, or half into each uterine horn using atraumatic embryo transfer sheaths (IMV, Minneapolis, Minn., USA). In the latter case, semen was deposited past the greater curvature of the uterine horn as far anterior as could be accomplished without trauma, identically to nonsurgical embryo transfer. In most cases, semen was deposited between the anterior third and mid-cornua.

Most experiments included a frozen sperm control inseminated into the uterine body with or $40 \times 10^6$ sperm/dose from the same bulls used for sperm sorted for sex-type ("sexed"). This control served as a composite estimate of the intrinsic, normal fertility of the heifers under the specific field-trial conditions as well as the fertility of the bulls used and the skills of the inseminators. Some trials also included a low-dose, unsexed control group. Sometimes numbers of control inseminations were planned to be ½ or ⅔ the number used for each treatment to obtain more information on sexed sperm. Frozen sexed and control sperm were thawed for 20 to 30 sec in a 35 to 37° C. water bath. Various other details are summarized in Table 9.

Pregnancy was diagnosed by ultrasound 28 to 37 d post insemination and/or 56 to 92 d post-insemination, at which time fetal sex was determined in most trials, as described in Curran, S., Theriogenology 1991; 36:809–814, without the operator's knowing insemination treatments or controls. Sexes of calves born were nearly identical to the fetal-sex diagnosis. Data were analyzed by single-degree-of-freedom Chi square corrected for continuity; 2-tail tests were used unless 1-tail is specified. Fewer than 5% of the inseminations were culled due to errors of insemination treatment, frank infection of the reproductive tract, failure to traverse the cervix, etc. Decisions to cull animals from experiments were made shortly after insemination and were never based on the pregnancy diagnosis.

TABLE 9

Procedural details of field trials

| Trial | Insemination dates | Breeds of heifers | Bulls used | Inseminators | Estrus synchronization | Comments |
|---|---|---|---|---|---|---|
| 1 | 5/20–23, 1997 | Angus | N1, N2, AN4 | A, B | MGA/PG | Included low-dose controls |
| 2 | 2/18–5/22, 1998 | Angus crossbred | N3, N4, N5, N6 | C, D | PG/PG | Low dose but no normal-dose controls; some heifers pregnant and aborted when synchronized |
| 3 | 6/2–6/5, 1998 | Angus | AN4, AN5, N7, N8 | B, D | MGA/PG | |
| 4 | 2/10–13, 1999 | Holstein | J2, J4 | C, D | PG | Very severe mud, snow, wind, and cold, driving rain |
| 5 | 2/24–26, 1999 | Holstein | J2, J4, J5 | C, B, D | PG/PG | |
| 6 | 4/14–16, 1999 | Holstein | J2, J3, J4, J5 | C, D | PG | Some heifers were reproductive culls |
| 7 | 4/27–5/1, 1999 | Hereford & Angus crossbred | AN1, AN4 | C | MGA/PG | Semen for 1 bull shipped 6 h before sorting; severe weather |
| 8 | 4/21–23, 1999 | Angus crossbred | H1, H2 | E | MGA/PG | Feedlot heifers |
| 9 | 5/5–8, 1999 | Red Angus | AR1, AR2 | C, F | MGA/PG | |
| 10 | 5/31–6/2, 1999 | Angus | AN4, AN7, AN8 | B, D | GnRH/PG | |
| 11 | 7/28–30, 1999 | Holstein | H2, H3 | C, D | PG/PG | First replicate available in a much larger trial |

Results and Discussion

The data presented are from 11 consecutive, heterogeneous field trials, constrained by logistical aspects of the studies, such as having to match bulls to genetic needs of the herds, unavailability of fertility information on bulls, limited numbers of heifers, unavailability of the same inseminators across trials, severe weather in some trials, limited amounts of sexed semen in early trials, 2 sets of heifers in which some turned out to be pregnant up to about 55 days at the time of estrus synchronization, etc. Up to 4 bulls and 3 inseminators were involved with each trial; this enabled us to sample populations to ensure that results applied to more than one bull or technician; however, insufficient data were produced to evaluate bull-to-bull differences in fertility rigorously.

Most sets of heifers were from breeding herds located 140 to 250 km from our laboratory. There were no significant differences in pregnancy rates between inseminators in any trial, but numbers of breedings per inseminator were low, and differences likely would be detected with larger numbers of inseminations.

Estrus synchronization methods were not compared within trials, so it was not possible to compare pregnancy rates among these methods. Pregnancy rates appeared to be satisfactory for all four synchronization procedures used.

Since inseminations were done once a day, heifers in estrus evenings were inseminated approximately 24 h after estrus was detected. The pregnancy rate for these heifers with sexed sperm pooled over all trials was 203/414 (49.0%), which was not significantly different (P>0.1) from that of heifers in estrus mornings and thus inseminated half a day after estrus detection 266/586 (45.4%). This tendency for higher fertility with later insemination is in agreement with findings from other research that it is preferable to inseminate later than normally recommended with lower fertility bulls, when low sperm numbers are used, or when conditions are otherwise suboptimal.

Pregnancy rates by treatments and, when available, fetal or calf sex are presented in Tables 10 to 20. The objective was to obtain female offspring, except in trial 8; accuracy was 95%, 83%, 90%, 83%, 82%, and 94% in Trials 1, 3, 8, 9, 10, and 11, respectively. In the remainder of the trials, fetal or birth sexes were not available because of timing of pregnancy diagnosis, unavailability of persons skilled in sexing fetuses, and/or because calves have not yet been born. This was not a major concern because the main objective of this research was to determine fertility of flow-sorted sperm inseminated at low doses.

The accuracy of sexing can be adjusted to virtually any level desired between 50 and 95+% by adjusting the sorting parameters. However, higher accuracy results in lower numbers of sperm sorted per unit time, particularly for Y-chromosome sperm. 90% accuracy is sufficient for routine work.

The main findings from each field trial will be summarized in turn. Note that total sperm numbers are given in table headings; numbers of progressively motile sperm usually were 30 to 50% of these values. Field trial 1 (Table 10) confirmed that pregnancy rates with uterine horn insemination using low numbers of unsexed sperm were similar to controls with normal sperm numbers. The day 64 to 67 pregnancy rate with unfrozen sexed sperm (42%) was 12 percentage points below the unsexed liquid control with sperm diluted, stained, and centrifuged identically to the sorted sperm. Accuracy of sexing was 95%; the sex of calves born from sexed sperm matched the sex diagnosis of fetuses exactly; there was one mistake in sexing fetuses of controls. There were no abortions between 2 months of gestation and term, and all 19 calves from the sexed sperm treatment were normal and survived. For the sexed semen treatment, the 2-month pregnancy rates for bulls N1, N2, and N3 were 41, 44, and 40%, respectively; 39% (13/33) of heifers in estrus in the morning and 50% (6/12) in estrus in the evening became pregnant.

TABLE 10

Results of field trial 1 - Angus heifers in Wyoming, 1997

| Treatment/site | No. sperm | No. heifers | No. pregnant day 31 to 33 | No. pregnant day 64 to 67 | No. ♀ calves |
|---|---|---|---|---|---|
| Sexed, 5° C./horns | $3 \times 10^5$ | 45 | 20 (44%) | 19 (42%) | 18 (95%)[a] |
| Control, 5° C./horns | $3 \times 10^5$ | 28 | 15 (54%) | 15 (54%) | 5 (53%)[b] |
| Frozen, control/body | $40 \times 10^6$ | 29 | 16 (55%) | 15 (52%) | 11 (73%)[a,b] |

[a,b]Sex ratios without common superscripts differ (P < 0.02).

Field trial 2 (Table 11) provided the first evidence that results with sexed, frozen sperm are similar to sexed, unfrozen sperm if adjustment is made for numbers of sperm killed during cryopreservation. There also was no difference in pregnancy rates between sexed sperm stored at 5 versus 18° C. Pregnancy rates at 2+ months after insemination for sexed semen from individual bulls ranged from 22 to 42% pregnant (P>0.05). Embryonic loss between 1 and 2 months of gestation was very similar for sexed and control pregnancies. Calving data were available from 39 heifers from this trial; each of these heifers (30 sexed pregnancies, 9 controls) pregnant at 2 months calved after a normal-length gestation.

TABLE 11

Results of field trial 2 - Crossbred beef heifers in Colorado, 1998

| Treatment/site | No. sperm | No. heifers | No. pregnant day 30 to 35[a] | No. pregnant day 59 to 92[a] |
|---|---|---|---|---|
| Control, 5° C./horns | $5 \times 10^5$ | 58 | 27 (47%) | 24 (41%) |
| Sexed, 5° C./horns | $5 \times 10^5$ | 51 | 17 (33%) | 16 (31%) |
| Sexed, 18° C./horns | $5 \times 10^5$ | 46 | 16 (35%) | 12 (26%) |
| Sexed, frozen/horns | $1 \times 10^6$ | 87 | 29 (33%) | 28 (32%) |

[a]No significant differences, $\chi^2$.

Field trial 3 (Table 12) confirmed that sexed, frozen sperm results in reasonable pregnancy rates. The accuracy of sexing sperm was confirmed again; however, there were 4 errors in sexing fetuses relative to the calves born; the actual sexes of calves born are presented. Again, there were no abortions between 2 months of gestation and term. Pregnancy rates averaged over sexed, unfrozen and sexed, frozen sperm for bulls N8, N9, AN5, and AN4 were 24, 31, 50, and 60%, respectively (P<0.1).

TABLE 12

Results of field trial 3 - Angus heifers in Wyoming, 1998

| Treatment/site | No. sperm | No. heifers | No. pregnant day 62 to 65 | No. ♀ calves |
|---|---|---|---|---|
| Sexed, 18° C./horns | $5 \times 10^5$ | 37 | 11 (30%)[a] | 10 (91%)[c] |
| Sexed, frozen/horns | $1 \times 10^6$ | 35 | 18 (51%)[a,b] | 14 (78%)[c] |
| Frozen, control/body | $40 \times 10^6$ | 37 | 27 (73%)[b] | 16 (59%)[d] |

[a,b]Means without common superscripts differ P < 0.05).
[c,d]The percentage of ♀ calves from the sexed treatments (83%) differed from the control group, P < 0.05, 1-tail, $\chi^2$.

Field trials 4, 5, and 6 (Tables 13, 14, 15) were done at the same location with 3 different groups of heifers. Unfortunately, it was not possible to replicate each trial similarly due to vagaries of field trials, such as scheduling personnel, availability of sexed semen from each bull, etc. The widely different pregnancy rates between trials 5 and 6 illustrate that conditions were different among trials. Some of the heifers in trial 6 were available because they failed to get pregnant after a month of natural mating. Under conditions of these trials, pregnancy rates were very similar between 1.5 and $3.0 \times 10^6$ sexed, frozen sperm/dose. Furthermore, there was no advantage to uterine-horn insemination. There were no significant differences (P>0.05) in pregnancy rates among bulls except in Trial 5 in which the pregnancy rate of J2, 20/28 (71%), was higher than that of J4, 15/39 (38%) (P<0.05). This difference was not consistent from trial to trial, as J4 had numerically but not significantly (P>0.1) higher pregnancy rates than J2 in Trials 4 and 6.

TABLE 13

Results of field trial 4 - Holstein heifers in Colorado, 1999

| Treatment/site | No. sperm | No. heifers | No. pregnant day 30 to 33 | No. pregnant day 64 to 67* |
|---|---|---|---|---|
| Sexed, frozen/body | $1.5 \times 10^6$ | 55 | 36 (65%)[a,b] | 36 (65%)[a,b] |
| Sexed, frozen/body | $3 \times 10^6$ | 52 | 27 (52%)[a] | 26 (50%)[a] |
| Control, frozen/body | $20 \times 10^6$ | 55 | 45 (82%)[b] | 43 (78%)[b] |

[a,b]Means without common superscripts differ (P < 0.01).
*Six heifers pregnant at d 30 to 33 were sold before the second pregnancy diagnosis; these were assumed to have remained pregnant.

TABLE 14

Results of field trial 5 - Holstein heifers in Colorado, 1999

| Treatment/site | No. sperm | No. heifers | No. pregnant day 33 to 35[a] | No. pregnant day 60 to 62[a] |
|---|---|---|---|---|
| Sexed, frozen/body | $1.5 \times 10^6$ | 23 | 12 (52%) | 12 (52%) |
| Sexed, frozen/body | $3.0 \times 10^6$ | 25 | 15 (60%) | 14 (56%) |
| Sexed, frozen/horns | $1.5 \times 10^6$ | 25 | 15 (60%) | 12 (48%) |
| Sexed, frozen/horns | $3.0 \times 10^6$ | 25 | 17 (68%) | 15 (60%) |
| Control, frozen/body | $20 \times 10^6$ | 30 | 20 (67%) | 19 (63%) |

[a]No significant differences.

TABLE 15

Results of field trial 6 - Holstein heifers in Colorado, 1999

| Treatment/site | No. sperm | No. heifers | No. pregnant day 31 to 34 | No. pregnant day 60 to 63 |
|---|---|---|---|---|
| Sexed, frozen/body | $1.5 \times 10^6$ | 27 | 11 (41%)[a] | 9 (33%)[a] |
| Sexed, frozen/body | $3.0 \times 10^6$ | 25 | 10 (40%)[a] | 9 (36%)[a] |
| Sexed, frozen/horns | $1.5 \times 10^6$ | 24 | 8 (33%)[a] | 7 (29%)[a] |
| Sexed, frozen/horns | $3.0 \times 10^6$ | 24 | 10 (42%)[a] | 8 (33%)[a] |
| Control, frozen/body | $20 \times 10^6$ | 24 | 18 (75%)[b] | 17 (71%)[b] |

[a,b]Means without common superscripts differ (P < 0.05).

For trial 7 (Table 16), only one inseminator was available due to rescheduling. This is the only trial that showed a convincing advantage of uterine-horn over uterine-body insemination. For this inseminator under the conditions of the trial, 55% more heifers (22 percentage points) became pregnant with sexed, frozen semen inseminated into the uterine horns than into the uterine body. The true difference could be smaller because there are wide confidence intervals on these means. In all the other trials (5, 6, 9, and 11) in which body- and horn-insemination were compared, pregnancy rates were very similar for both methods for this technician as well as for other technicians.

Semen from one of the bulls used in Trial 7 was shipped without dilution from Montana by air in an insulated box at ~20° C. before sorting; shipping time was 6 h. Pregnancy rates for the sexed sperm from the two bulls were virtually identical, 49% for the unshipped and 52% for the shipped semen. Semen was not diluted with extender and not cooled for shipping because staining properties of sperm with Hoechst 33342 are altered by dilution with extenders. Furthermore, in other studies (see Example 4), storing semen neat at ambient temperature between collection and flow-sorting was found to be superior to diluting it.

TABLE 16

Results of field trial 7 - Crossbred beef heifers in Colorado, 1999

| Treatment/site | No. sperm | No. heifers | No. pregnant day 33 to 37 |
|---|---|---|---|
| Sexed, frozen/body | $1.5 \times 10^6$ | 86 | 34 (40%)[a] |
| Sexed, frozen/horns | $1.5 \times 10^6$ | 86 | 53 (62%)[b] |
| Control, frozen/body | $20 \times 10^6$ | 35 | 18 (51%)[a,b] |

[a,b]Means without common superscripts differ (P < 0.01).

Field trial 8 (Table 17) concerned feedlot heifers not implanted with growth promotants; at the time pregnancy was diagnosed they were aborted, so calving data was not available. This experiment illustrates that efficacious sexing also can be done in the male direction. Pregnancy rates for the 2 bulls were 50 and 61%.

TABLE 17

Results of field trial 8 - Angus heifers in Nebraska, 1999

| Treatment/site | No. sperm | No. heifers | No. pregnant[a] day 74 to 76 | No. ♂ fetuses |
|---|---|---|---|---|
| Sexed, frozen, 72 mW laser/body | $1 \times 10^6$ | 18 | 7 (39%) | 6 (86%) |
| Sexed, frozen, 135 mW laser/body | $1 \times 10^6$ | 18 | 13 (78%) | 12 (92%) |

[a]No significant differences.

Field trial 9 (Table 18) was the only trial to show a convincing advantage of 3.0 versus $1.5 \times 10^6$ sexed, frozen sperm/insemination dose. This advantage was true for both inseminators. Pregnancy rates for sexed sperm from the 2 bulls were 62 and 75%.

TABLE 18

Results of field trial 9 - Red Angus heifers in Nebraska, 1999

| Treatment/site | No. sperm | No. heifers | No. pregnant day 60 to 63[a] | No. ♀ fetuses |
|---|---|---|---|---|
| Sexed, frozen/body | $1.5 \times 10^6$ | 15 | 8 (53%) | 7 (88%) |
| Sexed, frozen/body | $3.0 \times 10^6$ | 14 | 12 (86%) | 9 (75%) |
| Sexed, frozen/horns | $1.5 \times 10^6$ | 16 | 9 (56%) | 7 (78%) |
| Sexed, frozen/horns | $3.0 \times 10^6$ | 16 | 12 (75%) | 11 (92%) |
| Control, frozen/body | $20 \times 10^6$ | 30 | 21 (70%) | 13 (62%) |

[a]$3.0 \times 10^6$ sexed sperm had a higher pregnancy rate (80%) than $1.5 \times 10^6$ sexed sperm (55%), P < 0.05, 1-tail $\chi^2$.

Pregnancy rates in field trial 10 (Table 19) with sexed, frozen semen, were similar to controls; the accuracy of sexing sperm on this trial was only 82%, which, however, is not significantly different from the targeted 90% accuracy. Pregnancy rates for sexed semen were 54, 66, and 50% for bulls AN4, AN7, and AN8, respectively (P>0.1). Eighteen of the heifers inseminated in this trial were the calves resulting from sexed sperm in field trial 1.

TABLE 19

Results of field trial 10 - Angus heifers in Wyoming, 1999

| Treatment/site | No. sperm | No. heifers | No. pregnant day 61 to 63[a] | No. ♀ fetuses |
|---|---|---|---|---|
| Sexed, frozen/body | $1 \times 10^6$ | 44 | 26 (59%) | 23 (85%) |
| Sexed, frozen/body | $3 \times 10^6$ | 43 | 23 (53%) | 17 (74%) |
| Control, frozen/body | $20 \times 10^6$ | 35 | 20 (57%) | 12 (57%) |

[a]No significant differences.

TABLE 20

Results of field trial 11 - Holstein heifers in Colorado, 1999

| Treatment/site | No. sperm | No. heifers | No. pregnant day 28 to 30[a] | No. pregnant day 56 to 58[a,b] |
|---|---|---|---|---|
| Sexed, frozen/body | $1 \times 10^6$ | 12 | 8 (67%) | 7 (58%) |
| Sexed, frozen/body | $3 \times 10^6$ | 12 | 6 (50%) | 4 (33%) |
| Sexed, frozen/horns | $1 \times 10^6$ | 7 | 4 (57%) | 4 (57%) |
| Sexed, frozen/horns | $3 \times 10^6$ | 7 | 4 (57%) | 4 (57%) |
| Control, frozen/body | $20 \times 10^6$ | 9 | 4 (44%) | 3 (33%) |

[a]No significant differences, $\chi^2$.
[b]16 of 17 (94%) fetuses from the sexed semen treatments were female; 2 were too deep in the body cavity to sex with ultrasound.

Data from trials were combined in which treatments were identical except 1×10 and 1.5×10⁶ sperm doses were pooled (Table 21).

TABLE 21

Meta-summary from combining trials with sexed, frozen semen and frozen controls.

| Trials combined | Sperm no./site | No. heifers | No. pregnant |
|---|---|---|---|
| 5, 6, 9, 11 | $1.0–1.5 \times 10^6$/body | 77 | 36 (47%) |
|  | $3.0 \times 10^6$/body | 76 | 38 (50%) |
|  | $1.0–1.5 \times 10^6$/horns | 72 | 32 (44%) |
|  | $3.0 \times 10^6$/horns | 72 | 39 (54%) |
|  | $20 \times 10^6$/body, control | 93 | 61 (66%) |
| 4, 5, 6, 9, 10, 11 | $1.0–1.5 \times 10^6$/body | 176 | 98 (56%) |
|  | $3.0 \times 10^6$/body | 171 | 88 (51%) |
|  | $20 \times 10^6$/body, control | 183 | 124 (68%) |
| 5, 6, 7, 9, 11 | $1.5 \times 10^6$/body | 163 | 70 (43%) |
|  | $1.5 \times 10^6$/horn | 158 | 85 (54%) |
|  | $20 \times 10^6$/body, control | 128 | 79 (62%) |

Pregnancy rates with sexed sperm were generally 70–90% of unsexed controls within experiments with 7 to 20 times more sperm. This difference was less in the more recent trials, possibly reflecting improved sexing and sperm-processing procedures.

In some trials, heifers were examined for pregnancy by ultrasound at both 1 and 2 months after insemination. Pregnancy losses in this interval were similar (P>0.1) for sexed (23/261; 8.8%) versus control (9/145; 6.2%) sperm treatments, which is one measure that genetic damage due to sexing is minimal. Calving information was obtained from only a few of the pregnant heifers because most cattle from the earlier trials were sold, and those from later trials have not calved yet. The population of calves produced to date from sexed semen appears to be no different from the population of controls.

CONCLUSION

Sex ratios in cattle can be distorted to about 90% of either sex by sorting sperm on the basis of DNA content with a flow cytometer/cell sorter followed by cryopreservation and relatively routine artificial insemination. Calves resulting from sexed sperm appear to be normal. For most bulls in these studies, pregnancy rates with 1.0 to 1.5×10⁶ sexed, frozen sperm were 70 to 90% of unsexed controls with 20 or 40×10⁶ frozen sperm inseminated conventionally. These results apply to well-managed heifers bred by well-trained inseminators using properly processed semen. There may be a small advantage to inseminating sexed sperm bilaterally into the uterine horns compared to standard uterine body insemination.

The present invention has of necessity been discussed herein by reference to certain specific methods and materials. It is to be understood that the discussion of these specific methods and materials in no way constitutes any limitation on the scope of the present invention, which extends to any and all alternative materials and methods suitable for accomplishing the ends of the present invention.

All patents and publications described are herein incorporated by reference in their entirety.

What is claimed is:

1. A method of cryopreserving sex-selected sperm cells, comprising:
    a. obtaining sperm cells from a species of a non-human male mammal;
    b. sorting said sperm cells, without the presence of protective compounds in seminal plasma, and based upon sex-type to provide a collection of sex-selected sperm cells obtained using flow cytometry or fluorescence-activated cell sorting;
    c. cooling said sex-selected sperm cells;
    d. suspending said sex-selected sperm cells in an extender to provide a concentration of sperm cells of about 5 million per milliliter of extender to about 10 million per milliliter of extender; and
    e. freezing said sex-selected sperm cells in said extender.

2. A method of cryopreserving sex-selected sperm cells as described in claim 1, wherein said sperm cells from said species of said non-human male mammal are selected from the group consisting of bovine sperm cells and equine sperm cells.

3. A method of cryopreserving sperm cells as described in claim 2, further comprising a step of isolating a number of bovine sperm cells between about 300,000 and about 3,000,000.

4. A method of cryopreserving sperm cells as described in claim 2, further comprising a step of isolating a number of bovine sperm cells of no more than about 1,000,000.

5. A method of cryopreserving sex-selected sperm cells as described in claim 1, wherein said sperm cells from said species of said non-human male mammal comprise equine sperm cells.

6. A method of cryopreserving sex-selected sperm cells as described in claim 5, further comprising a step of isolating a number of equine sperm cells between about 1,000,000 and about 25,000,000.

7. A method of cryopreserving sex-selected sperm cells as described in claim 5, further comprising a step of isolating a number of equine sperm cells of no more than about 5,000,000.

8. A method of cryopreserving sex-selected sperm cells as described in claim 1, wherein said step of cooling sex-selected sperm cells comprises reducing temperature of said sex-selected sperm cells to about 5° C.

9. A method of cryopreserving sex-selected sperm cells as described in claim 8, wherein said step of reducing the temperature of said sex-selected sperm cells comprises reducing the temperature of said sex-selected sperm cells for a period of about 60 minutes to about 240 minutes.

10. A method of cryopreserving sex-selected sperm cells as described in claim 1, wherein said extender further comprises a component which maintains osmolality and buffers pH.

11. A method of cryopreserving sex-selected sperm cells as described in claim 10, wherein said component which maintains osmolality and buffers pH is selected from the group consisting of a buffer comprising a salt, a buffer containing a carbohydrate, and any combination thereof.

12. A method of cryopreserving sex-selected sperm cells as described in claim 10, wherein said component which maintains osmolality and buffers pH is selected from the group consisting of sodium citrate,Tris[hydroxymethyl]aminomethane, 200 mM Tris[hydroxymethyl]aminomethane, 175 mM to 225 mM Tris[hydroxymethyl]aminomethane, 200 mM Tris[hydroxymethyl]aminomethane/65 mM citric acid monohydrate, 175 mM to 225 mM Tris[hydroxymethyl]aminomethane/50 mM to 70 mM citric acid monohydrate, N-Tris [hydroxymethyl]methyl-2-aminoethanesulfonic acid, 200 mM Tris[hydroxymethyl]methyl-2-aminoethanesulfonic acid, 175 mM to 225 mM Tris[hydroxymethyl]methyl-2-aminoethanesulfonic acid, 200 mM Tris[hydroxymethyl]methyl-2-aminoethanesulfonic acid/65 mM citric acid monohydrate, 175 mM to 225 mM Tris[hydroxymethyl]methyl-2-aminoethanesulfonic acid/50 mM to 70 mM citric acid monohydrate, monosodium glutamate, milk, HEPES buffered medium, and any combination thereof.

13. A method of cryopreserving sex-selected sperm cells as described in claim 10, 11, or 12, wherein said extender has a pH in the range of about 6.5 to about 7.5.

14. A method of cryopreserving sex-selected sperm cells as described in claim 13, wherein said extender further comprises a cold shock protectant.

15. A method of cryopreserving sex-selected sperm cells as described in claim 14, wherein said cold shock protectant is selected from the group consisting of egg yolk, 20% egg yolk, 15% to 25% egg yolk, an egg yolk extract, milk, a milk extract, casein, albumin, lecithin, and any combination thereof.

16. A method of cryopreserving sex-selected sperm cells as described in claim 14, wherein said extender further comprises an energy source.

17. A method of cryopreserving sex-selected sperm cells as described in claim 16, wherein said energy source is selected from the group consisting of a saccharide, glucose, fructose, 56 mM fructose, 45 mM to 60 mM fructose, mannose, and any combination thereof.

18. A method of cryopreserving sex-selected sperm cells as described in claim 16, wherein said extender further comprises an antibiotic.

19. A method of cryopreserving sex-selected sperm cells as described in claim 18, wherein said antibiotic is selected from the group consisting of tylosin, gentamicin, lincomycin, linco-spectin, spectinomycin, penicillin, streptomycin, and any combination thereof.

20. A method of cryopreserving sex-selected sperm cells as described in claim 10, wherein said extender further comprises a cryoprotectant.

21. A method of cryopreserving sex-selected sperm cells as described in claim 20, wherein said cryoprotectant is selected from the group consisting of disaccharides, trisaccharides, and any combination thereof.

22. A method of cryopreserving sex-selected sperm cells as described in claim 20, wherein said cryoprotectant is selected from the group consisting of glycerol, 6% glycerol, between 5% to 7% glycerol, dimethyl sulfoxide, ethylene glycol, propylene glycol, and any combination thereof.

23. A method of cryopreserving sex-selected sperm cells as described in claim 1, wherein the extender in which said sex-selected sperm cells are suspended comprises glycerol, sodium citrate, Tris[hydroxymethyl]aminomethane, egg yolk, fructose, and one or more antibiotics.

24. A method of cryopreserving sex-selected sperm cells as described in claim 1, wherein the extender in which said sex-selected sperm cells are suspended comprises glycerol, sodium citrate, egg yolk, and one or more antibiotics.

25. A method of cryopreserving sex-selected sperm cells as described in claim 1, wherein the extender in which said sex-selected sperm cells are suspended comprises glycerol, egg yolk, milk, fructose, and one or more antibiotics.

26. A method of cryopreserving sex-selected sperm cells as described in claim 1, further comprising a step of equilibrating said sex-selected sperm cells suspended in said extender to a cooler, non-freezing temperature for a period of time prior to said freezing step (e) for a period of about 1 hour to about 18 hours.

27. A method of cryopreserving sex-selected sperm cells as described in claim 22, further comprising a step of equilibrating said sex-selected sperm cells suspended in said extender to a cooler, non-freezing temperature for a period of time prior to said freezing step (e) over a period of not greater than 6 hours.

28. A method of cryopreserving sperm cells as described in claim 1, wherein said step of freezing said sex-selected sperm cells in said extender comprises freezing a number of bovine sperm cells between about 300,000 and about 5,000,000.

* * * * *